United States Patent
Park et al.

(10) Patent No.: US 12,139,491 B2
(45) Date of Patent: Nov. 12, 2024

(54) DIKETOPIPERAZINE DERIVATIVES AS CALCIUM ATPASE INHIBITOR FOR ENHANCING ANTICANCER ACTIVITY

(71) Applicant: HOLOSMEDIC, Gyeonggi-do (KR)

(72) Inventors: Ki Cheong Park, Seoul (KR); Jae Ho Cheong, Seoul (KR); Seok Mo Kim, Seoul (KR); Yeo Jin Yun, Gyeonggi-do (KR); Byeong Mo Kim, Seoul (KR)

(73) Assignee: HOLOSMEDIC, Gyeonggi-do (KR)

( * ) Notice: Subject to any disclaimer, the term of this patent is extended or adjusted under 35 U.S.C. 154(b) by 693 days.

(21) Appl. No.: 17/418,323

(22) PCT Filed: Dec. 27, 2019

(86) PCT No.: PCT/KR2019/018660
§ 371 (c)(1),
(2) Date: Jun. 25, 2021

(87) PCT Pub. No.: WO2020/139044
PCT Pub. Date: Jul. 2, 2020

(65) Prior Publication Data
US 2022/0064171 A1    Mar. 3, 2022

(30) Foreign Application Priority Data

Dec. 27, 2018 (KR) .................. 10-2018-0170842
Dec. 27, 2019 (KR) .................. 10-2019-0176706

(51) Int. Cl.
*C07D 487/04* (2006.01)
*A61K 31/337* (2006.01)
(Continued)

(52) U.S. Cl.
CPC .......... *C07D 487/04* (2013.01); *A61K 31/337* (2013.01); *A61K 31/4745* (2013.01);
(Continued)

(58) Field of Classification Search
CPC ................ C07D 487/04; C07D 487/14; A61K 31/337; A61K 31/4745; A61K 31/4985; A61K 45/06; A61P 35/00
See application file for complete search history.

(56) References Cited

FOREIGN PATENT DOCUMENTS

JP       2015-028018 A     2/2015
KR   10-2013-0042565 A     4/2013
(Continued)

OTHER PUBLICATIONS

U.S. Appl. No. 17/772,311, filed Apr. 27, 2022, Yun; Yeo Jin.*
(Continued)

*Primary Examiner* — Clinton A Brooks
*Assistant Examiner* — Kyle Nottingham
(74) *Attorney, Agent, or Firm* — Harness, Dickey & Pierce, P.L.C.

(57) ABSTRACT

The present invention relates to a novel compound and a pharmaceutical composition for enhancing anticancer activity, which includes the same, and more particularly, to a pharmaceutical composition, which includes a compound represented by Formula 1 or a pharmaceutically acceptable salt thereof, thereby enhancing anticancer activity of an anticancer agent or radiation, and inducing proliferation inhibition and death of cancer cells, resulting in effectively treating cancer:

[Formula 1]

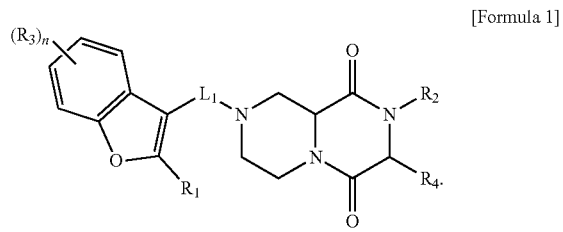

19 Claims, 16 Drawing Sheets

(51) Int. Cl.
*A61K 31/4745* (2006.01)
*A61K 31/4985* (2006.01)
*A61K 45/06* (2006.01)
*A61P 35/00* (2006.01)
*C07D 487/14* (2006.01)

(52) U.S. Cl.
CPC .......... *A61K 31/4985* (2013.01); *A61K 45/06* (2013.01); *A61P 35/00* (2018.01); *C07D 487/14* (2013.01)

(56) References Cited

FOREIGN PATENT DOCUMENTS

KR 10-2018-0045656 A 5/2018
WO WO-01-46197 A1 6/2001

OTHER PUBLICATIONS

U.S. Appl. No. 18/011,599, filed Dec. 20, 2022, Yun, Yeo Jin.*
Michelangeli, Francesco, and J. Malcolm East. "A Diversity of SERCA Ca2+ Pump Inhibitors." Biochemical Society Transactions, vol. 39, No. 3, Jun. 2011, pp. 789-797. DOI.org (Crossref), https://doi.org/10.1042/BST0390789. (Year: 2011).*
Examination Report from corresponding Australian Patent Application No. 2019416623, dated Dec. 1, 2021.
Office Action from corresponding Canadian Patent Application No. 3124938, dated Nov. 22, 2022.
Extended European Search Report from corresponding European Patent Application No. 19904270.6, dated Sep. 15, 2022.
Office Action from corresponding Japanese Patent Application No. 2021-536764, dated Jun. 4, 2022.
Answer 1 Registry, Chemical Library, 2022.
Office Action from corresponding Russian Patent Application No. 2021121992, dated Mar. 3, 2022.
Search Report from corresponding Russian Patent Application No. 2021121992, dated Mar. 3, 2022.
Office Action from corresponding Korean Patent Application No. 10-2019-0176706, dated Feb. 22, 2022.
Chemical Abstract Compound. STN express. RN 1268968-87-1 (Mar. 21, 2011).
International Search Report from corresponding PCT Application No. PCT/KR2019/018660, dated Apr. 6, 2020.
Chemical Abstract Compound. STN express. RN 1268967-89-0 (Mar. 21, 2011).

* cited by examiner

DIKETOPIPERAZINE DERIVATIVES AS CALCIUM ATPASE INHIBITOR FOR ENHANCING ANTICANCER ACTIVITY

CROSS-REFERENCE TO RELATED APPLICATIONS

This application is a national phase application of PCT Application No. PCT/KR2019/018660, filed on Dec. 27, 2020, which claims the benefit and priority to Korean Patent Application Nos. 10-2018-0170842, filed on Dec. 27, 2018 and 10-2019-0176706, filed on Dec. 27, 2019. The entire disclosures of the applications identified in this paragraph are incorporated herein by references.

TECHNICAL FIELD

The present invention relates to a novel compound and a pharmaceutical composition for enhancing anticancer activity including the same.

BACKGROUND ART

Cancer is one of the common causes of death around the world, and accounts for approximately 12% of deaths.

Chemotherapy, which is a typical anticancer therapy, is currently being used as the most efficient therapeutic method for treating cancer alone or in combination with a different therapeutic method such as radiation therapy. However, in chemotherapy, the efficacy of a cancer therapeutic agent depends on its ability to kill cancer cells, but there is a problem of not only acting on cancer cells, but also acting on general cells when the agent is used. Meanwhile, cancer stem cells are cancer cells having unlimited regenerative ability, the hypothesis that a tumor originates from stem cells was proved by the disclosure in the late 90s that when cells that can become cancer stem cells in acute myeloid leukemia are transplanted into immunosuppressed mice and thereby human leukemia is reproduced in the mice, and the presence of stem cells was also confirmed in solid carcinomas by proving the presence of cancer stem cells in breast cancer.

Cancer stem cells are cells that have a self-renewal ability and the ability to differentiate into different cells, and act as the cause of cancer recurrence and metastasis. A specific patient group is classified as intractable cancer patients, who are difficult to treat by conventional chemotherapy, due to a strong resistance to an anticancer agent as cancer stem cells are activated. The diverse heterogeneity shown in malignant tumors is consistent with a variety of differentiation of stem cells, and despite many targeted therapies, the constantly expressed drug resistance of cancer cells is consistent with the basic properties of stem cells. Cancer stem cells may be a new targeted therapy field, and in order to efficiently perform treatment only targeting cancer cells without damaging normal stem cells, knowledge and understanding of the molecular biology properties critical for the maintenance and regulation of cancer stem cells or regulatory pathways thereof are required. Several treatment methods have been devised based on the cancer stem cell hypothesis, and the most well-known method is a method using the self-renewal pathway of cancer stem cells. The important thing in these treatments is to target only the self-renewal of cancer stem cells while maintaining the self-renewal of normal stem cells. For example, Notch signaling is processed by an enzyme called gamma secretase, and by the use of a gamma secretase inhibitor in Notch1-overexpressing breast cancer, a tumor inhibitory effect may be achieved. There is a recent report that an anticancer effect is shown when a Hedgehog signaling system is targeted, and when cyclopamine, which is a Hedgehog inhibitor, was administered to a tumor xenograft animal, the tumors dramatically shrunk. The other methods are associated with PI3K/AKT, MAPK, and JAK2/STAT3 signaling pathways.

As such, a number of studies are being conducted to suppress cancer stem cells by suppressing cancer stem cells by an experiment for suppressing a direct target gene of the cancer stem cells or suppressing an upstream signaling protein of the cancer stem cells. However, to date, there are few studies on anticancer agents or extracts derived from natural substances directly targeting cancer stem cells, and in most tumor patients, there are many difficulties in a targeting experiment due to oncogene mutations or protein mutations. Meanwhile, there is a previous research result which reveals that the critical reason for the anticancer agent resistance of cancer stem cells is attributable to sarco/endoplasmic reticulum calcium ATPase (SERCA), which is a protein involved in transport and storage of calcium ions in cells. It was shown that, when an anticancer agent is administered, in general cancer cells, excessive stress is induced, calcium ions are excessively secreted from the endoplasmic reticulum (ER), and the secreted calcium ions are accumulated in the mitochondria, leading to the death of cancer cells, whereas cancer stem cells survive while the concentration of calcium ions is regulated by increasing the expression of SERCA which reduces the secretion of excessive calcium ions and also returns the excessively secreted calcium ions to the ER when an anticancer agent is administered. That is, SERCA protein may play a role in survival signaling in an ER stress signaling process. When a substance that can serve as an inhibitor targeting the SERCA protein, which is a cause of anticancer agent resistance of cancer stem cells, is developed to selectively inhibit the growth of the cancer stem cells, by increasing the efficacy of chemotherapy by an anticancer agent, an excellent anticancer effect may be exhibited with a lower dose of the agent.

SUMMARY

Technical Problem

The present invention is directed to providing a novel compound.

The present invention is also directed to providing a pharmaceutical composition for enhancing anticancer activity.

Technical Solution

[Claim 1]
1. A compound represented by Formula 1 below or a pharmaceutically acceptable salt thereof:

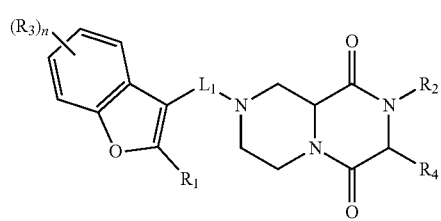

[Formula 1]

In Formula 1, n is an integer of 0 to 4;

R₁ is hydrogen, C1 to C10 alkyl or aryl(C1 to C4)alkyl;

R₃ is C1 to C6 alkyl, and when there are a plurality of the R₃, the R₃s are the same or different;

L₁ is a direct bond, or C1 to C6 alkylene; R₂ is hydrogen, C1 to C10 alkyl or aryl(C1 to C4)alkyl, and R₄ is hydrogen, C1 to C4 alkyl, C3 to C8 cycloalkyl or aryl(C1 to C4)alkyl, or R₂ and R₄ are connected to form a 4 to 7-membered ring; and the alkyl of R₁ to R₄, the arylalkyl of R₁, R₂ and R₄, the cycloalkyl of R₄, the alkylene of L₁ are each independently unsubstituted or substituted with a substituent such as a C1 to C6 alkyl group, a halo group, an aryl group, a haloalkyl group, a nitro group, a cyano group, an alkylthio group or an arylalkylthio group, and when the compound is substituted with a plurality of substituents, the substituents are the same or different.

2. The compound of 1, wherein n is an integer of 0 to 2;

R₁ is C1 to C6 alkyl or aryl(C1 to C2)alky;

L₁ is C1 to C4 alkylene; and

R₂ is hydrogen, C1 to C6 alkyl or aryl(C1 to C2)alkyl, and R₄ is hydrogen, C1 to C4 alkyl, C3 to C6 cycloalkyl or aryl(C1 to C2)alkyl, or R₂ and R₄ are connected to form a 4 to 6-membered ring.

3. The compound of claim 1, wherein n is an integer of 0 to 1;

R₁ is C1 to C6 alkyl, phenylmethyl or phenylethyl;

L₁ is C1 to C2 alkylene;

R₂ is hydrogen, C1 to C6 alkyl, phenylmethyl or phenylethyl, R₄ is hydrogen, C1 to C2 alkyl, C5 to C6 cycloalkyl, phenylmethyl or naphthylmethyl, or R₂ and R₄ are connected to form a 5 to 6-membered ring.

4. A pharmaceutical composition for enhancing anticancer activity, comprising the compound represented by Formula 1 below or a pharmaceutically acceptable salt thereof:

[Formula 1]

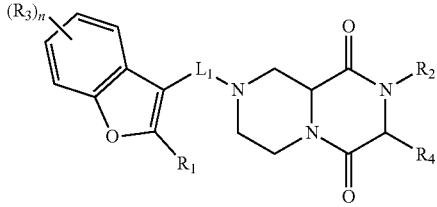

In Formula 1, n is an integer of 0 to 4;

R₁ is hydrogen, C1 to C10 alkyl or aryl(C1 to C4)alkyl;

R₃ is C1 to C6 alkyl, and when there are a plurality of the R₃, the R₃s are the same or different;

L₁ is a direct bond, or C1 to C6 alkylene;

R₂ is hydrogen, C1 to C10 alkyl or aryl(C1 to C4)alkyl, and R₄ is hydrogen, C1 to C4 alkyl, C3 to C8 cycloalkyl or aryl(C1 to C4)alkyl, or R₂ and R₄ are connected to form a 4 to 7-membered ring; and the alkyl of R₁ to R₄, the arylalkyl of R₁, R₂ and R₄, the cycloalkyl of R₄, the alkylene of L₁ are each independently unsubstituted or substituted with a substituent such as a C1 to C6 alkyl group, a halo group, an aryl group, a haloalkyl group, a nitro group, a cyano group, an alkylthio group or an arylalkylthio group, and when the compound is substituted with a plurality of substituents, the substituents are the same or different.

5. The pharmaceutical composition of claim 4, wherein n is an integer of 0 to 2;

R₁ is C1 to C6 alkyl or aryl(C1 to C2)alky;

L₁ is C1 to C4 alkylene; and

R₂ is hydrogen, C1 to C6 alkyl or aryl(C1 to C2)alkyl, and R₄ is hydrogen, C1 to C4 alkyl, C3 to C6 cycloalkyl or aryl(C1 to C2)alkyl, or R₂ and R₄ are connected to form a 4 to 7-membered ring.

6. The pharmaceutical composition of claim 4, wherein n is an integer of 0 to 1;

R₁ is C1 to C6 alkyl, phenylmethyl or phenylethyl;

L₁ is C1 to C2 alkylene;

R₂ is hydrogen, C1 to C6 alkyl, phenylmethyl or phenylethyl, R₄ is hydrogen, C1 to C2 alkyl, C5 to C6 cycloalkyl, phenylmethyl or naphthylmethyl, or R₂ and R₄ are connected to form a 5 to 6-membered ring.

7. The pharmaceutical composition of claim 4, wherein the enhancement in anticancer activity is enhancement in anticancer activity of an anticancer agent or radiation.

8. The pharmaceutical composition of claim 7, wherein the anticancer agent is at least one of a taxene-based anticancer agent and a camptothecin-based anticancer agent.

9. The pharmaceutical composition of claim 8, wherein the taxene-based anticancer agent is at least one selected from the group consisting of paclitaxel, docetaxel and cabazitaxel.

10. The pharmaceutical composition of claim 8, wherein the camptothecin-based anticancer agent is at least one selected from the group consisting of irinotecan, topotecan and velotecan.

11. The pharmaceutical composition of claim 4, which is for enhancing anticancer activity against resistant cancer.

12. The pharmaceutical composition of claim 11, wherein the resistant cancer is resistant cancer against at least one of a taxene-based anticancer agent and a camptothecin-based anticancer agent.

13. The pharmaceutical composition of claim 11, wherein the resistant cancer is resistant cancer against radiation.

14. The pharmaceutical composition of claim 11, wherein the resistant cancer is at least one selected from the group consisting of thyroid cancer, stomach cancer, colorectal cancer, ovarian cancer, breast cancer, lung cancer, Kaposi's sarcoma, cervical cancer, pancreatic cancer, head and neck cancer, rectal cancer, colon cancer, esophageal cancer and prostate cancer.

15. The pharmaceutical composition of claim 4, further comprising an anticancer agent.

16. The pharmaceutical composition of claim 15, wherein the anticancer agent is at least one selected from the group consisting of nitrogen mustard, imatinib, oxaliplatin, rituximab, erlotinib, neratinib, lapatinib, gefitinib, vandetanib, nilotinib, semasanib, bosutinib, axitinib, macitinib, cediranib, restaurtinib, trastuzumab, gefitinib, bortezomib, sunitinib, pazopanib, toceranib, nintedanib, regorafenib, semaksanib, tibozanib, ponatinib, cabozantinib, carboplatin, sorafenib, renbatinib, bevacizumab, cisplatin, cetuximab, viscumalbum, asparaginase, tretinoin, hydroxycarbamide, dasatinib, estramustine, gemtuzumab ozogamycin, ibritumomab tucetan, heptaplastin, methylaminolevulinic acid, amsacriine, alemtuzumab, procarbazine, alprostadil, holmium nitrate, chitosa, gemcitabine, doxyfluridine, pemetrexed, tegapur, capecitabine, gimeracil, oteracil, azacitidine, methotrexate, uracil, cytarabine, 5-fluorouracil, fludagabine, enocitabine, flutamide, kefecitabine, decitabine, mercaptopurine, thioguanine, cladribine, carmofur, raltitrexed, docetaxel, paclitaxel, irinotecan, velotecan, topotecan, binorelbine, etoposide, vincristine, vinblastine, teniposide, doxorubicin, idarubicin, epirubicin, mitoxantrone, mitomycin, bleromycin, daunorubicin, dactinomycin, pararubicin, aclarubicin, pepromycin, temsirolimus, temozolomide, busulfan, ifosfamide, cyclophosphmide, melparan, altretmin, dacarbazine, thiotepa, bimustine, chlorambucil, mitoractol, leucovorin, tretonin, exnestane, aminoglutesimide, anagrelide, olaparib, navelbine, padrazol, tamoxifen, toremifen, testolactone, anastrozole, letrozole, borozole, bicalutamide, lomustine, vorinostat, entinostat and carmustine.

17. The pharmaceutical composition of claim 15, wherein the compound represented by Formula 1 or a pharmaceutically acceptable salt thereof and the anticancer agent are contained at a molar concentration ratio of 1:0.001 to 1:1000.

18. A method of treating cancer, comprising:
administering a therapeutically effective amount of a compound represented by Formula 1 below or a pharmaceutically acceptable salt thereof to a subject with resistant cancer:

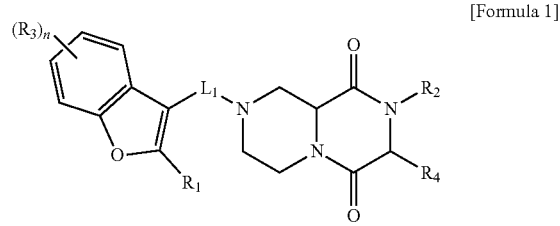

[Formula 1]

In Formula 1,
n is an integer of 0 to 4;
$R_1$ is hydrogen, C1 to C10 alkyl or aryl(C1 to C4)alkyl;
$R_3$ is C1 to C6 alkyl, and when there are a plurality of the $R_3$, the $R_3$s are the same or different;
$L_1$ is a direct bond, or C1 to C6 alkylene; $R_2$ is hydrogen, C1 to C10 alkyl or aryl(C1 to C4)alkyl, and $R_4$ is hydrogen, C1 to C4 alkyl, C3 to C8 cycloalkyl or aryl(C1 to C4)alkyl, or
$R_2$ and $R_4$ are connected to form a 4 to 7-membered ring; and
the alkyl of $R_1$ to $R_4$, the arylalkyl of $R_1$, $R_2$ and $R_4$, the cycloalkyl of $R_4$, the alkylene of $L_1$ are each independently unsubstituted or substituted with a substituent such as a C1 to C6 alkyl group, a halo group, an aryl group, a haloalkyl group, a nitro group, a cyano group, an alkylthio group or an arylalkylthio group, and when the compound is substituted with a plurality of substituents, the substituents are the same or different.

19. The method of claim 18, wherein n is an integer of 0 to 2;
$R_1$ is C1 to C6 alkyl or aryl(C1 to C2)alkyl;
$L_1$ is C1 to C4 alkylene; and
$R_2$ is hydrogen, C1 to C6 alkyl or aryl(C1 to C2)alkyl, and $R_4$ is hydrogen, C1 to C4 alkyl, C3 to C6 cycloalkyl or aryl(C1 to C2)alkyl, or
$R_2$ and $R_4$ are connected to form a 4 to 6-membered ring.

20. The method of claim 18, wherein n is an integer of 0 to 1;
$R_1$ is C1 to C6 alkyl, phenylmethyl or phenylethyl;
$L_1$ is C1 to C2 alkylene;
$R_2$ is hydrogen, C1 to C6 alkyl, phenylmethyl or phenylethyl, $R_4$ is hydrogen, C1 to C2 alkyl, C5 to C6 cycloalkyl, phenylmethyl or naphthylmethyl, or
$R_2$ and $R_4$ are connected to form a 5 to 6-membered ring.

21. The method of claim 18, wherein the resistant cancer is resistant cancer against at least one of a taxene-based anticancer agent and a camptothecin-based anticancer agent.

22. The method of claim 18, wherein the resistant cancer is resistant cancer against radiation.

23. The method of claim 18, wherein the resistant cancer is at least one selected from the group consisting of thyroid cancer, stomach cancer, colorectal cancer, ovarian cancer, breast cancer, lung cancer, Kaposi's sarcoma, cervical cancer, pancreatic cancer, head and neck cancer, rectal cancer, colon cancer, esophageal cancer and prostate cancer:

24. A use of a compound represented by Formula 1 below for treating resistant cancer:

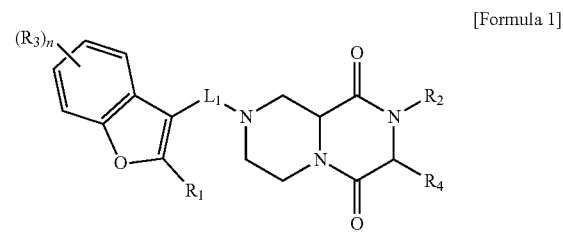

[Formula 1]

In Formula 1,
n is an integer of 0 to 4;
$R_1$ is hydrogen, C1 to C10 alkyl or aryl(C1 to C4)alkyl;
$R_3$ is C1 to C6 alkyl, and when there are a plurality of the $R_3$, the $R_3$s are the same or different;
$L_1$ is a direct bond, or C1 to C6 alkylene;
$R_2$ is hydrogen, C1 to C10 alkyl or aryl(C1 to C4)alkyl, and $R_4$ is hydrogen, C1 to C4 alkyl, C3 to C8 cycloalkyl or aryl(C1 to C4)alkyl, or
$R_2$ and $R_4$ are connected to form a 4 to 7-membered ring; and
the alkyl of $R_1$ to $R_4$, the arylalkyl of $R_1$, $R_2$ and $R_4$, the cycloalkyl of $R_4$, the alkylene of $L_1$ are each independently unsubstituted or substituted with a substituent such as a C1 to C6 alkyl group, a halo group, an aryl group, a haloalkyl group, a nitro group, a cyano group, an alkylthio group or an arylalkylthio group, and when the compound is substituted with a plurality of substituents, the substituents are the same or different.

25. The use of claim 24, wherein n is an integer of 0 to 2;
$R_1$ is C1 to C6 alkyl or aryl(C1 to C2)alky;
$L_1$ is C1 to C4 alkylene; and
$R_2$ is hydrogen, C1 to C6 alkyl or aryl(C1 to C2)alkyl, and $R_4$ is hydrogen, C1 to C4 alkyl, C3 to C6 cycloalkyl or aryl(C1 to C2)alkyl, or
$R_2$ and $R_4$ are connected to form a 4 to 6-membered ring.

26. The use of claim 24, wherein n is an integer of 0 to 1;
$R_1$ is C1 to C6 alkyl, phenylmethyl or phenylethyl;
$L_1$ is C1 to C2 alkylene;
$R_2$ is hydrogen, C1 to C6 alkyl, phenylmethyl or phenylethyl, $R_4$ is hydrogen, C1 to C2 alkyl, C5 to C6 cycloalkyl, phenylmethyl or naphthylmethyl, or $R_2$ and $R_4$ are connected to form a 5 to 6-membered ring.

27. The use of claim 24, wherein the resistant cancer is resistant cancer against at least one of a taxene-based anticancer agent and a camptothecin-based anticancer agent.
28. The use of claim 24, wherein the resistant cancer is resistant cancer against radiation.
29. The use of claim 24, wherein the resistant cancer is at least one selected from the group consisting of thyroid cancer, stomach cancer, colorectal cancer, ovarian cancer, breast cancer, lung cancer, Kaposi's sarcoma, cervical cancer, pancreatic cancer, head and neck cancer, rectal cancer, colon cancer, esophageal cancer and prostate cancer.

Advantageous Effects

A composition including a compound of the present invention or a pharmaceutically acceptable salt thereof can enhance the anticancer activity of an anticancer agent or radiation, and effectively treat cancer by inhibiting the proliferation of cancer cells and inducing cell death. The composition including the compound of the present invention or a pharmaceutically acceptable salt thereof can overcome the resistance of cancer against an anticancer agent or radiation, and effectively treat resistant cancer.

DETAILED DESCRIPTION

Figure 1:
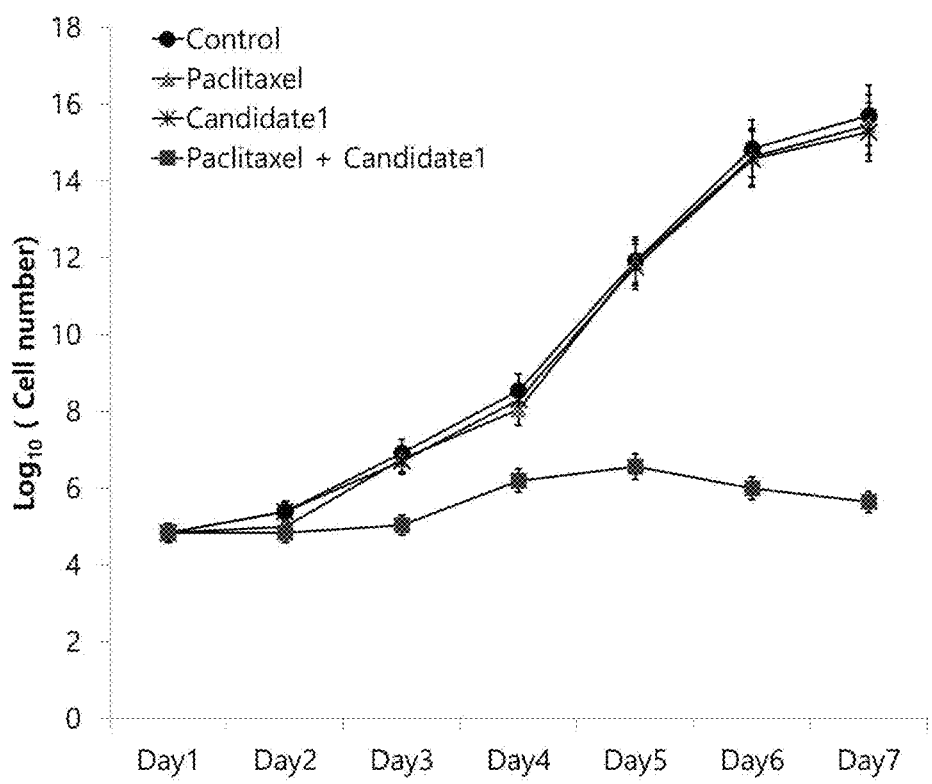
FIG. 1 shows the result of measuring a change in number of cells according to treatment time after cancer stem cell-like thyroid cancer cells derived from patients with relapse and metastasis after paclitaxel administration are treated with a compound of Preparation Example 1-1 only; paclitaxel only; or the combination of paclitaxel and a compound of Preparation Example 1-1.

A compound of Formula 1 below and/or a pharmaceutically acceptable salt thereof exhibit(s) an inhibitory effect on a SERCA protein responsible for survival signaling in ER stress signaling. The present invention provides a compound represented by Formula 1 below or a pharmaceutically acceptable salt thereof:

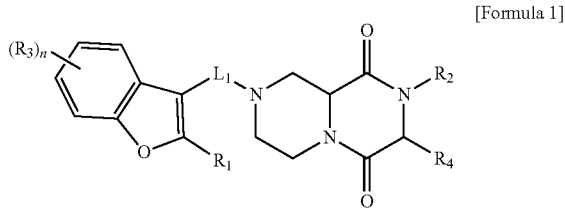

[Formula 1]

In Formula 1, $R_1$ may be hydrogen, C1 to C10 alkyl, or aryl(C1 to C4)alkyl.

In Formula 1, $R_1$ may be C1 to C6 alkyl or aryl(C1 to C2)alkyl.

In Formula 1, $R_1$ may be C1 to C6 alkyl, phenylmethyl or phenylethyl.

In Formula 1, the alkyl and arylalkyl of $R_1$ may each be independently unsubstituted or substituted with a substituent such as C1 to C6 alkyl, a halo group, an aryl group, a haloalkyl group, a nitro group, a cyano group, an alkylthio group or an arylalkylthio group. In Formula 1, when the $R_1$ alkyl and/or arylalkyl are(is) substituted with a plurality of substituents, each substituent may be the same or different.

In Formula 1, when $R_1$ is arylalkyl, an alkyl group, a halo group, a haloalkyl group, a cyano group, a nitro group or a phenyl group may be substituted at a para position.

The term "alkyl" refers to a linear or branched unsubstituted or substituted saturated hydrocarbon group, and includes, for example, methyl, ethyl, propyl, isopropyl, isobutyl, sec-butyl, tert-butyl, pentyl, hexyl, heptyl, octyl, nonyl, decyl, undecyl, tridecyl, pentadecyl and heptadecyl. The C1 to C10 alkyl refers to alkyl having a C1 to C10 alkyl unit, and when the C1 to C10 alkyl is substituted, the carbon number of a substituent is not included.

The term "aryl" refers to an entirely or partially unsaturated substituted or unsubstituted monocyclic or polycyclic carbon ring, for example, substituted or unsubstituted phenyl.

The term "arylalkyl" refers to alkyl substituted with an aryl group, and may be, for example, benzyl (phenylmethyl), phenylethyl or phenylpropyl. The aryl(C1 to C4)alkyl refers to C1 to C4 alkyl substituted with an aryl group. In Formula 1, $R_3$ may be C1 to C6, C1 to C4 or C1 to C2 alkyl.

In Formula 1, the alkyl of $R_3$ may be unsubstituted or substituted with a substituent such as C1 to C6 alkyl, a halo group, an aryl group, haloalkyl, a nitro group, a cyano group, an alkylthio group or an arylalkylthio group.

In Formula 1, when the alkyl of $R_3$ is substituted with a plurality of substituents, the substituents may be the same or different.

In Formula 1, n may be an integer of 0 to 4, 0 to 2 or 0 to 1. When n of Formula 1 is 0, it means that the compound is not substituted with $R_3$.

In Formula 1, $R_2$ may be hydrogen, C1 to C10 alkyl or aryl(C1 to C4)alkyl. In Formula 1, $R_2$ may be hydrogen, C1 to C6 alkyl or aryl(C1 to C2)alkyl.

In Formula 1, $R_2$ may be hydrogen, C1 to C6 alkyl, phenylmethyl or phenylethyl.

In Formula 1, the alkyl and arylalkyl of $R_2$ may be each independently unsubstituted or substituted with C1 to C6 alkyl, a halo group, an aryl group, haloalkyl, a nitro group, a cyano group, an alkylthio group or an arylalkylthio group.

In Formula 1, when the alkyl and/or arylalkyl of $R_2$ are(is) substituted with a plurality of substituents, the substituents may be the same or different.

In Formula 1, when $R_2$ is arylalkyl, an alkyl group, a halo group, a haloalkyl group, a cyano group, a nitro group or a phenyl group may be substituted at a para position.

In Formula 1, $R_4$ may be hydrogen, C1 to C4 alkyl, C3 to C8 cycloalkyl or aryl(C1 to C4)alkyl.

In Formula 1, $R_4$ may be hydrogen, C1 to C4 alkyl, C3 to C6 cycloalkyl or aryl(C1 to C2)alkyl.

In Formula 1, $R_4$ may be hydrogen, C1 to C2 alkyl, C5 to C6 cycloalkyl, phenylmethyl or naphthylmethyl.

The term "cycloalkyl" refers to a non-aromatic, saturated or partially unsaturated hydrocarbon ring, for example, the cycloalkyl may be monocyclic- or bicylcic.

In Formula 1, the alkyl, arylalkyl and cycloalkyl of $R_4$ may each be independently unsubstituted or substituted with a substituent such as a C1 to C6 alkyl, a halo group, an aryl group, haloalkyl, a nitro group, a cyano group, an alkylthio group or an arylalkylthio group. In Formula 1, when the alkyl, arylalkyl and/or cycloalkyl of $R_4$ are(is) substituted with a plurality of substituents, the substituents may be the same or different.

In Formula 1, when $R_4$ is alkyl, an alkylthio group or arylalkylthio group may be substituted.

For example, the alkylthio group may be a methylthio group, or an ethylthio group.

For example, the arylalkylthio group may be a phenylthio group or a benzylthio group.

In Formula 1, $R_2$ and $R_4$ may form a 4 to 7-membered ring, a 4 to 6-membered ring, or a 5 to 6-membered ring, and may be connected to each other. That is, $R_2$ and $R_4$ may be connected to form a tetragonal to heptagonal ring, a tetragonal to hexagonal ring, or a pentagonal to hexagonal ring.

The 4 to 7-membered ring in which $R_2$ and $R_4$ are connected may include 3 to 6 carbon atoms.

The 4 to 6-membered ring in which $R_2$ and $R_4$ are connected may include 3 to 5 carbon atoms.

The 5 to 6-membered ring in which $R_2$ and $R_4$ are connected may include 4 to 5 carbon atoms.

In Formula 1, $L_1$ may be directly bonded or may be C1 to C6, C1 to C4 or C1 to C2 alkylene.

The term "alkylene" refers to a bivalent residue derived from a linear or branched hydrocarbon chain, and may be, for example, a methylene group, an ethylene group, a propylene group, an isopropylene group, a n-butylene group, a sec-butylene group, a t-butylene group, an n-pentylene group, or an n-hexylene group.

The alkylene of $L_1$ may be unsubstituted or substituted with a substituent such as a C1 to C6 alkyl group, a halo group, an aryl group, a haloalkyl group, a nitro group, a cyano group, an alkylthio group or an arylalkylthio group. In Formula 1, when the alkylene of $L_1$ is substituted with a plurality of substituents, the substituents may be the same or different.

In Formula 1, n is an integer of 0 to 4; $R_1$ is hydrogen, C1 to C10 alkyl or aryl(C1 to C4)alkyl; $R_3$ is C1 to C6 alkyl, and when there are a plurality of the $R_3$, the $R_3$s may be the same or different; $L_1$ is a direct bond, or C1 to C6 alkylene; $R_2$ is hydrogen, C1 to C10 alkyl or aryl(C1 to C4)alkyl, and $R_4$ is hydrogen, C1 to C4 alkyl, C3 to C8 cycloalkyl or aryl(C1 to C4)alkyl, or $R_2$ and $R_4$ are connected to form a 4 to 7-membered ring; and the alkyl of $R_1$ to $R_4$, the arylalkyl of $R_1$, $R_2$ and $R_4$, the cycloalkyl of $R_4$, the alkylene of $L_1$ are each independently unsubstituted or substituted with a substituent such as a C1 to C6 alkyl group, a halo group, an aryl group, a haloalkyl group, a nitro group, a cyano group, an alkylthio group or an arylalkylthio group, and when the compound is substituted with a plurality of substituents, the substituents may be the same or different.

In Formula 1, n is an integer of 0 to 2; $R_1$ is hydrogen, C1 to C6 alkyl or aryl(C1 to C2)alkyl; $R_3$ is C1 to C6 alkyl, and when there are a plurality of the $R_3$, the $R_3$s are the same or different; $L_1$ is C1 to C4 alkylene; and $R_2$ is hydrogen, C1 to C6 alkyl or aryl(C1 to C2)alkyl, and $R_4$ is hydrogen, C1 to C4 alkyl, C3 to C6 cycloalkyl or aryl(C1 to C2)alkyl, or $R_2$ and $R_4$ are connected to form a 4 to 6-membered ring; and the alkyl of $R_1$ to $R_4$, the arylalkyl of $R_1$, $R_2$ and $R_4$, the cycloalkyl of $R_4$, and the alkylene of $L_1$ are each independently unsubstituted or substituted with a substituent such as a C1 to C6 alkyl group, a halo group, an aryl group, a haloalkyl group, a nitro group, a cyano group, an alkylthio group or an arylalkylthio group, and when the compound is substituted with a plurality of substituents, the substituents may be the same or different.

In Formula 1, n is an integer of 0 to 1; $R_1$ is hydrogen, C1 to C6 alkyl, phenylmethyl or phenylethyl; $R_3$ is C1 to C6 alkyl, and when there are a plurality of the $R_3$, the $R_3$s may be the same or different; $L_1$ is C1 to C2 alkylene; and $R_2$ is hydrogen, C1 to C6 alkyl, phenylmethyl or phenylethyl, $R_4$ is hydrogen, C1 to C2 alkyl, C5 to C6 cycloalkyl, phenylmethyl, phenylethyl or naphthylmethyl, or $R_2$ and $R_4$ are connected to form a 5 to 6-membered ring; the alkyl of $R_1$ to $R_4$, the phenylmethyl, phenylethyl and naphthylmethyl of $R_1$, $R_2$ and $R_4$, the cycloalkyl of $R_4$, and the alkylene of $L_1$ are each independently unsubstituted or substituted with a substituent such as a C1 to C6 alkyl group, a halo group, an aryl group, a haloalkyl group, a nitro group, a cyano group, an alkylthio group or an arylalkylthio group, and when the compound is substituted with a plurality of substituents, the substituents may be the same or different.

The compounds of Formula 1 may be Formula 2, Formula 5, Formulas 8 to 9, and Formulas 13 to 34 in Table 1 below.

TABLE 1

| Formula No. | Chemical Structure |
|---|---|
| 2 | 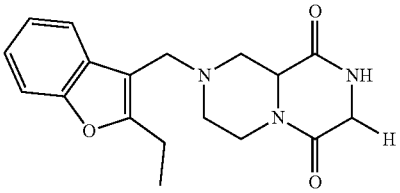 [SMILES: CCc1oc2ccccc2c1CN1CCN2C(=O)CNC(=O)C2C1] |
| 5 | 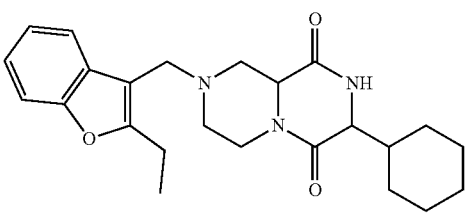 [SMILES: CCc1oc2ccccc2c1CN1CCN2C(=O)C(C3CCCCC3)NC(=O)C2C1] |
| 8 | 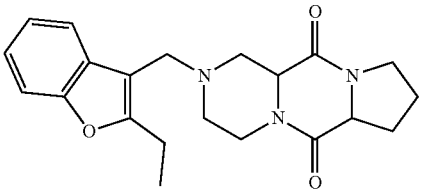 [SMILES: CCc1oc2ccccc2c1CN1CCN2C(=O)C3CCCN3C(=O)C2C1] |
| 9 | 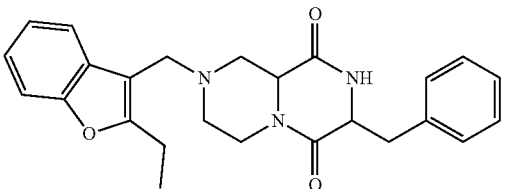 |

TABLE 1-continued
| Formula No. | Chemical Structure |
|---|---|
| 13 | 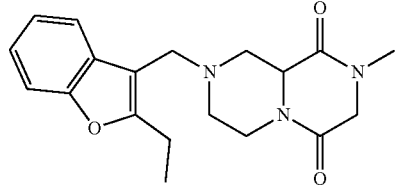 [SMILES: CCc1oc2ccccc2c1CN1CCN2C(=O)CN(C)C(=O)C2C1] |
| 14 | 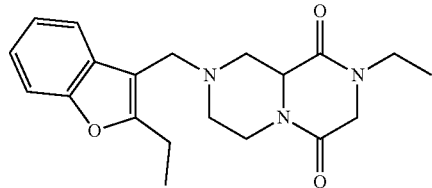 [SMILES: CCc1oc2ccccc2c1CN1CCN2C(=O)CN(CC)C(=O)C2C1] |
| 15 | 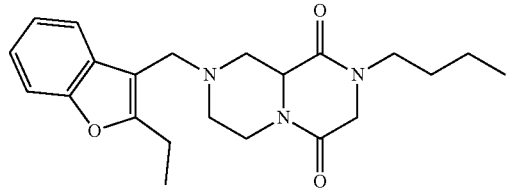 [SMILES: CCCCN1CC(=O)N2CCN(Cc3c(CC)oc4ccccc34)CC2C1=O] |
| 16 | 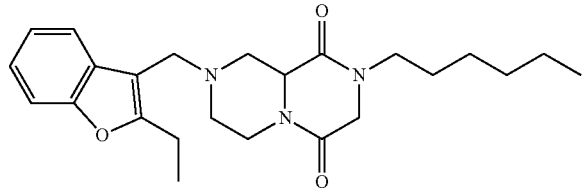 [SMILES: CCCCCCN1CC(=O)N2CCN(Cc3c(CC)oc4ccccc34)CC2C1=O] |
| 17 | 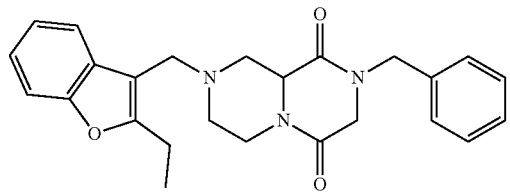 [SMILES: CCc1oc2ccccc2c1CN1CCN2C(=O)CN(Cc3ccccc3)C(=O)C2C1] |
| 18 | 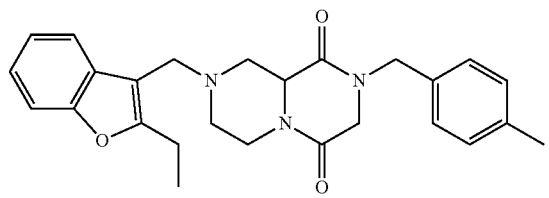 [SMILES: CCc1oc2ccccc2c1CN1CCN2C(=O)CN(Cc3ccc(C)cc3)C(=O)C2C1] |
| 19 | 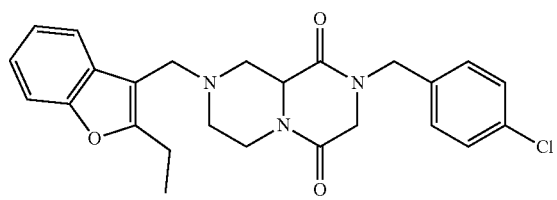 [SMILES: CCc1oc2ccccc2c1CN1CCN2C(=O)CN(Cc3ccc(Cl)cc3)C(=O)C2C1] |

TABLE 1-continued

| Formula No. | Chemical Structure |
|---|---|
| 20 | 2-(4-bromobenzyl)-8-((2-ethylbenzofuran-3-yl)methyl)hexahydro-2H-pyrazino[1,2-a]pyrazine-1,4-dione |
| 21 | 8-((2-ethylbenzofuran-3-yl)methyl)-2-(4-fluorobenzyl)hexahydro-2H-pyrazino[1,2-a]pyrazine-1,4-dione |
| 22 | 8-((2-ethylbenzofuran-3-yl)methyl)-2-(4-(trifluoromethyl)benzyl)hexahydro-2H-pyrazino[1,2-a]pyrazine-1,4-dione |
| 23 | 2-(4-cyanobenzyl)-8-((2-ethylbenzofuran-3-yl)methyl)hexahydro-2H-pyrazino[1,2-a]pyrazine-1,4-dione |
| 24 | 8-((2-ethylbenzofuran-3-yl)methyl)-2-(4-nitrobenzyl)hexahydro-2H-pyrazino[1,2-a]pyrazine-1,4-dione |
| 25 | 2-([1,1'-biphenyl]-4-ylmethyl)-8-((2-ethylbenzofuran-3-yl)methyl)hexahydro-2H-pyrazino[1,2-a]pyrazine-1,4-dione |
| 26 | 8-((2-ethylbenzofuran-3-yl)methyl)-2-phenethylhexahydro-2H-pyrazino[1,2-a]pyrazine-1,4-dione |

TABLE 1-continued
| Formula No. | Chemical Structure |
|---|---|
| 27 | 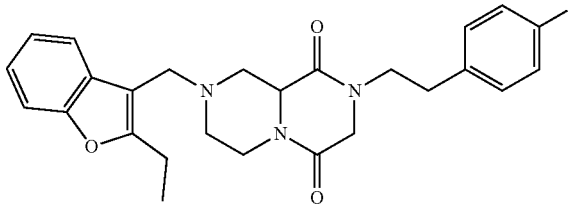 |
| 28 | 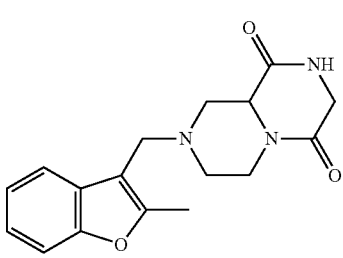 [SMILES: Cc1oc2ccccc2c1CN1CCN2C(=O)CNC(=O)C2C1] |
| 29 | 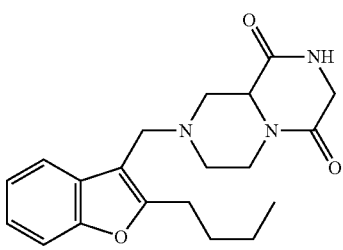 [SMILES: CCCCc1oc2ccccc2c1CN1CCN2C(=O)CNC(=O)C2C1] |
| 30 | 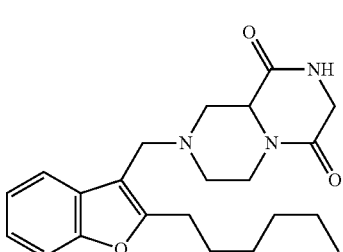 |
| 31 | 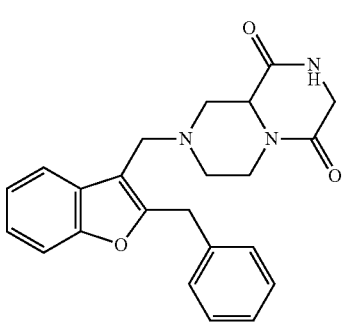 [SMILES: O=C1NCC(=O)N2CCN(Cc3c(Cc4ccccc4)oc4ccccc34)CC12] |

TABLE 1-continued

| Formula No. | Chemical Structure |
|---|---|
| 32 | *[structure: benzofuran with 4-chlorobenzyl substituent linked via CH2 to piperazine-2,5-dione bicyclic system]* |
| 33 | *[structure: benzofuran with 4-fluorobenzyl substituent linked via CH2 to piperazine-2,5-dione bicyclic system]* |
| 34 | *[structure: benzofuran with phenethyl substituent linked via CH2 to piperazine-2,5-dione bicyclic system]* |

The pharmaceutically acceptable salt may be, for example, an acid addition salt or metal salt.

The acid addition salt may be formed from an inorganic acid such as hydrochloric acid, nitric acid, phosphoric acid, sulfuric acid, hydrobromic acid, hydroiodic acid, nitrous acid or phosphorous acid, or non-toxic organic acids such as aliphatic mono or dicarboxylates, phenyl-substituted alkanoates, hydroxy alkanoates or alkandioates, aromatic acids, or aliphatic and aromatic sulfonic acids. The pharmaceutically non-toxic salt may be a sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1, 4-dioate, hexane-1,6-dioate, benzoate, chlorobenzoate, methylbenzoate, dinitrobenzoate, hydroxybenzoate, methoxybenzoate, phthalate, terephthalate, benzene sulfonate, toluene sulfonate, chlorobenzene sulfonate, xylenesulfonate, phenylacetate, phenylpropionate, phenylbutyrate, citrate, lactate, β_hydroxybutyrate, glycolate, malate, tartrate, methanesulfonate, propanesulfonate, naphthalene-1-sulfonate, naphthalene-2-sulfonate or mandelate. For example, the acid addition salt of the compound represented by Formula 1 may be obtained by dissolving the compound in an excessive amount of acid aqueous solution, and precipitating the salt using a hydrous organic solvent such as methanol, ethanol, acetone or acetonitrile.

The metal salt may be a sodium, potassium or calcium salt. The metal salt may be prepared using a base, an alkali metal or alkaline earth metal salt may be obtained by, for example, dissolving a compound in an excessive amount of an alkali metal hydroxide or alkali earth metal hydroxide solution, filtering a non-soluble compound salt, evaporating a filtrate, and/or drying the resulting product.

The above-described compound of Formula 1 and/or a pharmaceutically acceptable salt thereof may serve as an inhibitor of a SERCA protein responsible for survival signaling in ER stress signaling.

In addition, the present invention may provide a pharmaceutical composition for enhancing anticancer activity, which includes the above-described compound represented by Formula 1 or a pharmaceutically acceptable salt thereof.

The compound represented by Formula 1 or a pharmaceutically acceptable salt thereof is the same as described above.

The enhancement in anticancer activity may be enhancement in anticancer activity of an anticancer agent or radiation.

The composition of the present invention may improve effects of anticancer therapies such as chemotherapy using an anticancer agent, radiation therapy, or immunotherapy.

The "anticancer therapy" is a method for treating cancer, and may be, for example, surgical resection therapy, chemotherapy using an anticancer agent, radiation therapy or immunotherapy.

The term "treatment" refers to all actions involved in alleviating or beneficially changing symptoms in subjects suspected of having a disease and having a disease.

The composition of the present invention may be used as an anticancer adjuvant for anticancer therapy.

The anticancer agent may be at least one selected from the group consisting of a taxene-based anticancer agent and a camptothecin-based anticancer agent.

The taxene-based anticancer agent may be at least one selected from the group consisting of paclitaxel, docetaxel and cabazitaxel.

The camptothecin-based anticancer agent may be at least one selected from the group consisting of irinotecan, topotecan and velotecan.

The composition of the present invention may be a pharmaceutical composition for enhancing anticancer activity against resistant cancer.

The composition of the present invention may increase the susceptibility of cancer cells to anticancer therapy, and overcome the resistance of resistant cancer.

The term "increased susceptibility of cancer cells" means that the concentration showing effects of growth inhibition and cell death of cancer cells that have acquired resistance reaches the same level or more, compared with a concentration showing an effect of inhibiting the growth of cancer cells without resistance.

The term "resistant cancer" refers to cancer that does not show improvement, alleviation, reduction or treatment of cancer due to anticancer therapy. The resistant cancer may not have initial resistance to a specific anticancer therapy, or may also have resistance to the same therapy due to genetic mutations in cancer cells by long-term treatment without exhibiting initial resistance.

The resistant cancer may be cancer with resistance to radiation therapy by irradiation, that is, radiation-resistant cancer.

The resistant cancer may be cancer with resistance to chemotherapy using an anticancer agent, that is, anticancer agent-resistant cancer.

For example, the anticancer agent resistant cancer may be resistant cancer to at least one of a taxene-based anticancer agent and a camptothecin-based anticancer agent.

The resistant cancer to a taxene-based anticancer agent may be caused by the inhibition of a cancer cell death effect by a taxene-based anticancer agent due to a survival signaling protein such as NF-κB or GRP78. In this case, the pharmaceutical composition of the present invention inhibits the expression or activity of a survival signaling protein such as NF-κB or GRP78, thereby demonstrating that the resistance to a taxene-based anticancer agent is overcome.

The resistant cancer to a camptothecin-based anticancer agent may be generated by inhibition of the cancer cell death effect by a camptothecin-based anticancer agent due to a survival signaling protein such as PARP or NF-κB. In this case, the pharmaceutical composition of the present invention inhibits the expression or activity of the survival signaling protein such as PARP or NF-κB, thereby demonstrating that the resistance to a camptothecin-based anticancer agent is overcome.

The resistant cancer to the taxene-based anticancer agent and/or camptothecin-based anticancer agent may be generated by inhibiting a cancer cell death effect caused by the overexpression and/or excessive activation of a SERCA protein responsible for survival signaling in ER stress signaling. That is, as an inhibitor for the SERCA protein, the pharmaceutical composition of the present invention that can inhibit the expression or activity of the SERCA protein may overcome resistance to the taxene-based anticancer agent and/or the camptothecin-based anticancer agent.

The taxene-based anticancer agent and the camptothecin-based anticancer agent are the same as described above.

The resistant cancer may be at least one selected from the group consisting of thyroid cancer, stomach cancer, colorectal cancer, ovarian cancer, breast cancer, lung cancer, Kaposi's sarcoma, cervical cancer, pancreatic cancer, head and neck cancer, rectal cancer, colon cancer, esophageal cancer and prostate cancer. These may be cancers which have resistance to at least one of a taxene-based anticancer agent and a camptothecin-based anticancer agent.

The composition of the present invention may be co-administered with an anticancer agent, and in this case, may exhibit an anticancer adjuvant effect which overcomes resistance to an anticancer agent or radiation treatment.

The composition of the present invention may further include a compound represented by Formula 1 or a pharmaceutically acceptable salt thereof; and an anticancer agent.

Here, the additionally included anticancer agent may be at least one selected from the group consisting of nitrogen mustard, imatinib, oxaliplatin, rituximab, erlotinib, neratinib, lapatinib, gefitinib, vandetanib, nilotinib, semasanib, bosutinib, axitinib, macitinib, cediranib, restaurtinib, trastuzumab, gefitinib, bortezomib, sunitinib, pazopanib, toceranib, nintedanib, regorafenib, semaksanib, tibozanib, ponatinib, cabozantinib, carboplatin, sorafenib, renbatinib, bevacizumab, cisplatin, cetuximab, viscumalbum, asparaginase, tretinoin, hydroxycarbamide, dasatinib, estramustine, gemtuzumab ozogamycin, ibritumomab tucetan, heptaplastin, methylaminolevulinic acid, amsacriine, alemtuzumab, procarbazine, alprostadil, holmium nitrate, chitosa, gemcitabine, doxyfluridine, pemetrexed, tegapur, capecitabine, gimeracil, oteracil, azacitidine, methotrexate, uracil, cytarabine, 5-fluorouracil, fludagabine, enocitabine, flutamide, kefecitabine, decitabine, mercaptopurine, thioguanine, cladribine, carmofur, raltitrexed, docetaxel, paclitaxel, irinotecan, velotecan, topotecan, binorelbine, etoposide, vincristine, vinblastine, teniposide, doxorubicin, idarubicin, epirubicin, mitoxantrone, mitomycin, bleromycin, daunorubicin, dactinomycin, pararubicin, aclarubicin, pepromycin, temsirolimus, temozolomide, busulfan, ifosfamide, cyclophosphmide, melparan, altretmin, dacarbazine, thiotepa, bimustine, chlorambucil, mitoractol, leucovorin, tretonin, exnestane, aminoglutesimide, anagrelide, olaparib, navelbine, padrazol, tamoxifen, toremifen, testolactone, anastrozole, letrozole, borozole, bicalutamide, lomustine, vorinostat, entinostat and carmustine.

The composition of the present invention may further include at least one of a taxene-based anticancer agent and a camptothecin-based anticancer agent, in addition to the compound represented by Formula 1 or a pharmaceutically acceptable salt thereof.

For example, the composition of the present invention may further include at least one selected from the group consisting of paclitaxel, docetaxel and cabazitaxel.

For example, the composition of the present invention may further include at least one selected from the group consisting of irinotecan, topotecan and velotecan.

For example, the composition of the present invention may further include at least one selected from the group consisting of paclitaxel, docetaxel, cabazitaxel, irinotecan, topotecan and velotecan.

The composition of the present invention may further include another anticancer agent, in addition to the compound represented by Formula 1 or a pharmaceutically acceptable salt thereof; and the at least one of a taxene-based anticancer agent and a camptothecin-based anticancer agent.

Other than the taxene-based anticancer agent and the camptothecin-based anticancer agent, the additional anticancer agent may be at least one selected from the group consisting of nitrogen mustard, imatinib, oxaliplatin, rituximab, erlotinib, neratinib, lapatinib, gefitinib, vandetanib, nilotinib, semasanib, bosutinib, axitinib, macitinib, cediranib, restaurtinib, trastuzumab, gefitinib, bortezomib, sunitinib, pazopanib, toceranib, nintedanib, regorafenib, semaksanib, tibozanib, ponatinib, cabozantinib, carboplatin, sorafenib, renbatinib, bevacizumab, cisplatin, cetuximab, viscumalbum, asparaginase, tretinoin, hydroxycarbamide, dasatinib, estramustine, gemtuzumab ozogamycin, ibritumomab tucetan, heptaplastin, methylaminolevulinic acid, amsacriine, alemtuzumab, procarbazine, alprostadil, holmium nitrate, chitosa, gemcitabine, doxyfluridine, pemetrexed, tegapur, capecitabine, gimeracil, oteracil, azacitidine, methotrexate, uracil, cytarabine, 5-fluorouracil, fludagabine, enocitabine, flutamide, kefecitabine, decitabine, mercaptopurine, thioguanine, cladribine, carmofur, raltitrexed, docetaxel, paclitaxel, irinotecan, velotecan, topotecan, binorelbine, etoposide, vincristine, vinblastine, teniposide, doxorubicin, idarubicin, epirubicin, mitoxantrone, mitomycin, bleromycin, daunorubicin, dactinomycin, pararubicin, aclarubicin, pepromycin, temsirolimus, temozolomide, busulfan, ifosfamide, cyclophosphmide, melparan, altretmin, dacarbazine, thiotepa, bimustine, chlorambucil, mitoractol, leucovorin, tretonin, exnestane, aminoglutesimide, anagrelide, olaparib, navelbine, padrazol, tamoxifen, toremifen, testolactone, anastrozole, letrozole, borozole, bicalutamide, lomustine, vorinostat, entinostat and carmustine.

The composition of the present invention may exhibit a better anticancer activity enhancing effect by further including another anticancer agent, in addition to the compound represented by Formula 1 or a pharmaceutically acceptable salt thereof; and at least one of a taxene-based anticancer agent and a camptothecin-based anticancer agent.

The pharmaceutical composition of the present invention may include the compound represented by Formula 1 or a pharmaceutically acceptable salt thereof and the anticancer agent at a molar concentration ratio of 1:0.001 to 1:1000, 1:0.01 to 1:100, 1:0.1 to 1:50 or 1:0.1 to 1:20.

The pharmaceutical composition of the present invention may be prepared in the form of a capsule, tablet, a granule, an injection, an ointment, a powder or a drink.

The pharmaceutical composition of the present invention may be used by being formulated as an oral formulation such as a powder, granule, capsule, tablet, or an aqueous suspension, a preparation for external use, a suppository and an injection.

The pharmaceutical composition of the present invention may include a pharmaceutically acceptable carrier. The pharmaceutically acceptable carrier may be a binder, a lubricant, a disintegrant, an excipient, a solubilizer, a dispersant, a stabilizer, a suspending agent, a pigment or a favoring agent for oral administration, may be mixed with a buffer, a preservative, a pain-relieving agent, a solubilizer, an isotonic agent or a stabilizer for injection, or may be a base, an excipient, a lubricant, or a preservative for local administration.

The dosage form of the pharmaceutical composition of the present invention may be variously formed by being mixed with a pharmaceutically acceptable carrier. For example, for oral administration, the pharmaceutical composition of the present invention may be prepared in the form of a tablet, a troche, a capsule, an elixir, a suspension, a syrup or a wafer, and as an injectable form, may be prepared in a unit dosage ampoule or a multiple dosage form. In addition, the pharmaceutical composition of the present invention may be prepared as a solution, a suspension, a tablet, a capsule or a sustained release preparation.

The carrier, excipient and diluent for preparation may be lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oil, a filler, an anticoagulant, a lubricant, a wetting agent, a flavoring agent, an emulsifier or a preservative.

The administration route of the pharmaceutical composition of the present invention may be, but is not limited to, oral, intravenous, intramuscular, intraarterial, intramedullary, intrathecal, intracardiac, transdermal, subcutaneous, intraperitoneal, intranasal, intestinal, local, sublingual or rectal administration.

The pharmaceutical composition of the present invention may be orally or parenterally administered, and for parenteral administration, external use for skin, intraperitoneal injection, rectal injection, subcutaneous injection, intravenous injection, intramuscular injection or intrathoracic injection may be selected.

A dose of the pharmaceutical composition of the present invention may vary according to a patient's condition and body weight, the severity of a disease, a drug type, an administration route and administration duration, and may be suitably selected by those of ordinary skill in the art. For example, the pharmaceutical composition of the present invention may be administered daily at 0.0001 to 1,000 mg/kg or 0.001 to 500 mg/kg. The daily dose of the pharmaceutical composition of the present invention may be administered once or in divided portions. The dose may not limit the scope of the present invention in any way.

In addition, the present invention provides a use of the compound represented by Formula 1 or a pharmaceutically acceptable salt thereof to be used in treatment of resistant cancer.

The resistant cancer, the compound represented by Formula 1 or a pharmaceutically acceptable salt thereof is the same as described above, and detailed descriptions thereof will be omitted.

In addition, the present invention provides a method of treating cancer, which includes administering a therapeutically effective amount of the compound represented by Formula 1 or a pharmaceutically acceptable salt thereof to a target with resistant cancer.

The term "administration" refers to introduction of a predetermined material into a subject by a suitable method.

The resistant cancer, the compound represented by Formula 1 or a pharmaceutically acceptable salt thereof is the same as described above, and detailed descriptions thereof will be omitted.

The "subject with resistant cancer" refers to a subject in need of suitable treatment due to the occurrence of resistant cancer or the possibility thereof, and a subject who has received anticancer therapy, for example, surgical resection therapy, chemotherapy using an anticancer agent, radiation therapy or immunotherapy, but has resistance thereto and thus has the recurrence of cancer.

The subject with resistant cancer may be a human, a cow, a dog, a guinea pig, a rabbit, a chicken or an insect. In addition, the present invention provides a radiation treatment method, which includes: administering the compound represented by Formula 1 or a pharmaceutically acceptable salt thereof into a subject with resistant cancer; and treating radiation.

The resistant cancer, the subject with resistant cancer, the compound represented by Formula 1 or a pharmaceutically acceptable salt thereof are the same as described above, and detailed descriptions thereof will be omitted.

For radiation treatment, any conventional method for radiation treatment on cancer or a radiation treatment method on cancer, which will be developed in the future, may be applied.

When the administration of the compound represented by Formula 1 according to the present invention or a pharmaceutically acceptable salt thereof is used in combination with radiation treatment, a synergistic effect on the inhibition of the growth of cancer cells or cancer stem cells and./or induction of cell death may be provided, thereby not only preventing or treating cancer effectively, but also preventing resistance to radiation or the metastasis or recurrence of cancer.

Hereinafter, the present invention will be described in detail with reference to the following examples.

PREPARATION EXAMPLES

1. Preparation Example 1-1: C101, L19031

Through a 10-step reaction described below, 2-((2-ethylbenzofuran-3-yl)methyl)hexahydro-2H-pyrazino[1,2-a]pyrazine-6,9-dione(C101) was prepared. A synthesis method in each step will be described in detail.
1) Step 1

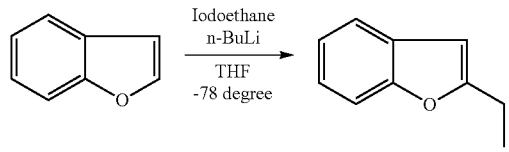

[Reaction Scheme 1]

As shown in Reaction Scheme 1, benzofuran (1.0 eq) was cooled in a tetrahydrofuran solvent to −78° C., and a 2.5M n-butyl lithium (1.2 eq) solution was added. The resulting solution was stirred for 1 hour while maintained at −78° C., and ethyl iodide (2.0 eq) was added dropwise, followed by stirring at 0° C. for 1 hour. The reaction completion was confirmed, and the reaction was terminated using an ammonium chloride aqueous solution and ethyl acetate. An organic layer was washed with distilled water, dried with anhydrous magnesium sulfate, and then concentrated under reduced pressure. The residual product was purified by silica chromatography, thereby obtaining 2-ethyl benzofuran.

2) Step 2

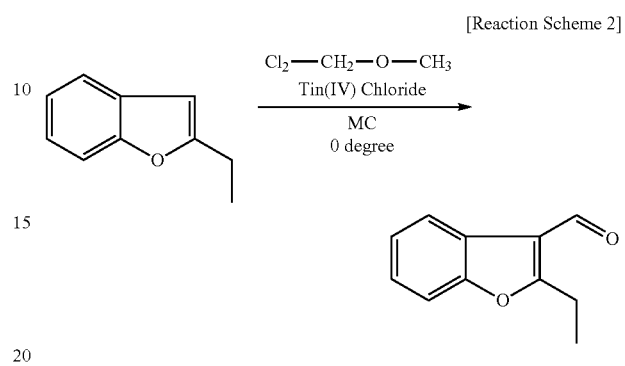

[Reaction Scheme 2]

2-ethyl benzofuran (1.0 eq) was added to methylene chloride (MC), cooled to 0° C., and tin(V) chloride (1.5 eq) and dichloromethyl methylether (1.5 eq) were sequentially added while maintaining 0° C., followed by stirring for 1 hour. The reaction completion was confirmed, and the reaction was terminated with an ammonium chloride aqueous solution and methylene chloride. An organic layer was washed with distilled water, dried with anhydrous magnesium sulfate, and concentrated under reduced pressure. The residual product was purified by silica chromatography, thereby obtaining 2-ethylbenzofuran-3-carbaldehyde.

3) Step 3

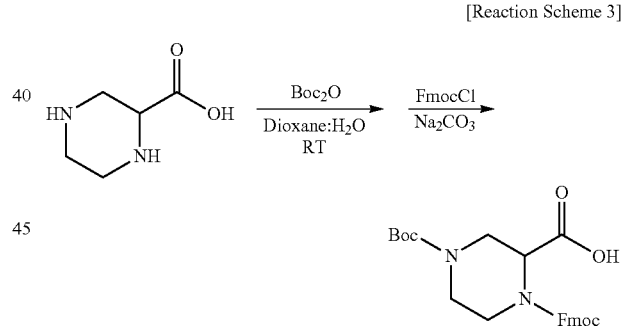

[Reaction Scheme 3]

Piperazine-2-carboxylic acid (1.0 eq), dioxane and distilled water were added, and then cooled to 5° C. or less. Afterward, di-tert-butyl dicarbonate (1.1 eq) was added while maintained at 10° C. or less. Following stirring at room temperature for 5 hours, sodium carbonate (1.1 eq) was added, and stirred for 5 minutes. 9-Fluorenylmethyl chloroformate (1.2 eq) was added, stirred overnight, and concentrated under reduced pressure. Ethyl acetate and 1M hydrochloric acid were added to the residual product to adjust a pH to 2 to 3, and vigorously stirred until the residual product was resuspended thoroughly. An organic layer was washed with brine, dried with anhydrous magnesium sulfate, and concentrated under reduced pressure. The resulting product with recrystallized with EA, thereby obtaining a white solid powder, 1-(((9H-fluoren-9-yl)methoxy)carbonyl)-4-(tert-butoxycarbonyl)piperazine-2-carboxylic acid.

4) Step 4

[Reaction Scheme 4]

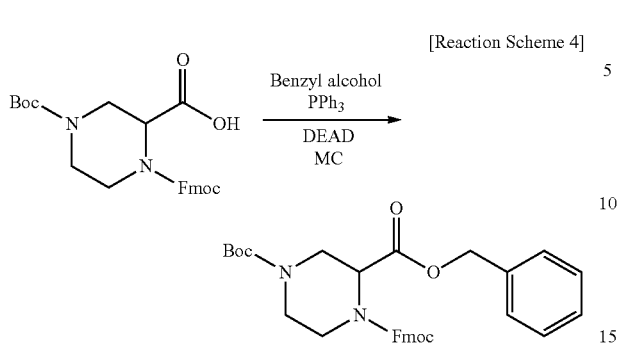

The 1-(((9H-fluoren-9-yl)methoxy)carbonyl)-4-(tert-butoxycarbonyl)piperazine-2-carboxylic acid was mixed with benzyl alcohol (1.02 eq) and triphenylphosphine (1.02 eq) in anhydrous methylene chloride, and the solution was cooled to 0° C. under a flow of nitrogen. Diethyl azodicarboxylate (DEAD; 1.02 eq) was added while maintaining 0° C. or less, and stirred for 1 hour. Water was added and then stirred vigorously for 20 minutes, and an organic layer was dried with anhydrous magnesium sulfate and concentrated under reduced pressure. The residual product was purified by silica chromatography, thereby obtaining a white solid powder, 1-((9H-fluoren-9-yl)methyl) 2-benzyl 4-(tert-butyl) piperazine-1,2,4-tricarboxylate.

5) Step 5

[Reaction Scheme 5]

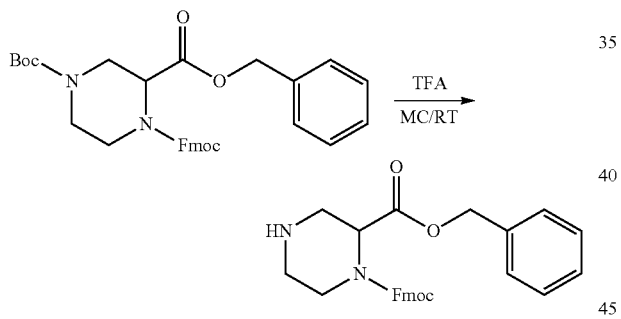

As shown in Reaction Scheme 5, trifluoroacetic acid (TFA) (2.0 vol.) was added to the 1-((9H-fluoren-9-yl)methyl) 2-benzyl 4-(tert-butyl) piperazine-1,2,4-tricarboxylate in a methylene chloride (5.0 vol.) solution at room temperature, and stirred at room temperature for 30 minutes. The resulting solution was neutralized with sodium bicarbonate and extracted with methylene chloride, and an organic layer was washed with brine. The resulting organic layer was dried with anhydrous magnesium sulfate and concentrated, thereby obtaining 1-((9H-fluoren-9-yl)methyl) 2-benzyl piperazine-1,2-dicarboxylate.

6) Step 6

[Reaction Scheme 6]

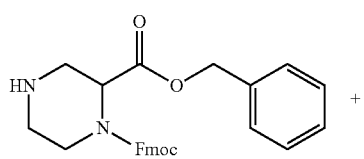 +

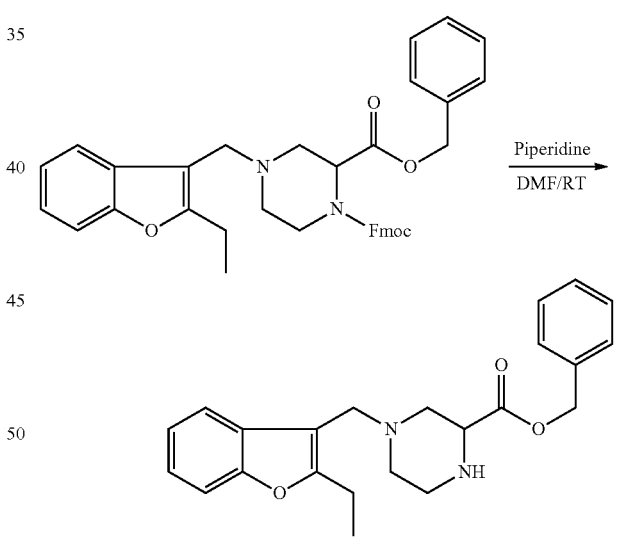

The 2-ethylbenzofuran-3-carbaldehyde (1.0 eq) obtained in Step 2 and the 1-((9H-fluoren-9-yl)methyl) 2-benzyl piperazine-1,2-dicarboxylate (1.2 eq) obtained in Step 5 were added to 1,2-dichloroethane (DCE) at room temperature, and stirred for 30 minutes. Sodium triacetoxyborohydride (3.0 eq) was added, and stirred overnight at room temperature. Methylene chloride and water were added to the reaction solution, and stirred vigorously for 20 minutes. A separated organic layer was washed with brine, dried with anhydrous magnesium sulfate and concentrated, thereby obtaining 1-((9H-fluoren-9-yl)methyl) 2-benzyl 4-((2-ethylbenzofuran-3-yl)methyl)piperazine-1,2-dicarboxylate.

7) Step 7

[Reaction Scheme 7]

The 1-((9H-fluoren-9-yl)methyl) 2-benzyl 4-((2-ethylbenzofuran-3-yl)methyl)piperazine-1,2-dicarboxylate (1.0 eq) was dissolved in dimethylformamide at room temperature, and piperidine (10 eq, 25% piperidine in solvent) was added, followed by stirring for 1 hour. Ethyl acetate was added to the reaction solution, and the piperidine in the solution was washed out with an ammonium chloride aqueous solution. The resulting product was dried with anhydrous magnesium sulfate and concentrated under reduced pressure. The residual product was purified by silica chromatography, thereby obtaining benzyl 4-((2-ethylbenzofuran-3-yl)methyl)piperazine-2-carboxylate.

8) Step 8

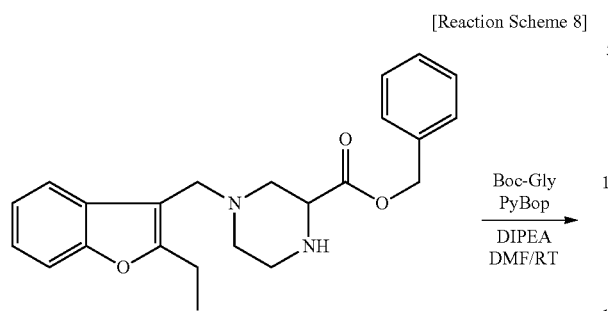

The benzyl 4-((2-ethylbenzofuran-3-yl)methyl)piperazine-2-carboxylate (1.0 eq) and N-(tert-butoxycarbonyl)glycine (1.1 eq), and (benzotriazol-1-yloxy)tripyrrolidinophosphonium hexafluorophosphate (1.2 eq) were dissolved in dimethylformamide at room temperature, and N,N-diisopropylethyl amine (1.5 eq) was added, followed by stirring overnight at room temperature. An ammonium chloride aqueous solution and ethyl acetate were used to terminate the reaction. The obtained organic layer was washed with brine, dried with anhydrous magnesium sulfate, and concentrated under reduced pressure. The residual product was purified by silica chromatography, thereby obtaining benzyl 1-((tert-butoxycarbonyl)glycyl)-4-((2-ethylbenzofuran-3-yl)methyl)piperazine-2-carboxylate.

9) Step 9

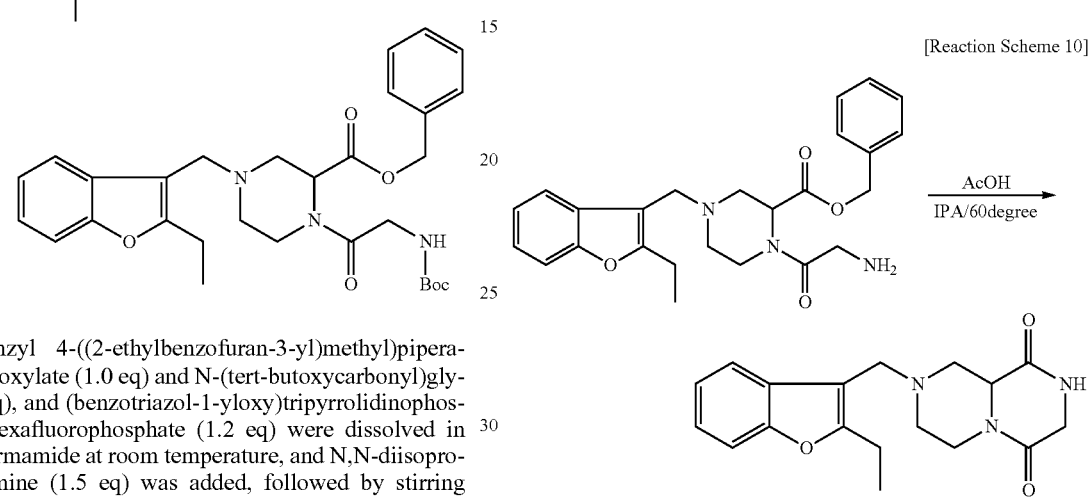

As shown in Reaction Scheme 9, the benzyl 1-((tert-butoxycarbonyl)glycyl)-4-((2-ethylbenzofuran-3-yl)methyl)piperazine-2-carboxylate obtained in Step 8 was dissolved in dichloromethane (5.0 vol.) at room temperature, and trifluoroacetic acid (2.0 vol.) was added, followed by stirring at room temperature for 30 minutes. After the completion of the reaction, a reaction solution was neutralized with a sodium bicarbonate aqueous solution, and extracted with methylene chloride. The resulting solution was dried with anhydrous magnesium sulfate and concentrated under reduced pressure, thereby obtaining benzyl 4-((2-ethylbenzofuran-3-yl)methyl)-1-glycylpiperazine-2-carboxylate.

10) Step 10

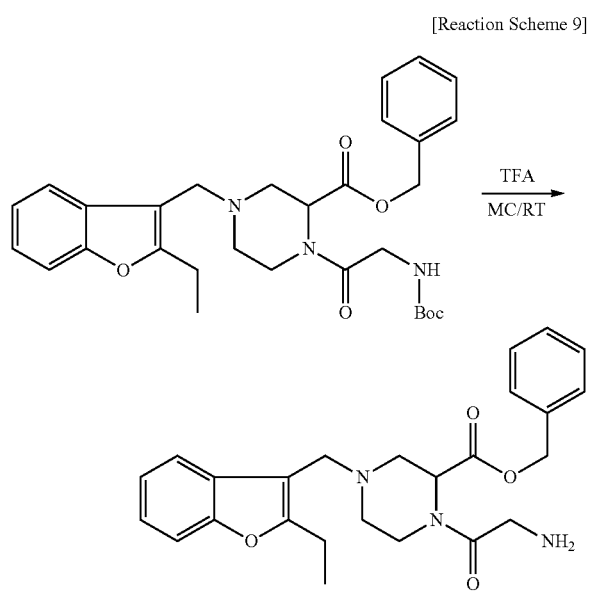

The benzyl 4-((2-ethylbenzofuran-3-yl)methyl)-1-glycylpiperazine-2-carboxylate obtained in Step 9 was dissolved in isopropanol (5.0 vol.), and acetic acid (1.5 vol.) was added, heated, and stirred for 1 hour. After the completion of the reaction, the resulting solution was neutralized with a sodium bicarbonate aqueous solution. A reaction product was extracted with methylene chloride, and dried with anhydrous magnesium sulfate. After concentration under reduced pressure, the residual product was purified by silica chromatography, thereby obtaining 2-((2-ethylbenzofuran-3-yl)methyl)hexahydro-2H-pyrazino[1,2-a]pyrazine-6,9-dione (Formula 2).

2-((2-ethylbenzofuran-3-yl)methyl)hexahydro-2H-pyrazino[1,2-a]pyrazine-6,9-dione (expressed as C101, L19031 or candidate 1).
1H-NMR (500 MHz, CDCl$_3$) δ7.58 (d, J=7.0 Hz, 1H), 7.40 (d, J=7.5 Hz, 1H), 7.24-7.17 (m, 2H), 4.50 (d, J=13.0 Hz, 1H), 4.06 (d, J=11.0 Hz, 1H), 4.00 (s, 2H), 3.64 (dd, J=57.5, 13.0 Hz, 1H), 3.47 (d, J=11.0 Hz, 1H), 2.90 (d, J=11.5 Hz, 1H), 2.71-2.81 (m, 3H), 2.11 (t, J=11.5 Hz, 1H), 2.07-2.01 (m, 1H), 1.30 (t, J=7.5 Hz, 3H);

$^{13}$C-NMR (126 MHz, CDCl$_3$) δ16632, 161.99, 158.34, 154.16, 129.60, 123.65, 122.56, 119.87, 110.94, 109.53, 57.18, 56.42, 51.84, 51.58, 44.75, 41.78, 20.18, 13.10; and MS (ESI) m/z for C$_{18}$H$_{21}$N$_3$O$_3$ [M+H]$^+$: calcd 328.1656, found 328.1655.

2. Preparation Example 1-2: C101·HCl, L19001

A hydrochloric acid salt of Formula 3 was prepared by the same method as in Preparation Example 1-1, except that hydrochloric acid was used at the end of the above-described Preparation Example 1-1.

[Formula 3]

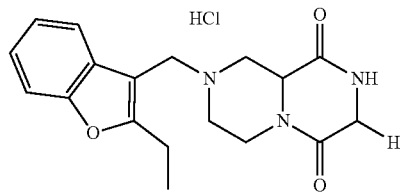

2-((2-ethylbenzofuran-3-yl)methyl)hexahydro-2H-pyrazino[1,2-a]pyrazine-6,9-dione hydrochloride (expressed as C101·HCl or L19001).

3. Preparation Example 2: C102, L19002

A hydrochloric acid salt of Formula 4 was prepared by the same method as in Preparation Example 1-1, except that N-(tert-butoxycarbonyl)-L-alanine was used instead of N-(tert-butoxycarbonyl)glycine, which is a reaction material used in Step 8 of the above-described Preparation Example 1-1, and hydrochloric acid was used at the end of Preparation Example 1-1.

[Formula 4]

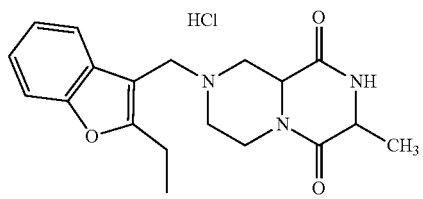

2-((2-ethylbenzofuran-3-yl)methyl)-7-methylhexahydro-2H-pyrazino[1,2-a]pyrazine-6,9-dione hydrochloride (expressed as C102 or L19002).

$^1$H-NMR (500 MHz, CD$_3$OD) δ7.78-7.72 (m, 1H), 7.53-7.47 (m, 1H), 7.36-7.29 (m, 2H), 4.69 (dd, J=21.3, 12.3 Hz, 1H), 4.60-4.46 (m, 3H), 4.13 (dq, J=13.8, 6.8 Hz, 1H), 3.99-3.91 (m, 1H), 3.66 (s, 1H), 3.20-3.02 (m, 3H), 2.98 (dq, J=7.5, 2.0 Hz, 2H), 1.46 (t, J=7.5 Hz, 3H), 1.38 (t, J=7.5 Hz, 3H);

MS (ESI) m/z for C$_{19}$H$_{23}$N$_3$O$_3$ [M+H]$^+$: calcd 342.1812, found 342.1813.

4. Preparation Example 3: C105, L19033

A compound of Formula 5 was obtained by the same method as in Preparation Example 1-1, except that N-(tert-butoxycarbonyl)-L-2-cyclohexylglycine was used instead of N-(tert-butoxycarbonyl)glycine, which is a reaction material used in Step 8 of the above-described Preparation Example 1-1.

[Formula 5]

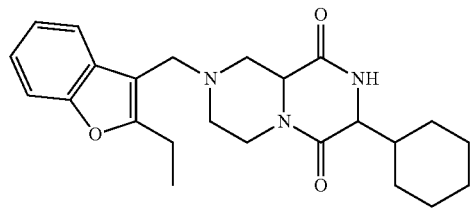

7-cyclohexyl-2-((2-ethylbenzofuran-3-yl)methyl)hexahydro-2H-pyrazino[1,2-a]pyrazine-6,9-dione (expressed as C105 or L19033).

$^1$H-NMR (500 MHz, CDCl$_3$) δ7.59 (d, J=7.5 Hz, 1H), 7.40 (d, J=7.5 Hz, 1H), 7.23-7.17 (m, 2H), 4.53 (t, J=12.3 Hz, 1H), 4.06 (ddd, J=20.0, 11.0, 3.0 Hz, 1H), 3.87 (d, J=28.0 Hz, 1H), 3.70 (dd, J=13.0, 5.5 Hz, 1H), 3.58-3.49 (m, 2H), 2.90 (d, J=11.5 Hz, 1H), 2.78 (q, J=7.5 Hz, 2H), 2.75-2.65 (m, 1H), 2.15-1.93 (m, 4H), 1.83-1.60 (m, 4H), 1.48 (dd, J=32.5, 12.0 Hz, 1H), 1.34-1.26 (m 4H), 1.28-1.04 (m, 3H);

$^{13}$C-NMR (126 MHz, CDCl$_3$) δ167.02, 166.42, 165.05, 163.54, 158.33, 158.27, 154.16, 129.62, 129.57, 128.75, 127.80, 127.19, 123.64, 123.63, 122.54, 119.90, 119.87, 110.91, 109.63, 109.57, 6034, 59.95, 57.52, 5709, 56.57, 56.50, 51 98, 51.89, 51.78, 51.54, 43.67, 42.11, 41.95, 41.52, 29.49, 29.30, 26.78, 26.56, 26.53, 26.39, 26.08, 25.98, 25.87, 20.16, 13.11, 13.10;

MS (ESI) m/z for C$_{24}$H$_{31}$N$_3$O$_3$ [M+H]$^+$: calcd 410.2438, found 410.2442.

5. Preparation Example 4: C107, L19003

A hydrochloric acid salt of Formula 6 was prepared by the same method as in Preparation Example 1-1, except that N-(tert-butoxycarbonyl)-L-methionine was used instead of N-(tert-butoxycarbonyl)glycine, which is a reaction material used in Step 8 of the above-described Preparation Example 1-1, and hydrochloric acid was used at the end of the process.

[Formula 6]

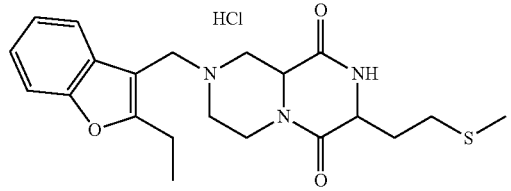

2-((2-ethylbenzofuran-3-yl)methyl)-7-(2-(methylthio)ethyl)hexahydro-2H-pyrazino[1,2-a]pyrazine-6,9-dione hydrochloride (expressed as C107 or L19003).

$^1$H-NMR (500 MHz, CD$_3$OD) δ7.80-7.76 (m, 1H), 7.50-7.47 (m, 1H), 7.34-7.30 (m, 2H), 4.72-4.57 (m, 4H), 4.25-4.21 (m, 1H), 4.00 (t, J=9.8 Hz, 1H), 3.70 (s, 1H), 341-3.32 (m, 1H), 3.24-3.07 (m, 2H), 3.00 (dq, J=11.0, 3.9 Hz, 2H), 2.64-2.50 (m, 2H), 2.28-2.18 (m, 1H), 2.14-2.06 (m, 1H), 2.00 (d, J=22.5 Hz, 3H), 1.38 (dt, J=7.5, 3.5 Hz, 3H);

6. Preparation Example 5: C108, L19004

A hydrochloric acid salt of Formula 7 was prepared by the same method as in Preparation Example 1-1, except that N-(tert-butoxycarbonyl)-S-benzyl-L-cysteine was used instead of N-(tert-butoxycarbonyl)glycine, which is a reaction material used in Step 8 of the above-described Preparation Example 1-1, and hydrochloric acid was used at the end of the process.

[Formula 7]

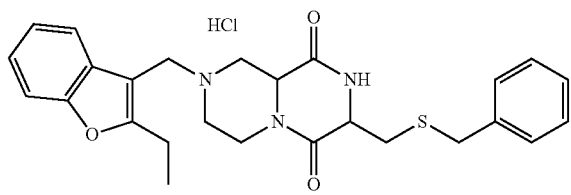

7-((benzylthio)methyl)-2-((2-ethylbenzofuran-3-yl)methyl)hexahydro-2H-pyrazino[1,2-a]pyrazine-6,9-dione hydrochloride (expressed as C108 or L19004).

$^1$H-NMR (500 MHz, CD$_3$OD) δ7.78-7.69 (m, 1H), 7.49-7.46 (m, 1H), 7.29-7.26 (m, 7H), 4.70-4.64 (m, 1H), 4.59 (s, 1H), 4.53-4.39 (m, 2H), 4.36-4.32 (m, 1H), 3.94 (d, J=10.5 Hz, 1H), 3.71 (d, J=2.5 Hz, 1H), 3.51 (dd, J=42.0, 13.2 Hz, 2H), 3.09 (dd, J=14.5, 4.0 Hz, 2H), 3.03 (dd, J=14.5, 3.5 Hz, 1H), 2.99-2.88 (m, 2H), 2.80 (ddd, J=35.5, 14.5, 3.8 Hz, 2H), 1.36 (dt, J=12.0, 7.5 Hz, 3H);

MS (ESI) m/z for C$_{26}$H$_{29}$N$_3$O$_3$S [M+H]$^+$: calcd 464.2002, found 464.2001.

7. Preparation Example 6: C109, L19035

A compound of Formula 8 was prepared by the same method as in Preparation Example 1-1, except that N-(tert-butoxycarbonyl)-L-proline was used instead of N-(tert-butoxycarbonyl)glycine, which is a reaction material used in Step 8 of the above-described Preparation Example 1-1.

[Formula 8]

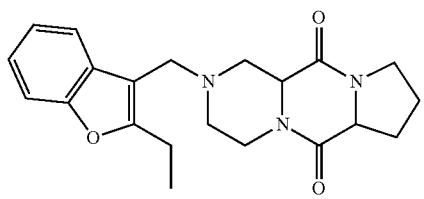

2-((2-ethylbenzofuran-3-yl)methyl)octahydro-6H-pyrazino[1,2-a]pyrrolo[1,2-d]pyrazine-6,11(2H)-dione (expressed as C109 or L19035).

$^1$H-NMR (500 MHz, CDCl$_3$) δ7.58 (dd, J=13, 0, 7.5 Hz, 1H), 7.39 (d, J=8.0 Hz, 1H), 7.24-7.15 (m, 2H), 4.45 (dd, J=59.0, 13.0 Hz, 1H), 4.13-3.98 (m, 2H), 3.81-3.66 (m, 2H), 3.62-3.37 (m, 3H), 2.96-2.71 (m, 4H), 2.48-2.40 (m, 1H), 2.15-1.82 (m, 5H), 1.30 (dt, J=16.0, 8.0 Hz, 3H);

$^{13}$C-NMR (126 MHz, CDCl$_3$) δ167.19, 164.43, 163.30, 162.81, 158.31, 158.30, 154.16, 154.13, 129.66, 129.62, 123.63, 123.56, 122.58, 122.48, 119.97, 119.85, 110.90, 110.87, 109.75, 109.49, 61.16, 59.10, 58.76, 57.14, 56.28, 55.82, 52.01, 51.91, 51.67, 51.43, 45.51, 45.42, 42.04, 41.75, 31.82, 30.15, 29.96, 22.89, 22.07, 21.92, 20.19, 20.17, 14.37, 13.10;

MS (ESI) m/z for C$_{21}$H$_{25}$N$_3$O$_3$ [M+H]$^+$: calcd 368.1969, found 368.1974.

8. Preparation Example 7-1: C111, L19037

A compound of Formula 9 was prepared by the same method as in Preparation Example 1-1, except that N-(tert-butoxycarbonyl)-L-phenylalanine was used instead of N-(tert-butoxycarbonyl)glycine, which is a reaction material used in Step 8 of the above-described Preparation Example 1-1.

[Formula 9]

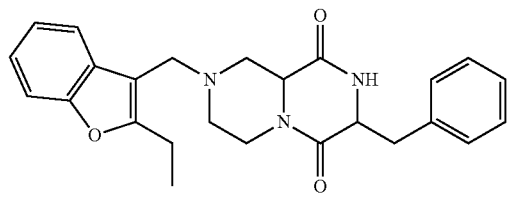

7-benzyl-2-((2-ethylbenzofuran-1-yl)methyl) hexahydro-2H-pyrazino[1,2-a]pyrazine-6,9-dione (expressed as C111 or L19037).

$^1$H-NMR (500 MHz, CDCl$_3$) δ7.49 (dd, J=12.5, 7.5 Hz, 1H), 740 (dd, J=80, 5.0 Hz, 1H), 7.34-7.16 (m, 7H), 4.46 (dd, J=39.5, 13.0 Hz, 1H), 4.34 (d, J=26.5 Hz, 1H), 3.83 (dd, J=10.5, 2.5 Hz, 0.5H), 3.55 (dd, J=62.5, 13.5 Hz, 1H), 339 (s, 1H), 3.35 (dd, J=13.5, 4.0 Hz, 0.5H), 3.30-3.21 (m, 1H), 3.04 (dd, J=13.5, 4.0 Hz, 0.5H), 2.97 (dd, J=13.5, 4.0 Hz, 1H), 2.86-2.79 (m, 1H), 2.76-2.69 (m, 3H), 2.59 (dd, J=12.5, 3.0 Hz, 0.5H), 2.44 (dd, J=12.5, 3.5 Hz, 0.5H), 1.97-1.90 (m, 1H), 1.69 (dd, J=12.0, 3.0 Hz, 0.5H), 1.28 (dt, J=7.5, 7.5 Hz, 3H);

$^{13}$C-NMR (126 MHz, CDCl$_3$) δ167.02, 166.39, 164.80, 162.84, 158.28, 158.19, 154.13, 135.21, 135.03, 131.16, 130.32, 129.69, 129.63, 128.89, 12879, 127.89, 127.52, 123.63, 123.59, 122.53, 122.48, 119.88, 119.82, 110.90, 110.88, 109.58, 109.43, 57.62, 56.35, 56.12, 55.96, 55.91, 55.32, 51.77, 51.40, 51.34, 51.30, 41.08, 41.4, 40.73, 20.16, 20.10, 13.10, 13.07;

MS (ESI) m/z for C$_{25}$H$_{27}$N$_3$O$_3$ [M+H]$^+$: calcd 418.2125, found 418.2129.

9. Preparation Example 7-2: C111·HCl, L19005

A hydrochloric acid salt of Formula 10 was prepared by the same method as in Preparation Example 7-1, except that hydrochloric acid was used at the end of the above-described Preparation Example 7-1.

[Formula 10]

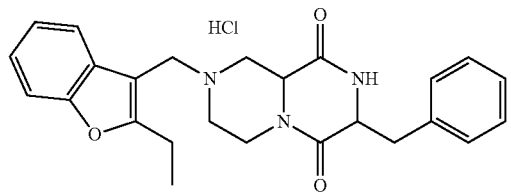

7-benzyl-2-((2-ethylbenzofuran-3-yl)methyl)hexahydro-2H-pyrazino[1,2-a]pyrazine-6,9-dione hydrochloride (expressed as C111·HCl or L19005).

10. Preparation Example 8: C121, L19006

A hydrochloric acid salt of Formula 11 was prepared by the same method as in Preparation Example 1-1, except that N-(tert-butoxycarbonyl)-3-(1-naphthyl)-D-alanine was used instead of N-(tert-butoxycarbonyl)glycine, which is a reaction material used in Step 8 of the above-described Preparation Example 1-1, and hydrochloric acid was used at the end of the process.

[Formula 11]

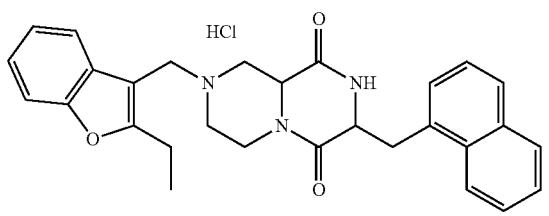

2-((2-ethylbenzofuran-3-yl)methyl)-7-(naphthalen-1-yl-methyl)hexahydro-2H-pyrazino[1,2-a]pyrazine-6,9-dione hydrochloride (expressed as C121 or L19006).

$^1$H-NMR (500 MHz, CD$_3$OD) δ8.07 (dd, J=18.8, 8.5 Hz, 1H), 7.84 (dd, J=12.8, 8.0 Hz, 1H), 7.64-7.21 (m, 9H), 4.59 (s, 1H), 4.50-4.43 (m, 1H), 4.40 (d, J=14.0 Hz, 0.5H), 4.23 (bs, 1H), 4.18 (d, J=14 Hz, 0.5H), 4.02 (d, J=11.5 Hz, 0.5H), 3.90 (dd, J=14.0, 3.0 Hz, 0.5H), 3.81 (bs, 1H), 3.74 (dd, J=14.0, 4.0 Hz, 0.5H), 3.54-3.49 (m, 1H), 3.36-3.20 (m, 1H), 3.09 (dd, J=29.0, 11.5 Hz, 1H), 2.86-2.70 (m, 3.5H), 2.57 (d, J=11.0 Hz, 0.5H), 2.17-2.08 (m, 0.5H), 1.31 (dt, J=17.5, 7.5 Hz, 3H); and MS (ESI) m/z for C$_{29}$H$_{29}$N$_3$O$_3$ [M+H]$^+$: calcd 468.2282, found 468.2284.

11. Preparation Example 9: C122, L19007

A hydrochloric acid salt of Formula 12 was prepared by the same method as in Preparation Example 1-1, except that N-(tert-butoxycarbonyl)-3-(2-naphthyl)-D-alanine was used instead of N-(tert-butoxycarbonyl)glycine, which is a reaction material used in Step 8 of the above-described Preparation Example 1-1, and hydrochloric acid was used at the end of the process.

[Formula 12]

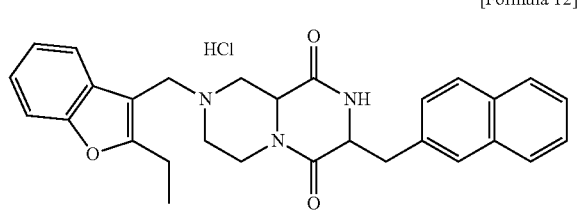

2-((2-ethylbenzofuran-3-yl)methyl)-7-(naphthalen-2-yl-methyl)hexahydro-2H-pyrazino[1,2-a]pyrazine-6,9-dione hydrochloride (expressed as C122 or L19007).

$^1$H-NMR (500 MHz, CD$_3$OD) δ8.00-7.15 (m, 11H), 4.64 (d, J=15.0 Hz, 1H), 4.59 (s, 1H), 4.52-4.45 (m, 1H), 4.42 (s, 1H), 4.19 (d, J=10.5 Hz, 0.5H), 3.65-3.33 (m, 3.5H), 3.27 (d, J=11 Hz, 0.5H), 3.19-3.06 (m, 2H), 2.96-2.82 (m, 2H), 2.64-2.52 (m, 1.5H), 2.14 (dt, J=12.5, 3.0 Hz, 0.5H), 2.14 (dt, J=12.5, 3.0 Hz, 0.5H) 1.27 (dt, J=27.0, 7.5 Hz, 3H); and MS (ESI) m/z for C$_{29}$H$_{29}$N$_3$O$_3$ [M+H]$^+$: calcd 468.2282, found 468.2283.

12. Preparation Example 10: C201, L19008

A compound of Formula 13 was obtained by further performing the step shown in Reaction Scheme 11 below using the compound (Formula 2) obtained in Preparation Example 1-1 as a starting material.

[Reaction Scheme 11]

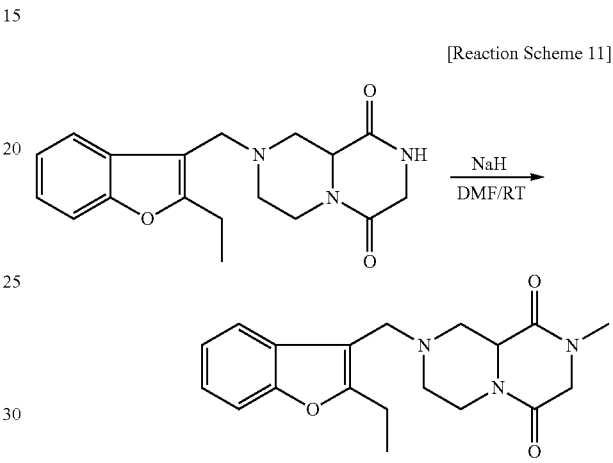

2-((2-ethylbenzofuran-3-yl)methyl)hexahydro-2H-pyrazino[1,2-a]pyrazine-6,9-dione, sodium hydride (2.0 eq) and dimethylformamide were added at room temperature, stirred for 1 hour, and then methyl iodide was added and stirred overnight at room temperature. The reaction was confirmed by TLC, and then terminated with an ammonium chloride aqueous solution and ethyl acetate. An organic layer was washed with an aqueous solution, dried with anhydrous magnesium sulfate, and concentrated under reduced pressure. The residual product was purified by silica chromatography, thereby obtaining 2-((2-ethylbenzofuran-3-yl)methyl)-8-methylhexahydro-2H-pyrazino[1,2-a]pyrazine-6,9-dione.

[Formula 13]

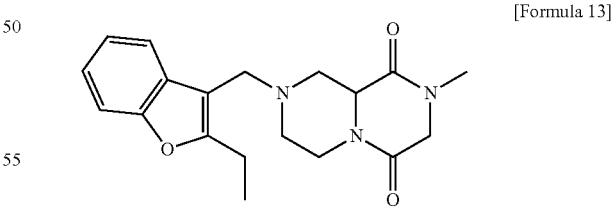

2-((2-ethylbenzofuran-3-yl)methyl)-8-methyl hexahydro-2H-pyrazino[1,2-a]pyrazine-6,9-dione (expressed as C201 or L19008).

$^1$H-NMR (500 MHz, CDCl$_3$) δ7.59 (d, J=7.0 Hz, 1H), 7.40 (d, J=7.5 Hz, 1H), 7.25-7.16 (m, 2H), 4.49 (d, J=13.0 Hz, 1H), 4.09-4.03 (m, 1H), 3.97-3.96 (m, 2H), 3.78-3.50 (m, 3H), 2.95 (s, 3H), 2.89 (d, J=11.5 Hz, 1H), 2.80-2.70 (m, 3H), 2.11-1.99 (m, 2H), 130 (t, J=7.5 Hz, 3H), $^{13}$C-NMR (126 MHz, CDCl$_3$) δ163.73, 161.65, 158.36, 154.15, 129.62, 123.62, 122.56, 119.88, 110.91, 109.49, 57.45, 5685, 51 76, 51.43, 51.40, 41.56, 33.62, 20.18, 13.08; and MS (ESI) m/z for $C_{19}H_{23}N_3O_3$ [M+H]$^+$: calcd 342.1812, found 342.1802.

13. Preparation Example 11: C202, L19009

A compound of Formula 14 was obtained by the same method as in Preparation Example 10, except that ethyl iodide was used instead of methyl iodide, which is a reaction material.

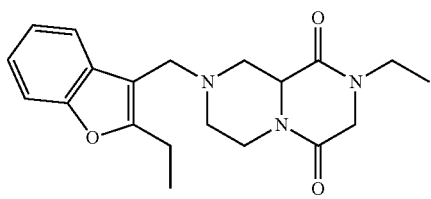

[Formula 14]

8-ethyl-2-((2-ethylbenzofuran-3-yl)methyl)hexahydro-2H-pyrazino[1,2-a]pyrazine-6,9-dione (expressed as C202 or L19009).

$^1$H-NMR (500 MHz, CDCl$_3$) δ7.59 (d, J=7.5 Hz, 1H), 740 (d, J=7.5 Hz, 1H), 7.23-7.16 (m, 2H), 4.48 (d, J=13.0 Hz, 1H), 4.07-4.03 (m, 1H), 4.01-3.91 (m, 2H), 3.72 (d, J=13.5 Hz, 1H), 3.59-3.52 (m 2H), 3.50-3.35 (m, 2H), 2.88 (d, J=11.5 Hz, 1H), 2.81-2.70 (m, 3H), 2.08 (t, J=11.5 Hz, 1H), 2.02 (dt, J=11.5, 3.0 Hz, 1H), 130 (t, J=7.5 Hz, 3H), 1.15 (t, J=7.3 Hz, 3H);

$^{13}$C-NMR (126 MHz, CDCl$_3$) δ163.20, 162.05, 158.29, 154.15, 129.63, 123.60, 122.53, 119.90, 110.89, 109.60, 57.54, 56.89, 51.81, 51.39, 48.81, 41.59, 41.12, 2018, 13.08, 11.83; and MS (ESI) m/z for $C_{20}H_{25}N_3O_3$ [M+H]$^+$: calcd 356.1969, found 356.1955.

14. Preparation Example 12: C203, L19010

A compound of Formula 15 was obtained by the same method as in Preparation Example 10, except that butyl bromide was used instead of methyl iodide, which is a reaction material.

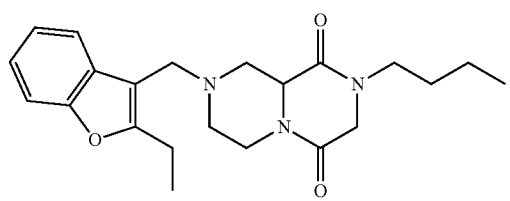

[Formula 15]

8-butyl-2-((2-ethylbenzofuran-3-yl)methyl)hexahydro-2H-pyrazino[1,2-a]pyrazine-6,9-dione (expressed as C203 or L19010).

$^1$H-NMR (500 MHz, CDCl$_3$) δ7.59 (d, J=7.5 Hz, 1H), 7.39 (d, J=8.0 Hz, 1H), 7.24-7.16 (m, 2H), 4.48 (d, J=13.0 Hz, 1H), 4.06 (d, J=11.0 Hz, 1H), 3.95 (d, J=4.5 Hz, 2H), 372 (d, J=13.0 Hz, 1H), 3.60-3.52 (m, 2H), 3.37 (t, J=7.5 Hz, 2H), 2.88 (d, J=11.5 Hz, 1H), 2.80-2.69 (m, 3H), 2.07 (t, J=11.5 Hz, 1H), 2.02 (dt, J=11.5, 3.3 Hz, 1H), 1.57-1.49 (m, 2H), 1.36-1.28 (m, 5H), 0.93 (t, J=7.3 Hz, 3H);

$^{13}$C-NMR (126 MHz, CDCl$_3$) δ163.43, 162.09, 158.28, 154.15, 129.63, 123.59, 122.52, 119.90, 110.88, 109.59, 57.52, 56.94, 51.80, 51.38, 49.34, 45.97, 41.59, 28.63, 20.17, 20.12, 13.95, 13.07; and MS (ESI) m/z for $C_{22}H_{29}N_3O_3$ [M+H]$^+$: calcd 384.2282, found 384.2260.

15. Preparation Example 13: C204, L19011

A compound of Formula 16 was obtained by the same method as in Preparation Example 10, except that hexyl bromide was used instead of methyl iodide, which is a reaction material.

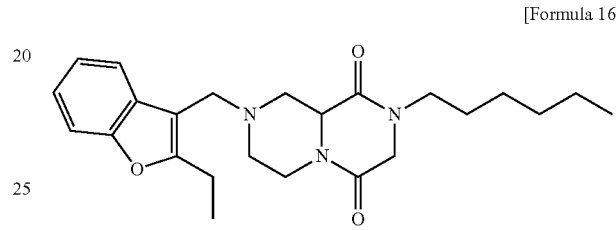

[Formula 16]

2-((2-ethylbenzofuran-3-yl)methyl)-8-hexylhexahydro-2H-pyrazino[1,2-a]pyrazine-6,9-dione (expressed as C204 or L19011).

$^1$H-NMR (500 MHz, CDCl$_3$) δ7.59 (d, J=7.5 Hz, 1H), 7.40 (d, J=8.0 Hz, 1H), 7.24-7.16 (m, 2H), 448 (d, J=13.0 Hz, 1H), 4.06 (d, J=11.0 Hz, 1H), 3.96 (d, J=5.0 Hz, 2H), 3.72 (d, J=13.5 Hz, 1H), 3.59-3.52 (m, 2H), 3.37 (dd, J=8.8, 6.8 Hz, 2H), 2.88 (d, J=11.0 Hz, 1H), 2.81-2.70 (m, 3H), 2.07 (t, J=11.0 Hz, 1H), 2.02 (dd, J=3.5, 11.5, Hz, 1H), 1.57-1.50 (m, 2H), 1.32-1.26 (t, J=6.1 Hz, 9H), 0.88 (t, J=7.0 Hz, 3H);

$^{13}$C-NMR (126 MHz, CDCl$_3$) δ163.41, 162.11, 158.30, 154.16, 129.63, 123.60, 122.53, 119.89, 110.89, 109.58, 57.53, 56.95, 51.81, 51.38, 49.36, 46.25, 41.60, 31.63, 26.55, 26.52, 22.73, 20.17, 14.22, 13.07; and MS (ESI) m/z for $C_{24}H_{33}N_3O_3$[M+H]$^+$: calcd 412.2595, found 412.2566.

16. Preparation Example 14: C206, L19012

A compound of Formula 17 was obtained by the same method as in Preparation Example 10, except that benzyl bromide was used instead of methyl iodide, which is a reaction material.

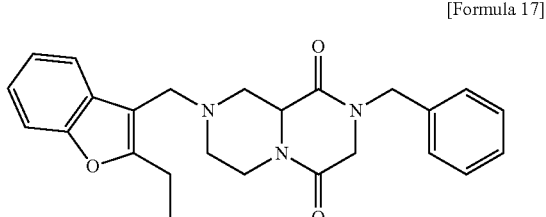

[Formula 17]

8-benzyl-2-((2-ethylbenzofuran-3-yl)methyl)hexahydro-2H-pyrazino[1,2-a]pyrazine-6,9-dione (expressed as C206 or L19012).

$^1$H-NMR (500 MHz, CDCl$_3$) δ7.60 (d, J=7.0 Hz, 1H), 7.40 (d, J=7.5 Hz, 1H), 7.36-7.29 (m, 3H), 7.26-7.17 (m, 4H), 4.57 (q, J=14.5 Hz, 2H), 4.46 (d, J=13.0 Hz, 1H), 4.13 (d, J=11.0 Hz, 1H), 3.85 (s, 2H), 3.73 (d, J=13.5 Hz, 1H), 3.62-3.56 (m, 2H), 2.89-2.85 (m, 1H), 2.78 (q, J=7.5 Hz, 2H), 2.73 (dd, J=12.5, 3.5 Hz, 1H), 2.12 (t, J=11.0 Hz, 1H), 2.02 (dd, J=11.5, 3.5 Hz, 11H), 1.30 (t, J=7.5 Hz, 3H);

$^{13}$C-NMR (126 MHz, CDCl$_3$) δ163.69, 161.91, 15831, 154.18, 135.15, 129.63, 129.18, 128.72, 128.44, 123.63, 122.55, 119.90, 110.93, 109.59, 57.61, 56.97, 51.82, 51.37, 49.55, 48.77, 41.61, 20.20, 13.10; and MS (ESI) m/z for C$_{25}$H$_{27}$N$_3$O$_3$ [M+H]$^+$: calcd 418.2153, found 418.2093.

17. Preparation Example 15: C207, L19013

A compound of Formula 18 was obtained by the same method as in Preparation Example 10, except that 4-methylbenzyl bromide was used instead of methyl iodide, which is a reaction material.

[Formula 18]

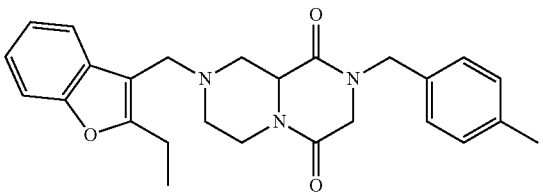

2-((2-ethylbenzofuran-3-yl)methyl)-8-(4-methylbenzyl)hexahydro-2H-pyrazino[1,2-a]pyrazine-6,9-dione (expressed as 0207 or L19013).

$^1$H-NMR (500 MHz, CDCl$_3$) δ7.59 (d, J=7.5 Hz, 1H), 7.40 (d, J=8.0 Hz, 1H), 7.26-7.17 (m, 2H), 7.14 (s, 4H), 4.52 (dd, J=32.5, 14.0 Hz, 2H), 4.45 (d, J=13.5 Hz, 1H), 4.12 (dd, J=10.5, 2.5 Hz, 1H), 3.84 (s, 2H), 373 (d, J=13.5 Hz, 1H), 3.61-3.56 (m, 2H), 2.89-2.85 (m, 1H), 2.78 (q, J=7.5 Hz, 2H), 2.72 (dt, J=12.5, 3.0 Hz, 1H), 2.33 (s, 3H), 2.20 (d, J=11.5 Hz, 1H), 2.01 (dt, J=11.5, 3.0 Hz, 1H), 130 (t, J=7.5 Hz, 3H);

$^{13}$C-NMR (126 MHz, CDCl$_3$) δ163.60, 161.97, 158.30, 154.18, 138.24, 132.11, 129.83, 129.64, 128.77, 123.63, 122.55, 119.90, 110.92, 109.60, 57.62, 56.97, 51.82, 51.37, 49.28, 48.66, 41.59, 21.36, 20.19, 13.10; and MS (ESI) m/z for C$_{26}$H$_{29}$N$_3$O$_3$S [M+H]$^+$: calcd 432.2282, found 432.2240.

18. Preparation Example 16: C208, L19014

A compound of Formula 19 was obtained by the same method as in Preparation Example 10, except that 4-chlorobenzyl bromide was used instead of methyl iodide, which is a reaction material.

[Formula 19]

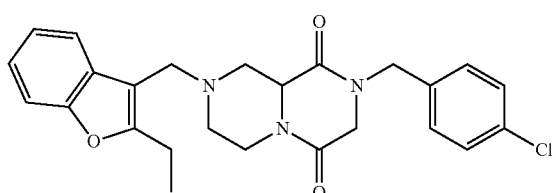

8-(4-chlorobenzyl)-2-((2-ethylbenzofuran-3-yl)methyl)hexahydro-2H-pyrazino[1,2-a]pyrazine-6,9-dione (expressed as C208 or L19014).

$^1$H-NMR (500 MHz, CDCl$_3$) δ7.59 (d, J=7.0 Hz, 1H), 7.40 (d, J=8.0 Hz, 1H), 7.31 (d, J=8.0 Hz, 2H), 7.25-7.17 (m, 4H), 4.52 (dd, J=23.5, 14.5 Hz, 2H), 4.46 (d, J=13.0 Hz, 1H), 4.12 (dd, J=11.0, 3.0 Hz, 1H), 3.84 (d, J=2.0 Hz, 2H), 3.73 (d, J=13.5 Hz, 1H), 3.61-3.56 (m, 2H), 2.88 (d, J=11.5 Hz, 1H), 2.81-2.70 (m, 3H), 2.10 (t, J=11.0 Hz, 1H), 2.02 (td, J=11.5, 3.5 Hz, 1H), 1.31 (t, J=8.0 Hz, 3H);

$^{13}$C-NMR (126 MHz, CDCl$_3$) δ163.78, 161.69, 158.32, 154.18, 134.41, 133.73, 130.09, 129.61, 129.37, 123.65, 122.55, 119.88, 110.94, 109.54, 57.56, 56.89, 51.81, 51.35, 48.96, 48.82, 41.64, 20.19, 13,10; and MS (ESI) m/z for C$_{25}$H$_{26}$ClN$_3$O$_3$ [M+H]$^+$: calcd 452.1736, found 452.1688.

19. Preparation Example 17: C209, L19015

A compound of Formula 20 was obtained by the same method as in Preparation Example 10, except that 4-bromobenzyl bromide was used instead of methyl iodide, which is a reaction material.

[Formula 20]

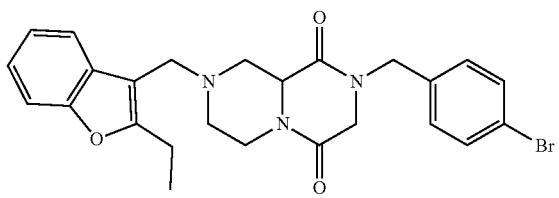

8-(4-bromobenzyl)-2-((2-ethylbenzofuran-3-yl)methyl)hexahydro-2H-pyrazino[1,2-a]pyrazine-6,9-dione (expressed as C209 or L19015).

$^1$H-NMR (500 MHz, CDCl$_3$) δ7.59 (d, J=7.5 Hz, 1H), 746 (d, J=8.0 Hz, 2H), 7.40 (d, J=8.0 Hz, 1H), 7.25-7.17 (m, 2H), 7.13 (d, J=8.5 Hz, 2H'), 4.55-4.43 (m, 3H), 4.12 (d, J=10.0 Hz, 1H), 3.84 (s, 2H), 373 (d, J=13.0 Hz, 1H), 3.61-3.55 (m, 2H), 2.88 (d, J=10.5 Hz, 1H), 2.81-2.69 (m, 3H), 2.10 (t, J=11.0 Hz, 1H), 2.02 (dt, J=11.5, 3.0 Hz 1H), 1.31 (t, J=7.5 Hz, 3H);

$^{13}$C-NMR (126 MHz, CDCl$_3$) δ163.79, 161.67, 158.32, 154.18, 134.24, 132.33, 130.41, 129.61, 123.65, 122.55, 122.52, 119.88, 110.94, 109.54, 57.55, 56.89, 51.81, 51.35, 49.03, 48.84, 41.64, 20.19, 13.10; and MS (ESI) m/z for C$_{25}$H$_{26}$BrN$_3$O$_3$ [M+H]$^+$: calcd 496.1230, found 496.1192.

20. Preparation Example 18: C210, L19016

A compound of Formula 21 was obtained by the same method as in Preparation Example 10, except that 4-fluorobenzyl bromide was used instead of methyl iodide, which is a reaction material.

[Formula 21]

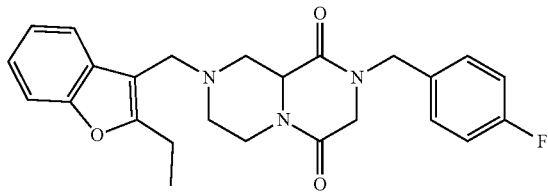

2-((2-ethylbenzofuran-3-yl)methyl)-8-(4-fluorobenzyl)hexahydro-2H-pyrazino[1,2-a]pyrazine-6,9-dione (expressed as C210 or L19016).

$^1$H-NMR (500 MHz, CDCl$_3$) δ7.59 (d, J=7.5 Hz, 1H), 7.40 (d, J=8.0 Hz, 1H), 7.25-7.17 (m, 4H), 7.02 (t, J=8.5 Hz, 2H), 4.53 (dd, J=32.5, 14.5 Hz, 2H), 4.46 (d, J=13.0 Hz, 1H), 4.12 (dd, J=11.0, 3.0 Hz, 1H), 3.85 (s, 2H), 3.73 (d, J=13.5 Hz, 1H), 3.59 (m, 2H), 2.88 (d, J=11.5 Hz, 1H), 2.81-2.70 (m, 3H), 2.11 (t, J=11.5 Hz, 1H), 2.02 (dt, J=11.5, 3.5 Hz, 1H), 130 (t, J=7.5 Hz, 3H);

$^{13}$C-NMR (126 MHz, CDCl$_3$) δ163.72, 161.75, 15831, 154.18, 131.07, 131.04, 130.56, 130.50, 129.62, 123.64, 122.55, 119.89, 116.20, 116.03, 110.93, 109.56, 57.58, 56.91, 51.82, 51.36, 48.87, 4874, 41.62, 20.19, 13.10; and MS (ESI) m/z for C$_{25}$H$_{26}$FN$_3$O$_3$ [M+H]$^+$: calcd 436.2031, found 436.1994.

21. Preparation Example 19: C211, L19017

A compound of Formula 22 was obtained by the same method as in Preparation Example 10, except that 4-trifluoromethylbenzyl bromide was used instead of methyl iodide, which is a reaction material.

[Formula 22]

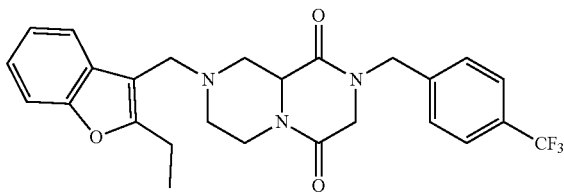

2-((2-ethylbenzofuran-3-yl)methyl)-8-(4-(trifluoromethyl)benzyl)hexahydro-2H-pyrazino[1,2-a]pyrazine-6,9-dione (expressed as C211 or L19017).

$^1$H-NMR (500 MHz, CDCl$_3$) δ7.62-7.58 (m, 3H), 7.41 (d, J=7.5 Hz, 1H), 7.37 (d, J=8.0 Hz, 2H), 7.26-7.19 (m, 2H), 4.62 (s, 2H), 4.47 (d, J=13.5 Hz, 1H), 4.15 (dd, J=11.0, 3.0 Hz, 1H), 3.87 (d, J=4.0 Hz, 2H), 3.73 (d, J=13.0 Hz, 1H), 3.62-3.57 (m, 2H), 2.90 (d, J=11.5 Hz, 1H), 2.82-2.71 (m, 3H), 2.12 (t, J=11.0 Hz, 1H), 2.03 (dt, J=11.5, 3.5 Hz, 1H), 1.31 (t, J=7.5 Hz, 3H);

$^{13}$C-NMR (126 MHz, CDCl$_3$) δ163.93, 161.55, 15834, 154.18, 139.28, 129.60, 128.92, 126.21, 126.18, 126.15, 126.12, 12366, 122.56, 119.87, 110.95, 109.52, 57.55, 56.88, 51.81, 51.35, 49.20, 49.03, 41.67, 20.19, 13.08; and MS (ESI) m/z for C$_{26}$H$_{26}$F$_3$N$_3$O$_3$ [M+H]$^+$: calcd 486.1999, found 486.1958.

22. Preparation Example 20: C212, L19018

A compound of Formula 23 was obtained by the same method as in Preparation Example 10, except that 4-cyanobenzyl bromide was used instead of methyl iodide, which is a reaction material.

[Formula 23]

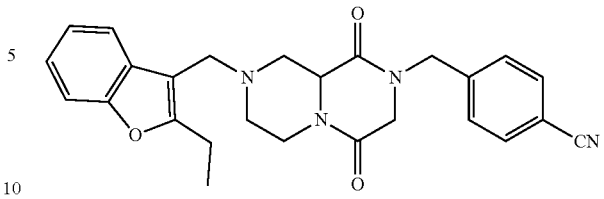

4-((8-((2-ethylbenzofuran-3-yl)methyl)-1,4-dioxooctahydro-2H-pyrazino[1,2-a]pyrazin-2-yl)methyl)benzonitrile (expressed as C212 or L19018).

$^1$H-NMR (500 MHz, CDCl$_3$) δ7.64 (d, J=8.5 Hz, 2H), 7.59 (d, J=7.5 Hz, 1H), 7.40 (d, J=8.0 Hz, 1H), 7.36 (d, J=8.5 Hz, 2H), 7.30 (dt, J=8.0, 1.5 Hz, 1H), 7.19 (dt, J=7.5, 1.5 Hz, 1H), 4.61 (s, 2H), 4.47 (d, J=13.5 Hz, 1H), 4.15 (dd, J=11.0, 3.0 Hz, 1H), 3.88 (d, J=5.5 Hz, 2H), 3.73 (d, J=13.5 Hz, 1H), 3.63-3.56 (m, 2H), 2.90 (d, J=12.0 Hz, 1H), 2.81-2.72 (m, 3H), 2.12 (t, J=11.5 Hz, 1H), 2.04 (dt, J=12.0, 3.5 Hz, 1H), 1.31 (t, J=7.5 Hz, 3H);

$^{13}$C-NMR (126 MHz, CDCl$_3$) δ164.05, 161.42, 158.33, 154.17, 140.63, 132.98, 129.59, 129.16, 123.66, 122.55, 119.85, 118.57, 112.43, 110.95, 109.48, 57.50, 56.81, 51.80, 51.34, 49.33, 49.20, 41.70, 20.19, 13.09; and MS (ESI) m/z for C$_{26}$H$_{26}$N$_4$O$_3$ [M+H]$^+$: calcd 443.2078, found 443.2043.

23. Preparation Example 21: C213, L19019

A compound of Formula 24 was obtained by the same method as in Preparation Example 10, except that 4-nitrobenzyl bromide was used instead of methyl iodide, which is a reaction material.

[Formula 24]

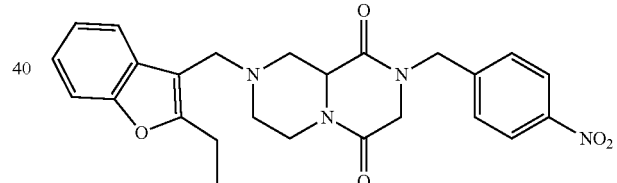

2-((2-ethylbenzofuran-3-yl)methyl)-8-(4-nitrobenzyl)hexahydro-2H-pyrazino[1,2-a]pyrazine-6,9-dione (expressed as C213 or L19019).

$^1$H-NMR (500 MHz, CDCl$_3$) δ8.20 (d, J=8.5 Hz, 2H), 7.59 (d, J=7.5 Hz, 1H), 7.42 (d, J=8.5 Hz, 2H), 7.40 (d, J=7.5 Hz, 1H), 7.26-7.17 (m, 2H), 4.67 (s, 2H), 4.47 (d, J=13.0 Hz, 1H), 4.17 (dd, J=11.0, 3.0 Hz, 1H), 3.90 (d, J=5.5 Hz, 2H), 374 (d, J=13.0 Hz, 1H), 3.63-3.56 (m, 2H), 2.91 (d, J=11.5 Hz, 1H), 2.82-2.73 (m, 3H), 2.13 (t, J=11.0 Hz, 1H), 2.04 (dd, J=11.5, 3.0 Hz, 1H), 1.31 (t, J=7.5 Hz, 3H);

$^{13}$C-NMR (126 MHz, CDCl$_3$) δ16410, 161.37, 158.35, 154.18, 148.02, 142.61, 129.59, 129.30, 124.40, 123.67, 122.56, 119.85, 110.96, 109.47, 57.50, 56.81, 51.80, 5134, 49.26, 49.11, 41.71, 20.19, 13.09; and MS (ESI) m/z for C$_{25}$H$_{26}$N$_4$O$_5$ [M+H]$^+$: calcd 463.1976, found 463.1939.

24. Preparation Example 22: C214, L19020

A compound of Formula 25 was obtained by the same method as in Preparation Example 10, except that 4-phenylbenzyl bromide was used instead of methyl iodide, which is a reaction material.

[Formula 25]

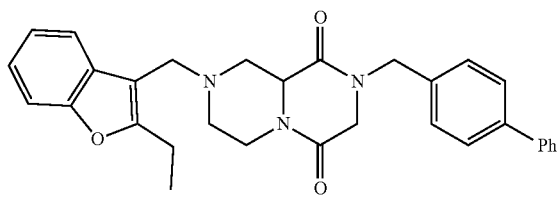

8-([1,1'-biphenyl]-4-ylmethyl)-2-((2-ethylbenzofuran-3-yl)methyl)hexahydro-2H-pyrazino[1,2-a]pyrazine-6,9-dione (expressed as C214 or L19020).

$^1$H-NMR (500 MHz, CDCl$_3$) δ7.61-7.54 (m, 5H), 7.46-7.39 (m, 3H), 7.37-7.31 (m, 3H), 7.24-7.17 (m, 2H), 4.60 (q, J=14.5 Hz, 2H), 4.46 (d, J=13.0 Hz, 1H), 4.14 (, J=11.0 Hz, 1H), 3.90 (s, 2H), 3.73 (d, J=13.5 Hz, 1H), 3.63-3.57 (m, 2H), 2.88 (d, J=12.0 Hz, 1H), 2.81-2.70 (m, 3H), 2.14 (t, J=11.0 Hz, 1H), 2.02 (dt, J=12.0, 3.5 Hz, 1H), 1.31 (t, J=7.5 Hz, 3H);

$^{13}$C-NMR (126 MHz, CDCl$_3$) δ16373, 161.91, 158.33, 154.19, 141.46, 14070, 134.13, 129.65, 129.23, 129,08, 127.93, 127.76, 12733, 123.65, 122.57, 119.92, 110.94, 109.59, 5763, 56.97, 51.84, 51.38, 49.29, 48.84, 41.63, 20.21, 13.13; and MS (ESI) m/z for C$_{31}$H$_{31}$N$_3$O$_3$ [M+H]$^+$: calcd 494.2438, found 494.2394.

25. Preparation Example 23: C215, L19021

A compound of Formula 26 was obtained by the same method as in Preparation Example 10, except that phenylethyl bromide was used instead of methyl iodide, which is a reaction material.

[Formula 26]

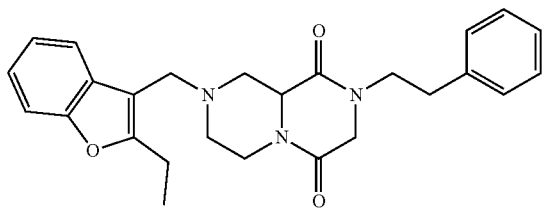

2-((2-ethylbenzofuran-3-yl)methyl)-8-phenethylhexahydro-2H-pyrazino[1,2-a]pyrazine-6,9-dione (expressed as C215 or L19021).

$^1$H-NMR (500 MHz, CDCl$_3$) δ7.59 (d, J=7.0 Hz, 1H), 7.40 (d, J=8.0 Hz, 1H), 7.31-7.16 (m, 7H), 4.44 (d, J=13.0 Hz, 1H), 4.02 (dd, J=11.0, 3.5 Hz, 1H), 3.78 (d, J=7.0 Hz, 2H), 3.70 (d, J=13.5 Hz, 1H), 3.65-3.54 (m, 3H), 3.51 (d, J=11.0 Hz, 1H), 2.91-2.85 (m, 3H), 2.78 (q, J=7.5 Hz, 2H), 2.71 (dt, J=12.5, 3.0 Hz, 1H), 2.03-1.95 (m, 2H), 1.30 (t, J=7.5 Hz, 3H);

$^{13}$C-NMR (126 MHz, CDCl$_3$) δ163.53, 161.89, 15830, 154.17, 138.14, 129.64, 128.97, 128.94, 127.06, 123.63, 122.55, 119.91, 110.92, 109.59, 57.48, 56.86, 51.82, 51.41, 50.13, 48.14, 41.60, 33.08, 20.19, 13.12; and MS (ESI) m/z for C$_{26}$H$_{29}$N$_3$O$_3$ [M+H]$^+$: calcd 432.2282, found 432.2239.

26. Preparation Example 24: C216, L19022

A compound of Formula 27 was obtained by the same method as in Preparation Example 10, except that 4-fluorophenethyl bromide was used instead of methyl iodide, which is a reaction material.

[Formula 27]

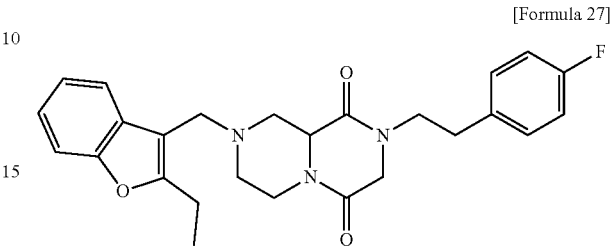

2-((2-ethylbenzofuran-3-yl)methyl)-8-(4-fluorophenethyl)hexahydro-2H-pyrazino[1,2-a]pyrazine-6,9-dione (expressed as C216 or L19022).

$^1$H-NMR (500 MHz, CDCl$_3$) δ7.58 (d, J=7.0 Hz, 1H), 7.39 (d, J=8.0 Hz, 1H), 7.23-7.17 (m, 2H), 7.17-7.12 (m, 2H), 6.97 (t, J=8.5 Hz, 2H), 4.44 (d, J=13.0 Hz, 1H), 4.01 (dd, J=11.0, 3.0 Hz, 1H), 3.82 (d, J=6.0, 2H), 3.69 (d, J=13.5 Hz, 1H), 3.63-3.47 (m, 4H), 2.88-2.83 (m, 3H), 2.79-2.70 (m, 3H), 2.01-1.95 (m, 2H), 1.29 (t, J=7.8 Hz, 3H);

$^{13}$C-NMR (126 MHz, CDCl$_3$) δ163.57, 161.78, 15832, 154.16, 133.74, 133.72, 130.41, 13034, 129.62, 123.63, 122.54, 119,89, 115.88, 115.71, 110.92, 109.55, 57.45, 56.82, 51.80, 51.41, 50.00, 47.95, 41.61, 32.20, 20.18, 13.10; and MS (ESI) m/z for C$_{26}$H$_{28}$FN$_3$O$_3$ [M+H]$^+$: calcd 450.2188, found 450.2155.

27. Preparation Example 25: C302, L19023

A compound of Formula 28 was obtained by the same method as in Preparation Example 1-1, except that methyl iodide was used instead of ethyl iodide, which is a reaction material in Step 1 (Reaction Scheme 1).

[Formula 28]

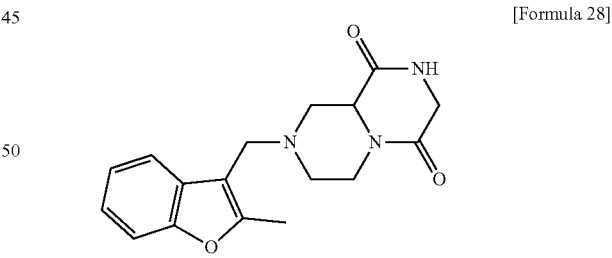

2-((2-methylbenzofuran-3-yl)methyl)hexahydro-2H-pyrazino[1,2-a]pyrazine-6,9-dione (expressed as C302 or L19023).

$^1$H-NMR (500 MHz, CDCl$_3$) δ7.57 (d, J=7.0 Hz, 1H), 7.39 (d, J=7.8 Hz, 1H), 7.24-7.17 (m, 2H), 4.50 (d, J=13.5 Hz, 1H), 4.06 (d, J=11.0 Hz, 1H), 4.00 (s, 2H), 3.64 (dd, J=52.0, 13.5 Hz, 2H), 3.46 (d, J=11.5 Hz, 1H), 2.90 (d, J=11.5 Hz, 1H), 2.75 (td, J=12.5, 3.0 Hz, 1H), 2.42 (s, 3H), 2.12 (t, J=11.5 Hz, 1H), 2.06-2.02 (td, J=11.5, 3.0 Hz, 1H);

$^{13}$C-NMR (126 MHz, CDCl$_3$) δ166.24, 161.97, 154.13, 153.42, 129.60, 123.64, 122.61, 119.68, 110.83, 110.45, 57.17, 56.34, 51.95, 51.60, 44.76, 41.75, 12.48; and

28. Preparation Example 26: C303, L19024

A compound of Formula 29 was obtained by the same method as in Preparation Example 1-1, except that 2-butyl benzofuran was purchased and reacted instead of 2-ethyl benzofuran produced in Step 1 (Reaction Scheme 1).

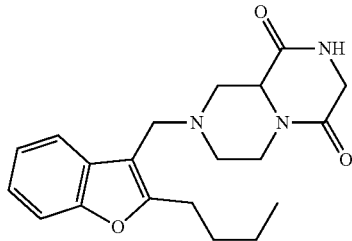

[Formula 29]

2-((2-butylbenzofuran-3-yl)methyl)hexahydro-2H-pyrazino[1,2-a]pyrazine-6,9-dione (expressed as C303 or L19024).

$^1$H NMR (500 MHz, CDCl$_3$) δ7.59 (d, J=7.5 Hz, 1H), 7.39 (d, J=8.0 Hz, 1H), 7.24-7.16 (m, 2H), 4.50 (d, J=13.0 Hz, 1H), 4.07 (d, J=11.0 Hz, 1H), 4.00 (s, 2H), 3.65 (dd, J=660, 13.5 Hz, 2H), 3.47 (d, J=11.5 Hz, 1H), 2.89 (d, J=11.5 Hz, 1H), 277-2.71 (m, 3H), 2.12 (t, J=11.0 Hz, 1H), 2.03 (td, J=11.5, 3.0 Hz, 1H), 1.74-1.67 (m, 2H), 1.42-1.33 (m, 2H), 0.94 (t, J=7.4 Hz, 3H; $^{13}$C-NMR (126 MHz, CDCl$_3$) δ16635, 161.98, 157.33, 154.18, 129.57, 123.61, 122.52, 119.88, 110.92, 110.24, 57.20, 56.51, 51.96, 51.56, 44.76, 41.79, 30.60, 26.44, 2263, 14.10; and MS (ESI) m/z for C$_{20}$H$_{25}$N$_3$O$_3$ [M+H]+: calcd 356.1969, found 356.1979.

29. Preparation Example 27: C304, L19025

A compound of Formula 30 was obtained by the same method as in Preparation Example 1-1, except that hexyl bromide was used instead of ethyl iodide, which is a reaction material in Step 1 (Reaction Scheme1).

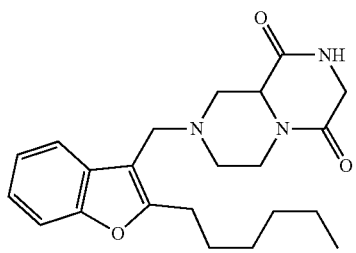

[Formula 30]

2-((2-hexylbenzofuran-3-yl)methyl)hexahydro-2H-pyrazino[1,2-a]pyrazine-6,9-dione (expressed as C304 or L19025).

$^1$H NMR (500 MHz, CDCl$_3$) δ7.59 (d, J=7.0 Hz, 1H), 7.39 (d, J=8.0 Hz, 1H), 7.24-7.16 (m, 2H), 4.65 (s, 1H), 4.47 (d, J=13.5 Hz, 1H), 4.04 (d, J=11.0 Hz, 1H), 3.96 (s, 2H), 3.64 (dd, J=70.0, 13.0 Hz, 2H), 3.46 (d, J=11.5 Hz, 1H), 2.88 (d, J=11.5 Hz, 1H), 2.76-2.72 (m, 3H), 2.10 (d, J=11.0 Hz, 1H), 2.01 (td, J=11.5, 3.0 Hz, 1H), 1.75-1.66 (m, 2H), 1.37-1.28 (m, 5H), 0.88 (t, J=7.0 Hz, 3H);

$^{13}$C-NMR (126 MHz, CDCl$_3$) δ166.27, 162.03, 157.39, 154.18, 129.59, 123.62, 122.53, 119.88, 110.93, 110.20, 57.18, 56.51, 51.94, 51.52, 44.72, 41.78, 31.79, 29.23, 28.48, 26.75, 22.79, 14.32; and MS (ESI) m/z for C$_{22}$H$_{29}$N$_3$O$_3$ [M+H]+: calcd 384.2282, found 384.2292.

30. Preparation Example 28: C306, L19026

A compound of Formula 31 was obtained by the same method as in Preparation Example 1-1, except that benzyl bromide was used instead of ethyl iodide, which is a reaction material in Step 1 (Reaction Scheme1).

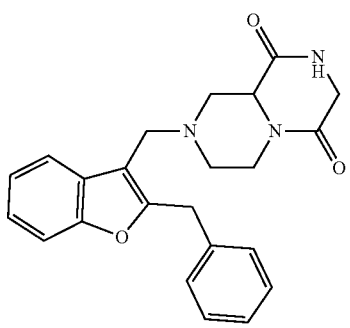

[Formula 31]

2-((2-benzylbenzofuran-3-yl)methyl)hexahydro-2H-pyrazino[1,2-a]pyrazine-6,9-dione (expressed as C306 or L19026).

$^1$H-NMR (500 MHz, CDCl$_3$) δ7.64 (d, J=7.0 Hz, 1H), 7.41 (d, J=8.0 Hz, 2H), 7.31-7.19 (m, 6H), 4.47 (d, J=13.0 Hz, 1H), 4.14 (s, 2H), 4.05 (d, J=11.0 Hz, 1H), 4.01 (s, 2H), 3.69 (dd, J=73.0, 13.5 Hz, 2H), 3.49 (d, J=11.0 Hz, 1H), 2.87 (d, J=11.5 Hz, 1H), 2.70 (dt, J=12.5, 3.0 Hz, 1H), 2.13 (t, J=11.5 Hz, 1H), 2.00 (dt, J=11.5, 3.0 Hz, 1H);

$^{13}$C-NMR (126 MHz, CDCl$_3$) δ166.27, 162.01, 154.96, 154.40, 137.71, 129.45, 128.86, 128.79, 126.93, 124.06, 122.73, 120.07, 111.55, 111.23, 57.16, 56.58, 51.92, 51.58, 44.77, 41.73, 33.09; and MS (ESI) m/z for C$_{23}$H$_{23}$N$_3$O$_3$ [M+H]+: calcd 390.1812, found 390.1820.

31. Preparation Example 29: C308, L19027

A compound of Formula 32 was obtained by the same method as in Preparation Example 1-1, except that 4-chlorobenzyl bromide was used instead of ethyl iodide, which is a reaction material in Step 1 (Reaction Scheme1).

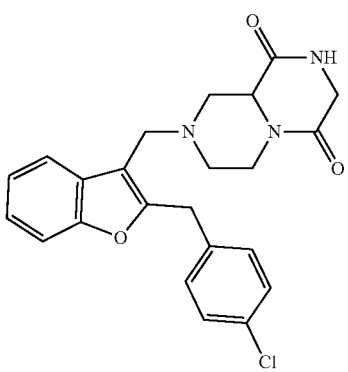

[Formula 32]

2-((2-(4-chlorobenzyl)benzofuran-3-yl)methyl)hexahydro-2H-pyrazino[1,2-a]pyrazine-6,9-dione (expressed as C308 or L19027).

$^1$H-NMR (500 MHz, CDCl$_3$) δ7.62 (d, J=7.5 Hz, 1H), 7.40 (d, J=8.0 Hz, 1H), 7.26-7.15 (m, 6H), 4.48 (d, J=13.0 Hz, 1H), 4.09 (s, 2H), 4.05-4.00 (m, 3H), 3.69 (dd, J=58.0, 13.5 Hz, 2H), 3.46 (d, J=11.0 Hz, 1H), 2.87 (d, J=11.5 Hz, 1H), 2.70 (dt, J=12.5, 3.0 Hz, 1H), 2.09 (t, J=11.0 Hz, 1H), 2.02 (dt, J=11.5, 3.0 Hz, 1H);

$^{13}$C-NMR (126 MHz, CDCl$_3$) δ166.01, 161.93, 154.40, 154.29, 136.14, 13275, 130.12, 129.30, 128.96, 124.23, 122.83, 120.07, 111.75, 111.24, 57.12, 56.48, 51.88, 51.69, 44.80, 41.73, 32.43; and MS (ESI) m/z for C$_{23}$H$_{22}$ClN$_3$O$_3$ [M+H]$^+$: calcd 424.1423, found 424.1423.

32. Preparation Example 30: C310, L19028

A compound of Formula 33 was obtained by the same method as in Preparation Example 1-1, except that 4-fluorobenzyl bromide was used instead of ethyl iodide, which is a reaction material in Step 1 (Reaction Scheme1).

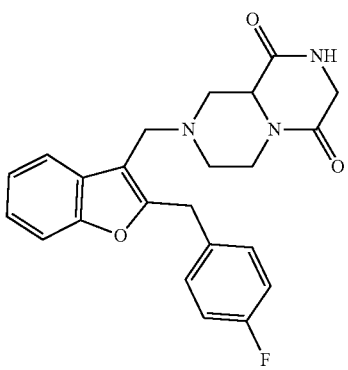

[Formula 33]

2-((2-(4-fluorobenzyl)benzofuran-3-yl)methyl)hexahydro-2H-pyrazino[1,2-a]pyrazine-6,9-dione (expressed as C310 or L19028).

1H-NMR (500 MHz, CDCl$_3$) δ7.65-7.61 (m, 2H), 7.38 (d, J=7.5 Hz, 1H), 7.25-7.18 (m, 3H), 6.97 (t, J=8.5 Hz, 2H), 4.47 (d, J=13.0 Hz, 1H), 4.10 (s, 2H), 4.02 (d, J=11.0 Hz, 1H) 3.97 (s, 2H), 3.69 (dd, J=50.5, 13.5 Hz, 2H), 3.47 (d, J=10.5 Hz, 1H), 2.88 (d, J=11.0 Hz, 1H), 2.74-2.67 (m, 1H), 2.10 (t, J=11.5 Hz, 1H), 2032.06-2.00 (m, 1H);

$^{13}$C-NMR (126 MHz, CDCl$_3$) δ165.41, 162.72, 162.33, 160.77, 154.50, 154.25, 133.36, 133.34, 130.22, 130.15, 129.28, 124,01, 122.68, 120.06, 115.59, 115.43, 111.60, 111.03, 57.08, 56.42, 51.79, 51.68, 44.65, 41.55, 32.13; and MS (ESI) m/z for C$_{23}$H$_{22}$FN$_3$O$_3$ [M+H]+: calcd 408.1718, found 408.1723.

33. Preparation Example 31: C315, L19030

A compound of Formula 34 was obtained by the same method as in Preparation Example 1-1, except that phenylethyl bromide was used instead of ethyl iodide, which is a reaction material in Step 1 (Reaction Scheme1).

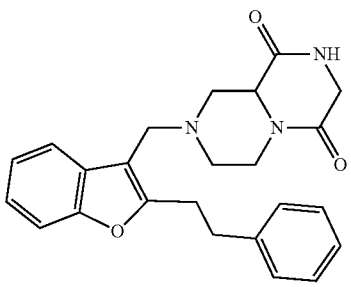

[Formula 34]

2-((2-phenethylbenzofuran-3-yl)methyl)hexahydro-2H-pyrazino[1,2-a]pyrazine-6,9-dione (expressed as C$_{315}$ or L19030).

$^1$H-NMR (500 MHz, CDCl$_3$) δ7.59 (d, J=7.5 Hz, 1H), 746 (d, J=8.0 Hz, 1H), 7.28-7.24 (m, 3H), 7.23-7.18 (m, 2H), 7.15 (d, J=7.0 Hz, 2H), 4.41 (d, J=11.5 Hz, 1H), 4.04 (d, J=11.0 Hz, 1H), 4.00 (s, 2H), 3.45 (dd, J=84.0, 13.5 Hz, 2H), 3.42 (d, J=11.0 Hz, 1H), 3.03-3.09 (m, 4H), 2.69-2.63 (m, 2H), 2.04 (t, J=11.0 Hz, 1H), 1.87-1.80 (m, 1H);

$^{13}$C-NMR (126 MHz, CDCl$_3$) δ166.24, 161.90, 155.71, 154.27, 141.08, 12943, 128.72, 128.70, 12649, 123.84, 122.62, 120.06, 111.15, 110.98, 57.17, 56.49, 5175, 51.27, 44.77, 41.74, 34.57, 29.10; and MS (ESI) m/z for C$_{24}$H$_{25}$N$_3$O$_3$ [M+H]$^+$: calcd 404.1969, found 404.1972.

The structures of the compounds of Formulas 2 to 34 synthesized by the above-described Preparation Examples are shown in Table 2 below.

TABLE 2
| Formula No. | Chemical Structure |
|---|---|
| 2 | 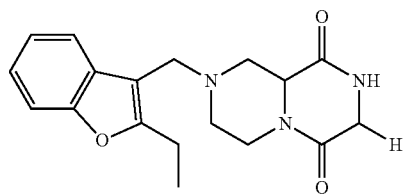 [SMILES: CCc1oc2ccccc2c1CN1CCN2C(=O)CNC(=O)C2C1] |
| 3 | HCl 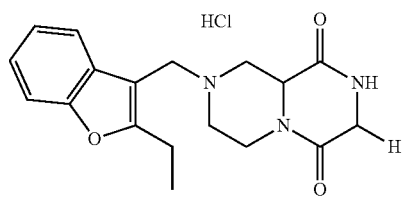 [SMILES: CCc1oc2ccccc2c1CN1CCN2C(=O)CNC(=O)C2C1 ; Cl] |
| 4 | HCl 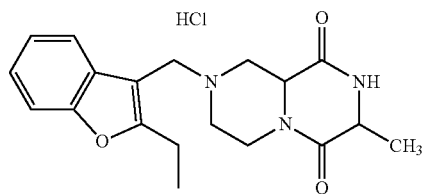 [SMILES: CCc1oc2ccccc2c1CN1CCN2C(=O)C(C)NC(=O)C2C1 ; Cl] |
| 5 | 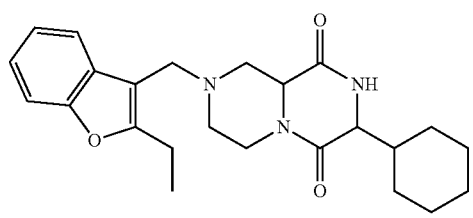 [SMILES: CCc1oc2ccccc2c1CN1CCN2C(=O)C(C3CCCCC3)NC(=O)C2C1] |
| 6 | HCl 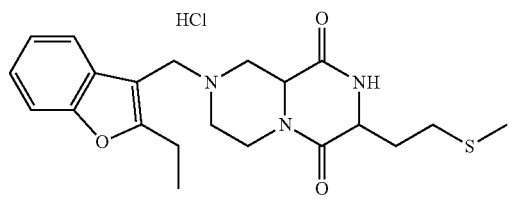 [SMILES: CCc1oc2ccccc2c1CN1CCN2C(=O)C(CCSC)NC(=O)C2C1 ; Cl] |
| 7 | HCl 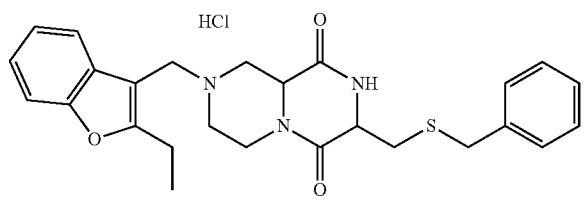 [SMILES: CCc1oc2ccccc2c1CN1CCN2C(=O)C(CSCc3ccccc3)NC(=O)C2C1 ; Cl] |
| 8 | 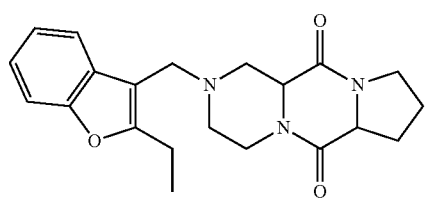 [SMILES: CCc1oc2ccccc2c1CN1CCN2C(=O)C3CCCN3C(=O)C2C1] |

TABLE 2-continued

| Formula No. | Chemical Structure |
|---|---|
| 9 | 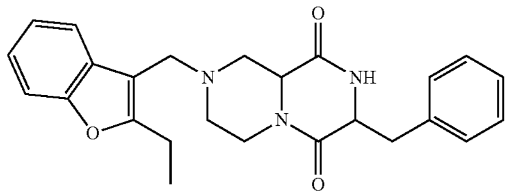 [SMILES: CCc1oc2ccccc2c1CN1CCN2C(=O)C(Cc3ccccc3)NC(=O)C2C1] |
| 10 | HCl |
| 11 | HCl |
| 12 | HCl |
| 13 | 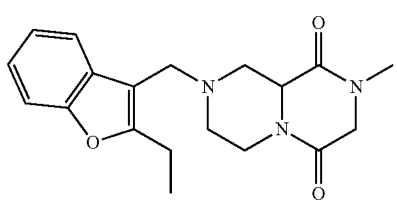 [SMILES: CCc1oc2ccccc2c1CN1CCN2C(=O)CN(C)C(=O)C2C1] |
| 14 | 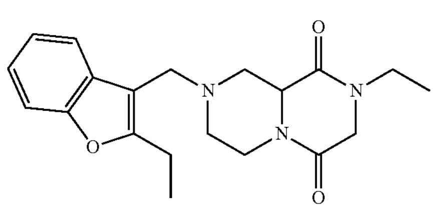 [SMILES: CCc1oc2ccccc2c1CN1CCN2C(=O)CN(CC)C(=O)C2C1] |
| 15 | 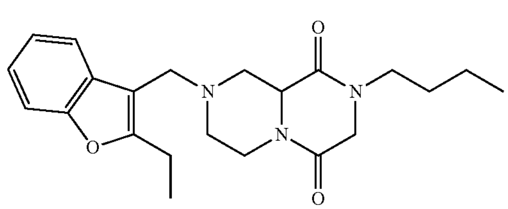 [SMILES: CCCCN1CC(=O)N2CCN(Cc3c(CC)oc4ccccc34)CC2C1=O] |

TABLE 2-continued

| Formula No. | Chemical Structure |
|---|---|
| 16 | 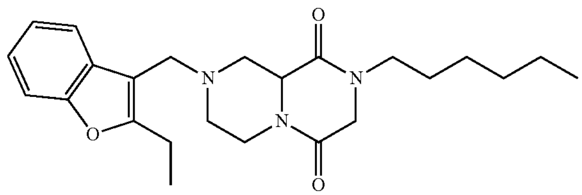 [SMILES: CCCCCCN1CC(=O)N2CCN(Cc3c(CC)oc4ccccc34)CC2C1=O] |
| 17 | 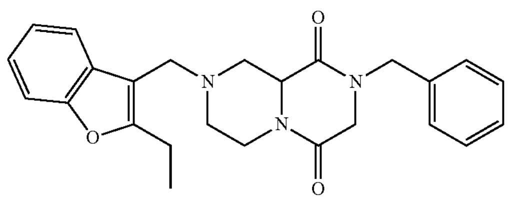 [SMILES: CCc1oc2ccccc2c1CN1CCN2C(=O)CN(Cc3ccccc3)C(=O)C2C1] |
| 18 | 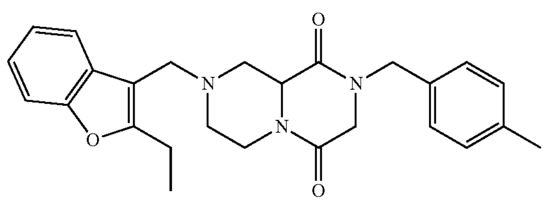 [SMILES: CCc1oc2ccccc2c1CN1CCN2C(=O)CN(Cc3ccc(C)cc3)C(=O)C2C1] |
| 19 | 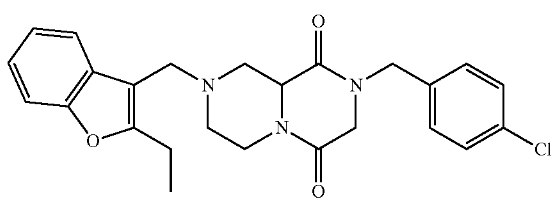 [SMILES: CCc1oc2ccccc2c1CN1CCN2C(=O)CN(Cc3ccc(Cl)cc3)C(=O)C2C1] |
| 20 | 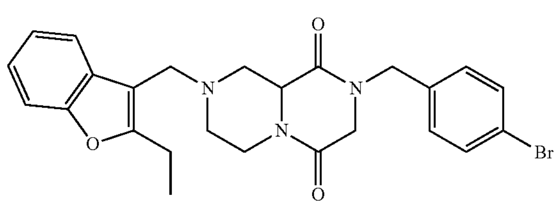 |
| 21 | 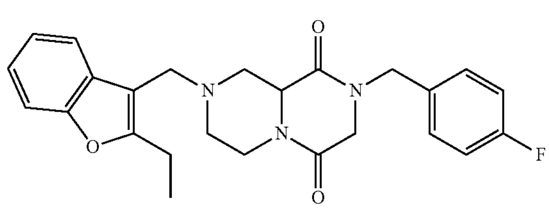 [SMILES: CCc1oc2ccccc2c1CN1CCN2C(=O)CN(Cc3ccc(F)cc3)C(=O)C2C1] |
| 22 | 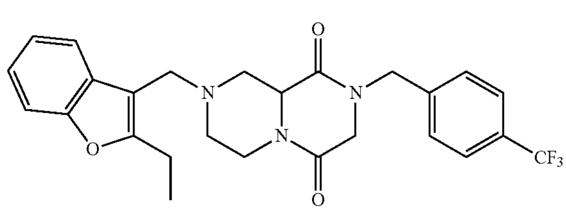 [SMILES: CCc1oc2ccccc2c1CN1CCN2C(=O)CN(Cc3ccc(C(F)(F)F)cc3)C(=O)C2C1] |

TABLE 2-continued

| Formula No. | Chemical Structure |
|---|---|
| 23 | 2-ethylbenzofuran-CH2-[piperazine-2,5-dione bicyclic]-CH2-C6H4-CN |
| 24 | 2-ethylbenzofuran-CH2-[piperazine-2,5-dione bicyclic]-CH2-C6H4-NO2 |
| 25 | 2-ethylbenzofuran-CH2-[piperazine-2,5-dione bicyclic]-CH2-C6H4-Ph |
| 26 | 2-ethylbenzofuran-CH2-[piperazine-2,5-dione bicyclic]-CH2CH2-Ph |
| 27 | 2-ethylbenzofuran-CH2-[piperazine-2,5-dione bicyclic]-CH2CH2-C6H4-F |
| 28 | 2-methylbenzofuran-CH2-[piperazine-2,5-dione bicyclic with NH] |
| 29 | 2-butylbenzofuran-CH2-[piperazine-2,5-dione bicyclic with NH] |

TABLE 2-continued
| Formula No. | Chemical Structure |
|---|---|
| 30 | 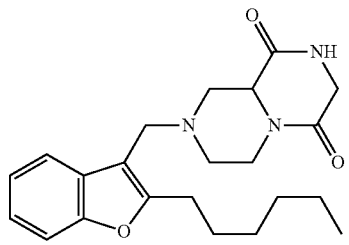 [SMILES: CCCCCCc1oc2ccccc2c1CN1CCN2C(=O)CNC(=O)C2C1] |
| 31 | 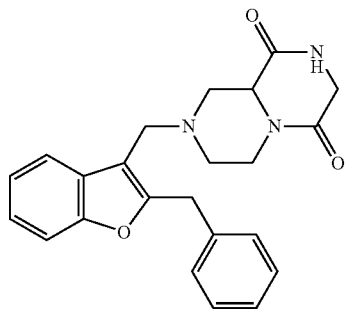 [SMILES: O=C1NCC(=O)N2CCN(Cc3c(Cc4ccccc4)oc4ccccc34)CC12] |
| 32 | 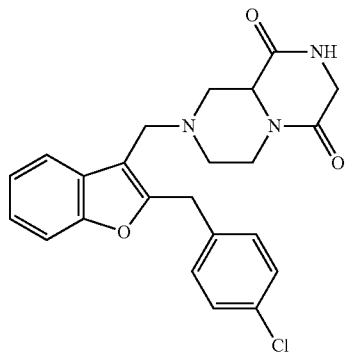 [SMILES: O=C1NCC(=O)N2CCN(Cc3c(Cc4ccc(Cl)cc4)oc4ccccc34)CC12] |
| 33 | 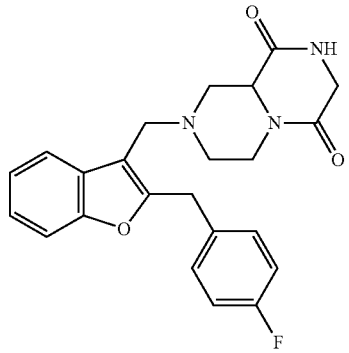 [SMILES: O=C1NCC(=O)N2CCN(Cc3c(Cc4ccc(F)cc4)oc4ccccc34)CC12] |

TABLE 2-continued

| Formula No. | Chemical Structure |
|---|---|
| 34 | 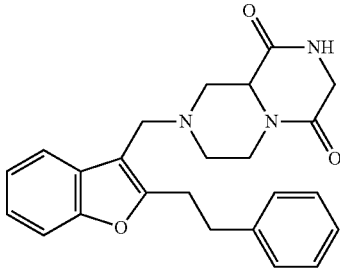 [SMILES: O=C1NCC(=O)N2CCN(Cc3c(CCc4ccccc4)oc4ccccc34)CC12] |
| — | — |

EXPERIMENTAL EXAMPLES

1. Anticancer Therapeutic Activity Enhancing Effect of Compound of Preparation Example 1-1

1-1. Paclitaxel Activity Enhancing Effect 1-1-1. Effect of Enhancing Activity Against Cancer Cells After cancer stem cell-like thyroid cancer cells derived from patients with relapse and metastasis after paclitaxel administration (ATC) were treated with a compound of Preparation Example 1-1 (150 nM) only; paclitaxel (12 nM) only; or a combination of paclitaxel (5 nM) and a compound of Preparation Example 1-1 (70 nM), a change in number of cells over time was confirmed. In addition, a change in cell viability according to a treatment concentration of paclitaxel, the compound of Preparation Example 1-1, or the combination of paclitaxel and the compound of Preparation Example 1-1 is shown in FIG. 1. In addition, the change in cell viability according to the treatment concentration of paclitaxel, the compound of Preparation Example 1-1 and the combination thereof was measured, and the result is shown in FIG. 2.

Figure 2:
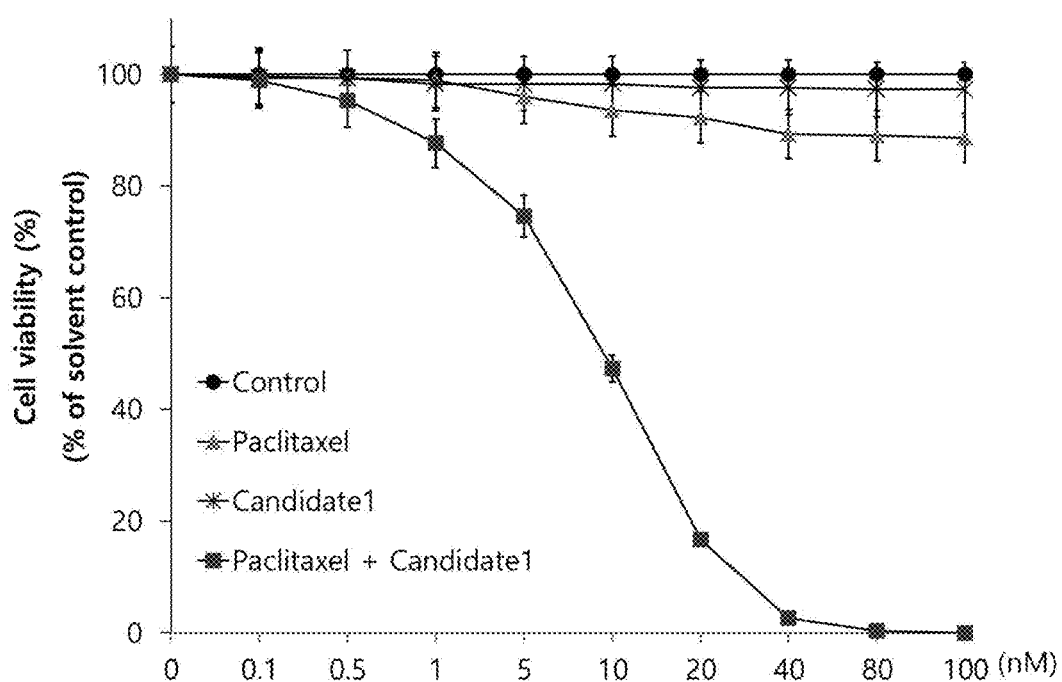
FIG. 2 shows the result of measuring the change in cell viability according to a treatment concentration after cancer stem cell-like thyroid cancer cells derived from patients with relapse and metastasis after paclitaxel administration are treated with a compound of Preparation Example 1-1 only; paclitaxel only; or the combination of paclitaxel and a compound of Preparation Example 1-1.

As shown in FIGS. 1 and 2, when anticancer agent-resistant thyroid cancer cells were treated with paclitaxel only, compared with a negative control, there were no change in cancer cell number and viability of cancer cells, but when the cells were treated with the compound of Preparation Example 1-1 and paclitaxel, it can be confirmed that the number and cell viability of the stem cell-like thyroid cancer cells remarkably decreased.

1-1-2. Analysis of Change in Tumor Size of Cancer Cell Xenograft Mouse

Figure 3:
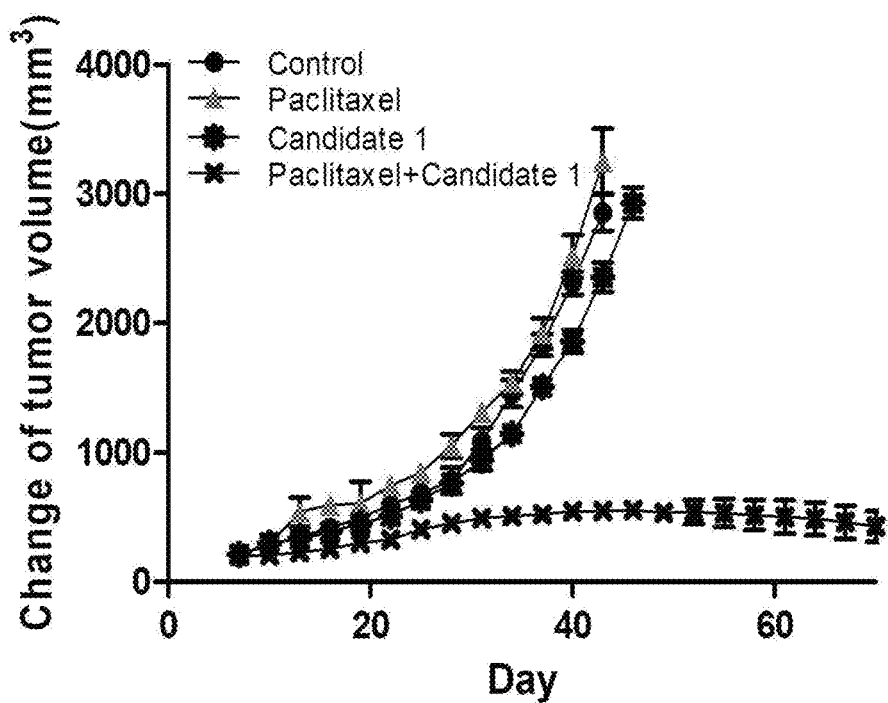
FIG. 3 shows the result of measuring the change in tumor volume over time after mouse models in which cancer stem cell-like thyroid cancer cells derived from patients with relapse and metastasis after paclitaxel administration are xenografted are subjected to oral administration of a compound of Preparation Example 1-1 only; intraperitoneal injection of paclitaxel only; or oral administration of a compound of Preparation Example 1-1 and then intraperitoneal injection of paclitaxel.

After cancer stem cell-like thyroid cancer cells derived from patients with relapse and metastasis after paclitaxel administration were cultured in vitro, the cultured cells were injected subcutaneously into the upper left flank of a BALB/c nude female mouse to be $2.0 \times 10^7$ cells/mouse. After 7 days, the mice were divided into groups of 10 each, and each group was subjected to oral administration of the compound of Preparation Example 1-1 (60 mg/kg) only; intraperitoneal injection of paclitaxel (25 mg/kg) only; or oral administration of the compound of Preparation Example 1-1 (27 mg/kg) and then intraperitoneal injection of paclitaxel (11 mg/kg). The mice were anesthetized to measure a change in tumor volume daily using calipers for 60 days, and the result is shown in FIG. 3. The tumor volume was evaluated using the following Equation 1.

$$\text{Tumor volume} = L \times S^2 / 2 \quad \text{[Equation 1]}$$

(however, L is the longest diameter, and S is the shortest diameter)

As shown in FIG. 3, when mouse models in which anticancer agent-resistant thyroid cancer cells were xenografted were administered paclitaxel only, compared with a negative control, there was no change in tumor volume. However, when the mouse models were treated with the compound of Preparation Example 1-1 and paclitaxel, it can be confirmed that the tumor volume remarkably decreased.

1-2. Effect of Enhancing Irinotecan Activity 1-2-1. Effect of Enhancing Activity Against Cancer Cells After cancer stem cell-like stomach cancer cells derived from patients with relapse and metastasis after irinotecan administration were treated with the compound of Preparation Example 1-1 only (170 nM); irinotecan only (8.9 μM); or a combination of irinotecan (4.5 μM) and the compound of Preparation Example 1-1 (75 nM), a change in cell number over treatment time was measured, and the result is shown in FIG. 4.

Figure 4:
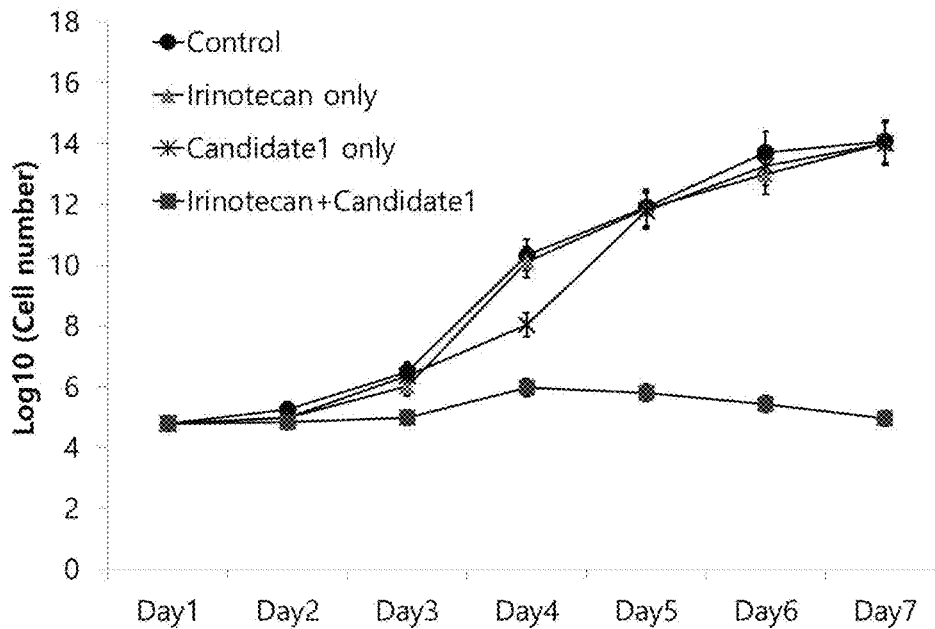
FIG. 4 shows the result of measuring a change in number of cells over treatment time after cancer stem cell-like stomach cancer cells derived from patients with relapse and metastasis after irinotecan administration are treated with a compound of Preparation Example 1-1 only; irinotecan only; or the combination of irinotecan and a compound of Preparation Example 1-1.

As shown in FIG. 4, when anticancer agent-resistant stomach cancer cells were treated with irinotecan only, compared with a negative control, there was no change in number of cancer cells. However, when the cancer cells were treated with the compound of Preparation Example 1-1 and irinotecan, it can be confirmed that the number of cancer cells remarkably decreased.

1-2-2. Analysis of Change in Tumor Size of Cancer Cell Xenograft Mouse

Figure 5:
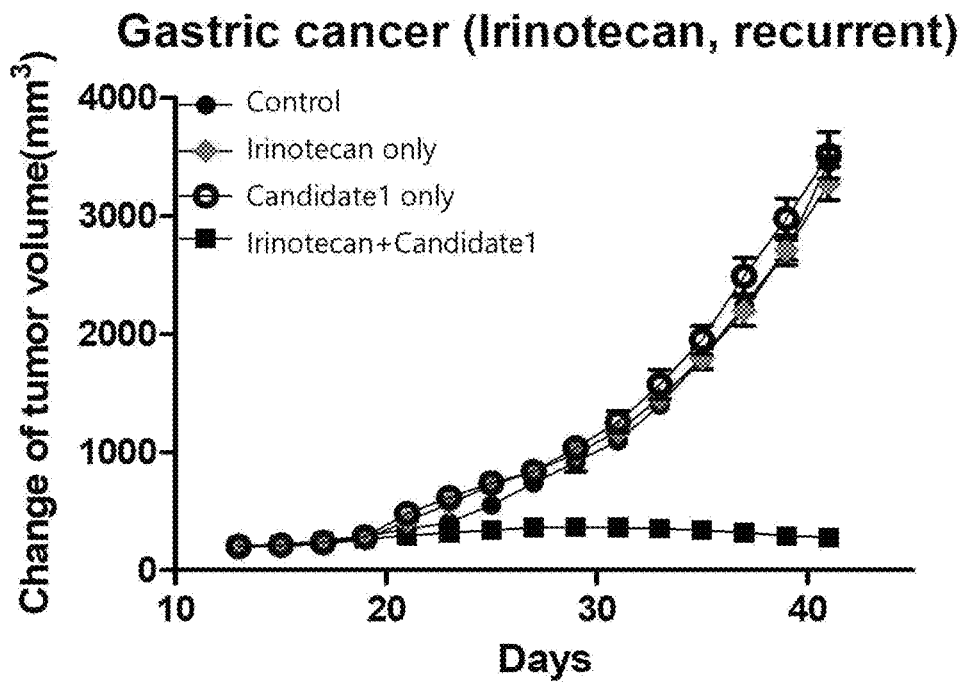
FIG. 5 shows the result of measuring a change in tumor volume over time after mouse models in which cancer stem cell-like stomach cancer cells derived from patients with relapse and metastasis after irinotecan administration are xenografted are subjected to oral administration of a compound of Preparation Example 1-1 only; oral administration of irinotecan only; or oral administration of a compound of Preparation Example 1-1 and irinotecan.

After the cancer stem cell-like stomach cancer cells derived from patients with relapse and metastasis after irinotecan administration were cultured in vitro, the cultured cells were subcutaneously injected into the upper left flank of a BALB/c nude female mouse to be $2.0 \times 10^7$ cells/mouse. After 7 days, the mice were divided into groups of 10 each, and each group was subjected to oral administration of the compound of Preparation Example 1-1 (70 mg/kg) only; oral administration of irinotecan (75 mg/kg) only; or oral administration of the compound of Preparation Example 1-1 (32 mg/kg) and irinotecan (55 mg/kg). The mice were anesthetized to measure a change in tumor volume daily using calipers for 40 days, and the result is shown in FIG. 5. The tumor volume was calculated by the above-described Equation 1. In addition, after 40 days, the tumor volume was measured, and the result is shown in FIG. 6, and for 41 days, the body weights of the mice were measured daily, and the result is shown in FIG. 7.

Figure 6:
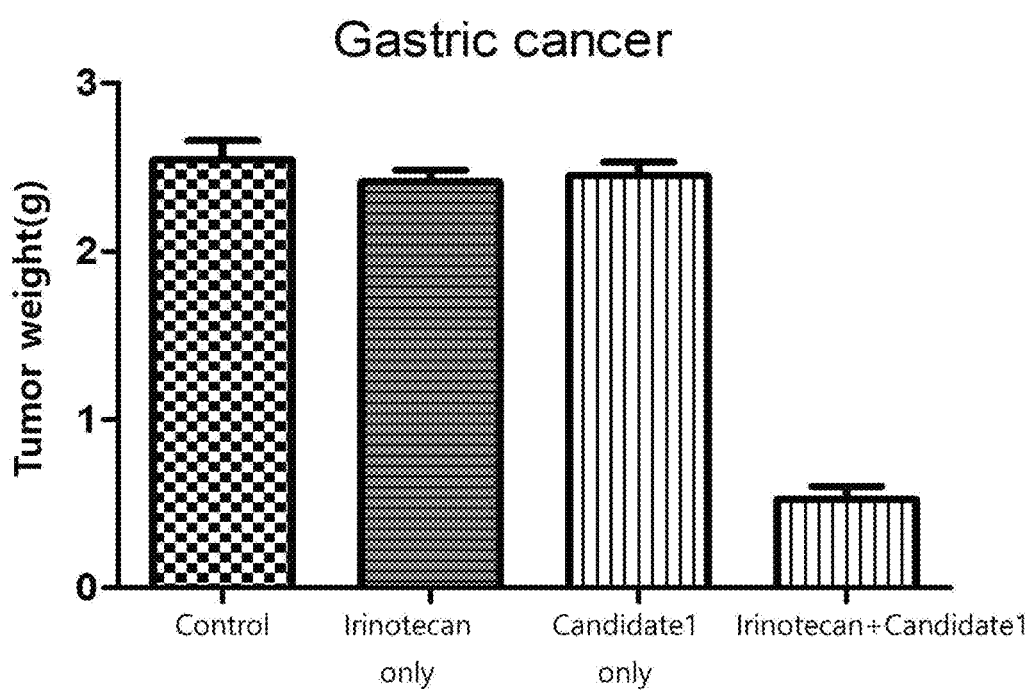
FIG. 6 shows the result of measuring the change in tumor weight over time after mouse models in which cancer stem cell-like stomach cancer cells derived from patients with relapse and metastasis after irinotecan administration are xenografted are subjected to oral administration of a compound of Preparation Example 1-1 only; oral administration of irinotecan only; or oral administration of a compound of Preparation Example 1-1 and irinotecan.

As shown in FIGS. 5 and 6, when the mouse model in which anticancer agent-resistant stomach cancer cells were xenografted were treated with irinotecan only, compared with a negative control, there was no change in tumor volume or weight. However, when the mouse model was treated with irinotecan and the compound of Preparation Example 1-1, it can be confirmed that the tumor volume and weight remarkably decreased.

Figure 7:
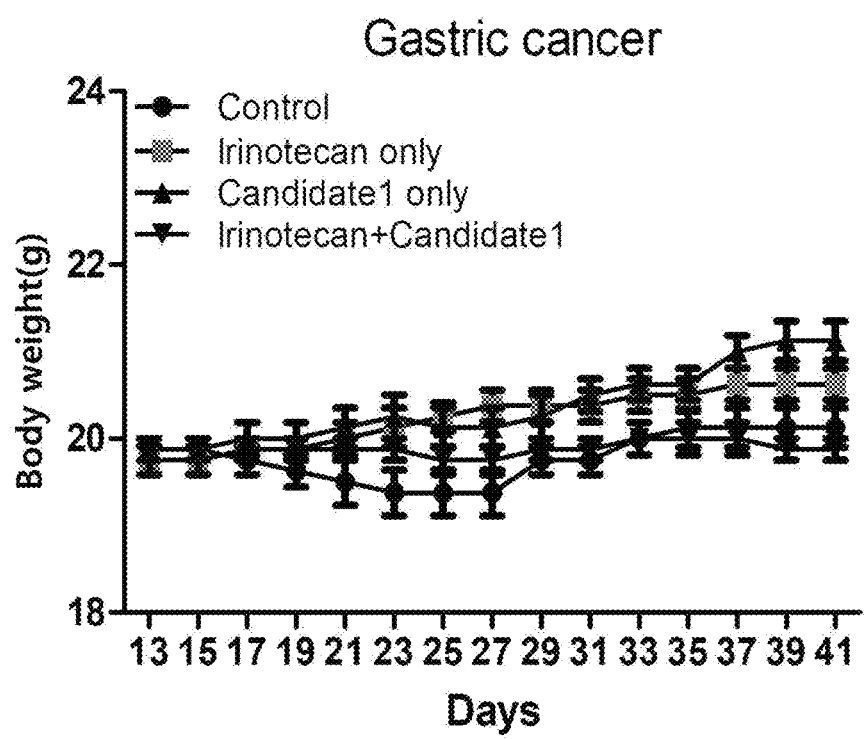
FIG. 7 shows the result of measuring the change is body weight of a mouse over time after mouse models in which cancer stem cell-like stomach cancer cells derived from patients with relapse and metastasis after irinotecan administration are xenografted are subjected to oral administration of a compound of Preparation Example 1-1 only; oral administration of irinotecan only; or oral administration of a compound of Preparation Example 1-1 and irinotecan.

In addition, as shown in FIG. 7, when the mouse model was treated with the compound of Preparation Example 1-1 alone or in combination with irinotecan, compared with a negative control, as it can be seen that there was no change in body weight of the mouse, it can be confirmed that there was no toxicity problem.

1-3. Effect of Enhancing Radiation Treatment Activity 1-3-1. Effect of Enhancing Activity Against Cancer Cells After cancer stem cell-like colorectal cancer cells derived from patients with relapse and metastasis after radiation therapy were treated with the compound of Preparation Example 1-1 (150 nM) only; Faxitron X-rays (Faxitron Bioptics, AZ, USA) at an intensity of 5 Gy (RT); or the compound of Preparation Example 1-1 (75 nM) and the X-rays at an intensity of 5 Gy, the change in number of cancer cells over treatment time was measured, and the result is shown in FIG. 8.

Figure 8:
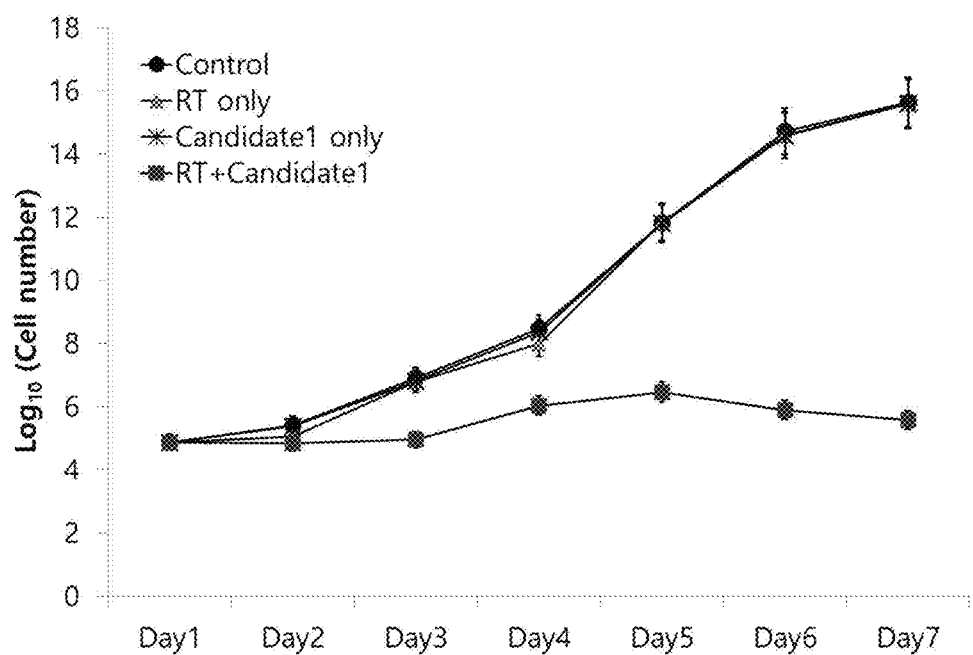
FIG. 8 shows the result of measuring the change in number of cells over treatment time after cancer stem cell-like colorectal cancer cells derived from patients with relapse and metastasis after radiation are treated with a compound of Preparation Example 1-1 only; with radiation; or the combination of the treatment with a compound of Preparation Example 1-1 and radiation.

As shown in FIG. 8, when the radiation-resistant colorectal cancer cells were treated with radiation therapy only, compared with a negative control, there was no change in number of cancer cells. However, when the cancer cells were treated with radiation therapy and the compound of Preparation Example 1-1, it can be confirmed that the number of cancer cells remarkably decreased.

1-3-2. Analysis of Change in Tumor Size of Mouse

Figure 9:
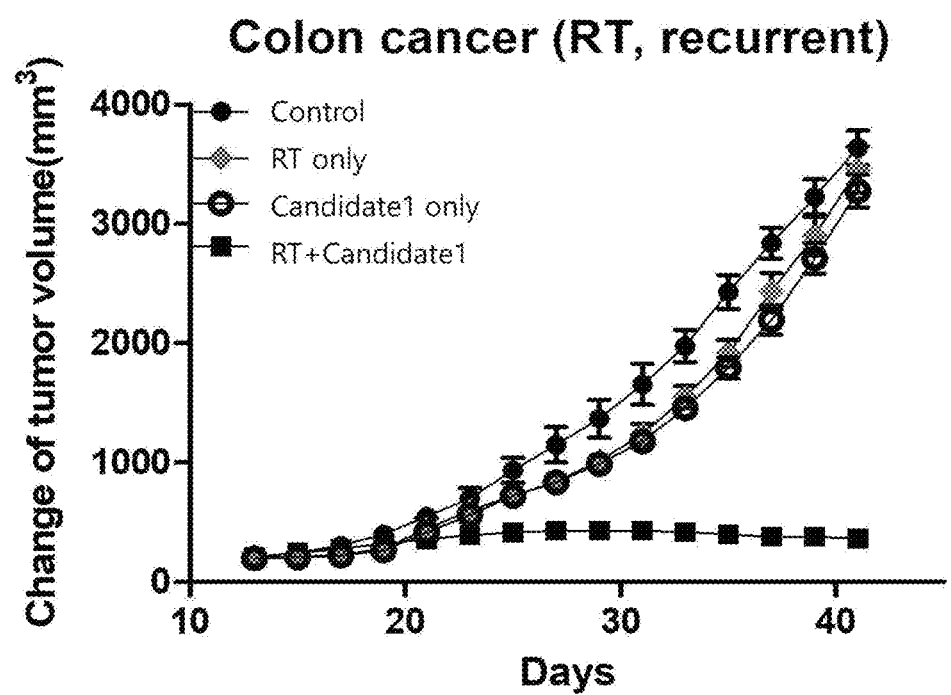
FIG. 9 shows the result of measuring the change in tumor volume over time after a mouse model in which cancer stem cell-like colorectal cancer cells derived from patients with relapse and metastasis after radiation are xenografted is subjected to oral administration of a compound of Preparation Example 1-1 only; radiation; or the combination of oral administration of a compound of Preparation Example 1-1 and radiation.

After cancer stem cell-like colorectal cancer cells, which were derived from patients with relapse and metastasis after radiation therapy, were cultured in vitro, the cultured cells were injected subcutaneously into the upper left flank of a BALB/c nude female mouse to be $2.0 \times 10^7$ cells/mouse. After 7 days, the mice were divided into groups of 10 each, and each group was subjected to oral administration of the compound of Preparation Example 1-1 (60 mg/kg); irradiation of Faxitron X-rays (Faxitro Bioptics, AZ, USA) at an intensity of 5 Gy; or oral administration of the compound of Preparation Example 1-1 (27 mg/kg) and the irradiation of the X-rays at an intensity of 5 Gy. The mice were anesthetized to measure a change in tumor volume daily using calipers for 40 days, and the result is shown in FIG. 9. The tumor volume was calculated by the above-described Equation 1. In addition, after 40 days, a tumor weight was measured, and the result is shown in FIG. 10, and for 41 days, the body weight of the mouse was measured, and the result is shown in FIG. 11.

Figure 10:
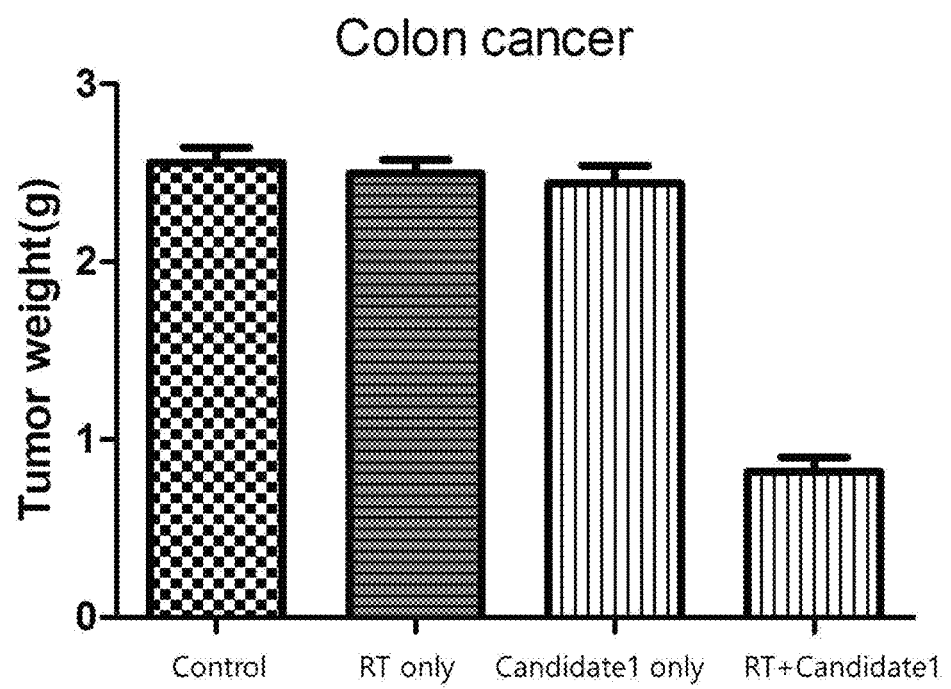
FIG. 10 shows the result of measuring the change in tumor weight over time after a mouse model in which cancer stem cell-like colorectal cancer cells derived from patients with relapse and metastasis after radiation are xenografted is subjected to oral administration of a compound of Preparation Example 1-1 only; radiation; or the combination of oral administration of a compound of Preparation Example 1-1 and radiation.
Figure 11:
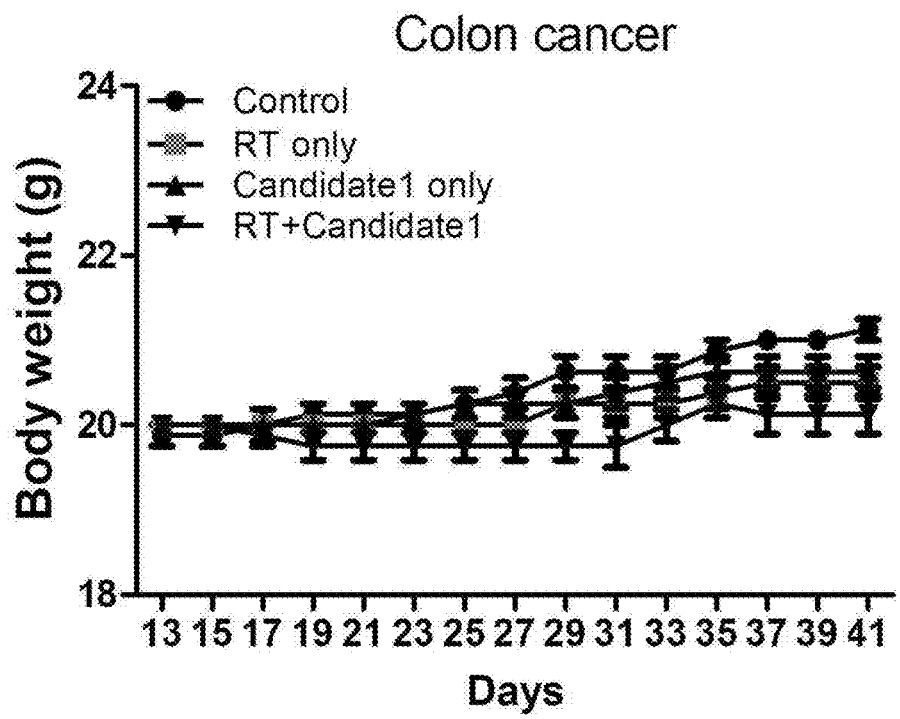
FIG. 11 shows the result of measuring the change in body weight of a mouse after a mouse model in which cancer stem cell-like colorectal cancer cells derived from patients with relapse and metastasis after radiation are xenografted is subjected to oral administration of a compound of Preparation Example 1-1 only; radiation; or the combination of oral administration of a compound of Preparation Example 1-1 and radiation.

As shown in FIGS. 9 and 10, when the mouse models in which radiation-resistant colorectal cancer cells were xenografted were treated with radiation therapy only, compared with a negative control, there was no change in tumor volume or weight, whereas when the mouse models were treated with radiation therapy and the compound of Preparation Example 1-1, it can be confirmed that the tumor volume and weight remarkably decreased. In addition, as shown in FIG. 11, when the mouse models were treated with the compound of Preparation Example 1-1 only or in combination with radiation therapy, compared with a negative control, as it can be seen that there was no change in body weight of the mouse, it can be confirmed that there was no toxicity problem.

2. Anticancer Therapeutic Activity Enhancing Effects of Compounds of Preparation Examples 2-1. Experimental Method To confirm the anticancer therapeutic activity enhancing effects of the compounds of Preparation Examples, the compounds or salts prepared in Preparation Examples 1-1 to 31 (hereinafter, the compounds of Preparation Examples) were used, and cellular experiments were carried out with an epithelial ovarian cancer cell line SKOV3 and SKOV3-TR derived therefrom and produced as a resistant cell line having resistance to a paclitaxel anticancer agent.

The two cell lines grown in 12-well plates were treated with 2 μM of the compound of each Preparation Example only; paclitaxel (0.2 μM for SKOV3, 5 μM for SKOV3-TR) only; or a combination of paclitaxel and the compound of each Preparation Example to measure the number of living cells after 72 hours. In the co-treatment with paclitaxel and the compound of each Preparation Example, first after 4-hour pretreatment with 2 μM each of the compounds of Preparation Examples, paclitaxel was treated at 5 μM for the SKOV3-TR cell line, and 0.2 μM for the SKOV3 cell line.

For the morphological analysis of the cells, 24, 48 and 72 hours after paclitaxel treatment, images of cells treated with "None (untreated sample)", "DMSO (paclitaxel solvent)", "ethanol (solvent for the compounds of Preparation Examples)", "paclitaxel", "paclitaxel+ethanol", and "paclitaxel+the compound of Preparation Example 1-2 (L19001)" were obtained. In addition, for the analysis of cell viability, 72 hours after treatment with paclitaxel or the compound of each Preparation Example only, or co-treatment with paclitaxel and the compound of each Preparation Example, the number of living cells was measured through Image J analysis.

2-2. Analysis of Cell Morphology

Figure 12:
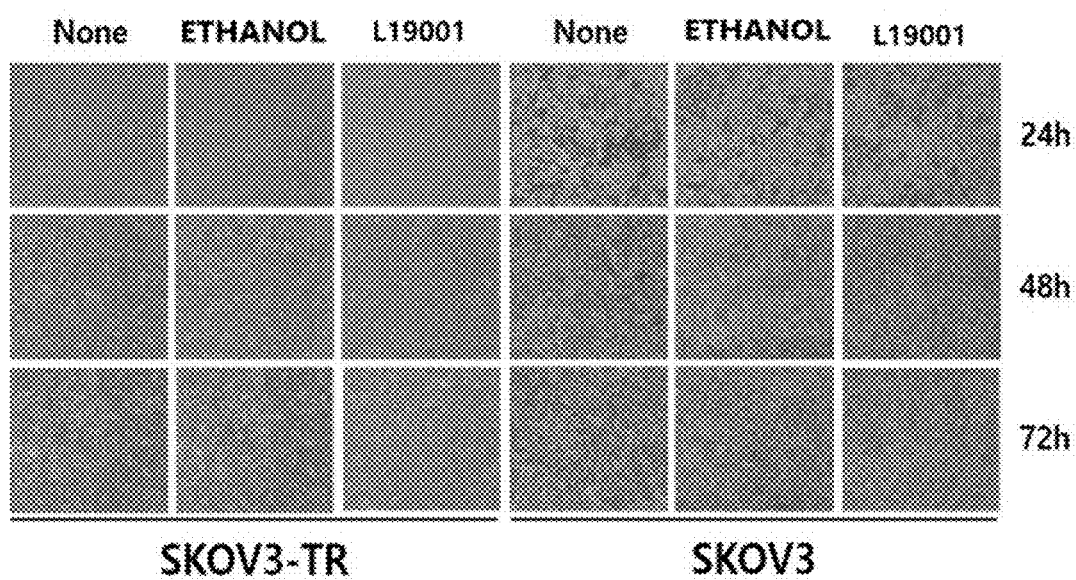
FIG. 12 shows the result of confirming cell morphology after each of SKOV3 which is an epithelial ovarian cancer cell line and SKOV3-TR produced as a resistant cell line having a resistance to an anticancer agent paclitaxel is not treated with any agent (None), treated with ethanol (solvent for a compound of Preparation Example), or treated with a compound of Preparation Example 1-2.

As a result of the morphological analysis of cells, in the cases of the groups treated with DMSO and ethanol only, respectively, compared with an untreated group (None), since there was no specific difference, it cannot be seen that the amount of a solvent used in this experiment did not affect the cells. In addition, the single treatment with each of the compounds of Preparation Examples did not cause a particular morphological change in the cases of SKOV3-TR and SKOV3. FIG. 12 shows the images captured 24, 48 and 72 hours after treatment with None, ethanol, and the compound of Preparation Example 1-2 (L19001, 2 μM).

In addition, to confirm whether the compounds of Preparation Examples can enhance the anticancer efficacy of paclitaxel, 4 hours before paclitaxel treatment, the compounds of Preparation Examples were pretreated, and then the effect on cancer cell death by paclitaxel was evaluated. In the paclitaxel treatment, the decrease in number of living cells caused by the induction of cell death and the inhibition of cell growth was confirmed in SKOV3-TR and SKOV3.

Figure 13:
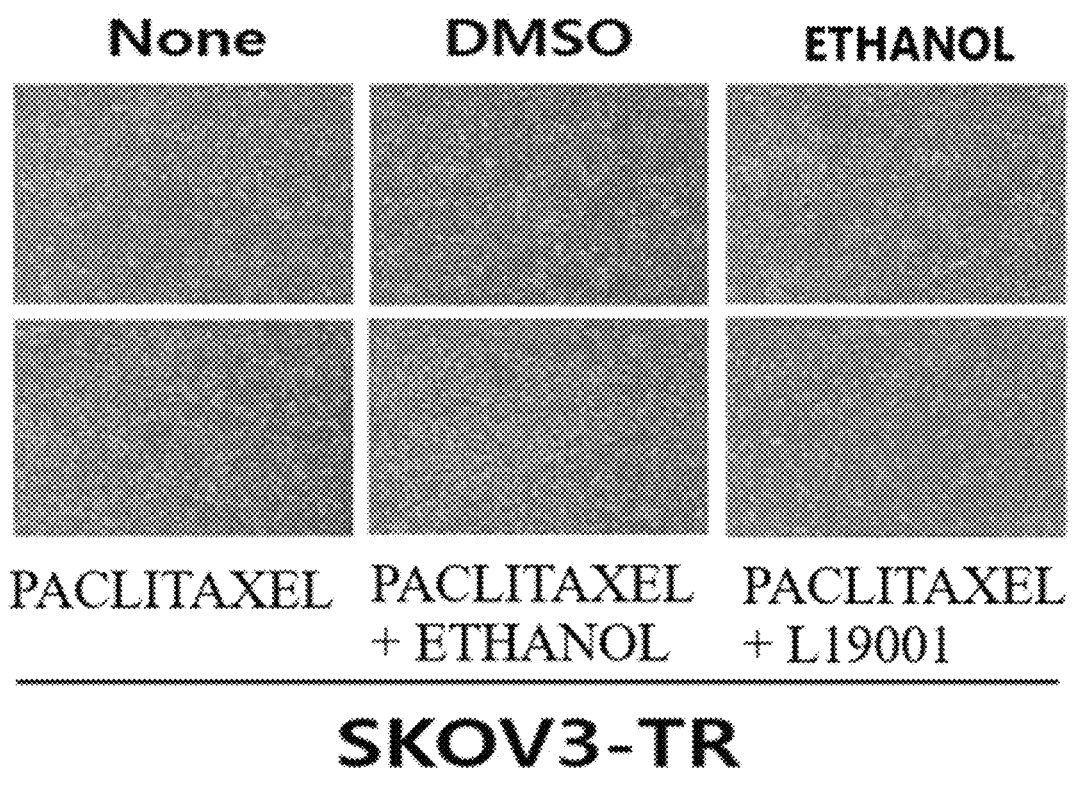
FIG. 13 shows images obtained 72 hours after treatment of a SKOV3-TR cell line with paclitaxel only or the combination of paclitaxel and a compound of Preparation Example 1-2.
Figure 14:
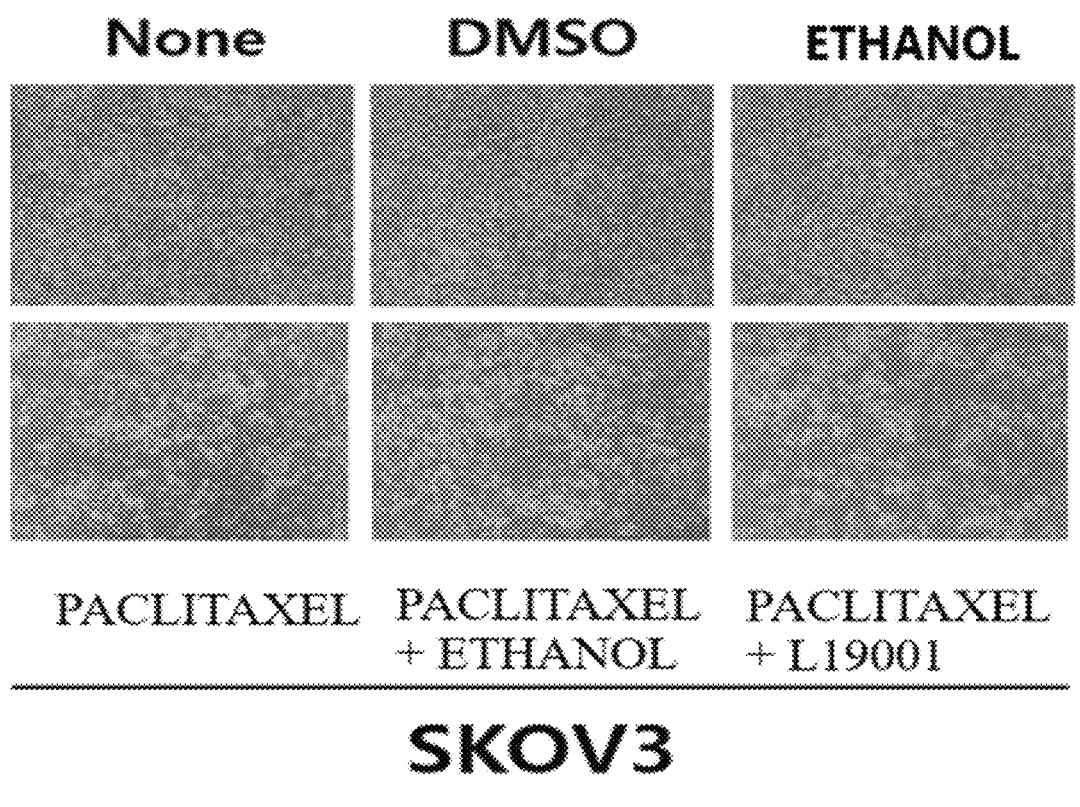
FIG. 14 shows images obtained 72 hours after treatment of a SKOV3 cell line with paclitaxel only or the combination of paclitaxel and a compound of Preparation Example 1-2.

Specifically, in the resistant cancer cell line SKOV3-TR, these phenomena become more pronounced by the treatment with the compounds of Preparation Examples without exception, whereas in the general cancer cell line SKOV3, the synergistic effect of paclitaxel on cancer cell death by treatment with the compounds of Preparation Examples was not clearly shown as in SKOV3-TR. FIGS. 13 and 14 show images obtained 72 hours after the two types of cell lines were treated with paclitaxel only or paclitaxel+the compound of Preparation Example 1-2 (L19001).

2-3. Analysis of Cell Viability

The cell viability of the two types of cancer cell lines was analyzed by measuring the number of living cells using the ImageJ program.

As shown in FIGS. 15 to 18, in the cases of the groups treated with DMSO and ethanol only, respectively, compared with an untreated group (None), since there was no specific difference in cell viability, it can be seen that the amount of a solvent used in this experiment did not affect cell viability.

Figure 15:
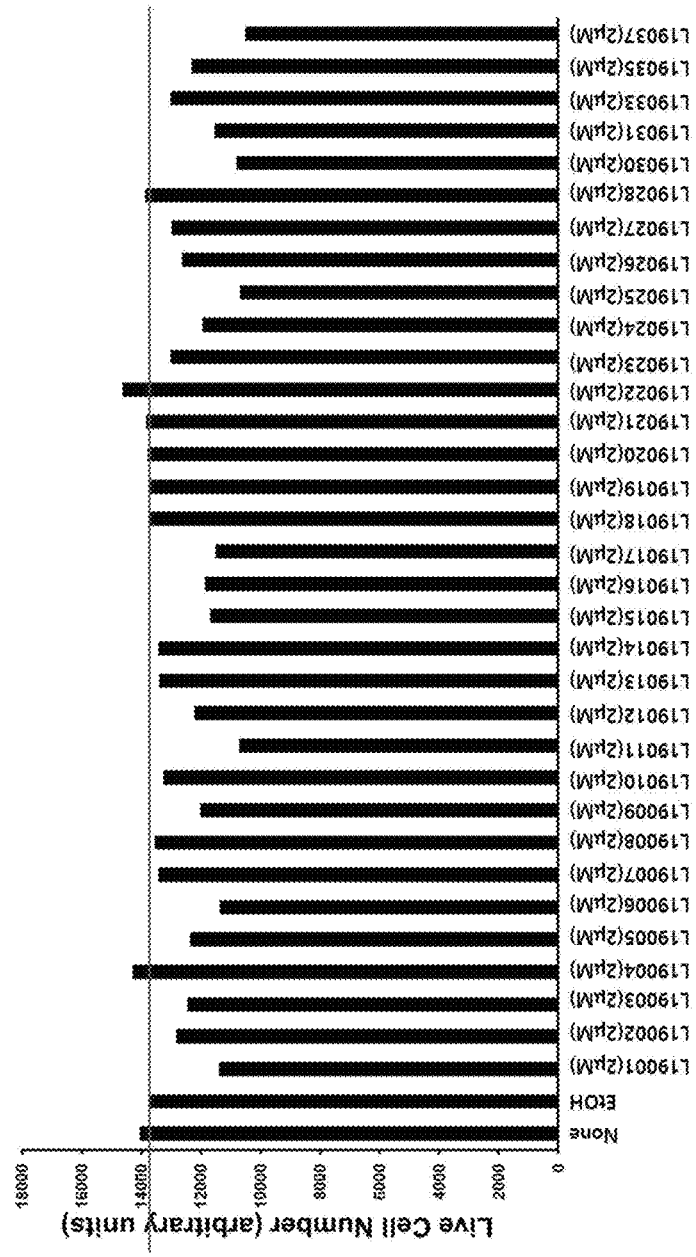
FIG. 15 shows the number of cells 72 hours after treatment of a SKOV3-TR cell line with none; ethanol; and 2 µM each of compounds of Preparation Examples.
Figure 16:
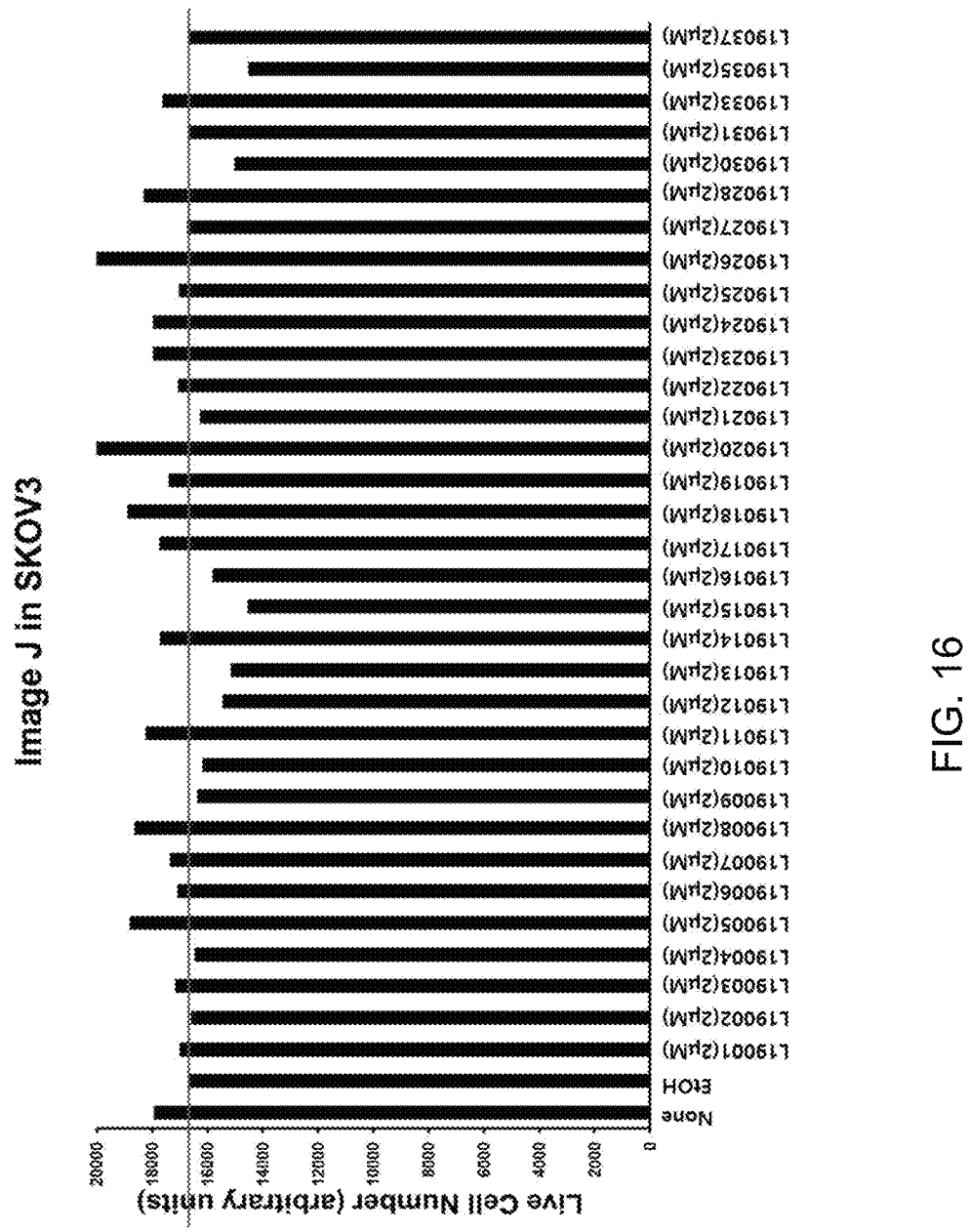
FIG. 16 shows the number of cells 72 hours after treatment of a SKOV3 cell line with none; ethanol; and 2 µM each of compounds of Preparation Examples.

To confirm whether a compound of Preparation Example affects cell viability, 72 hours after the SKOV3-TR and SKOV3 cell lines were treated with 2 µM each of the compounds of Preparation Examples, the number of cells was measured. As a result, when the cell lines were treated with each of the compounds of Preparation Examples only, they did not greatly affect cell viability in the SKOV3-TR and SKOV3 cell lines. FIGS. 15 and 16 show the numbers of cells 72 hours after the SKOV3-TR and SKOV3 cell lines were treated with None, ethanol and each of the compounds of Preparation Examples.

Figure 17:
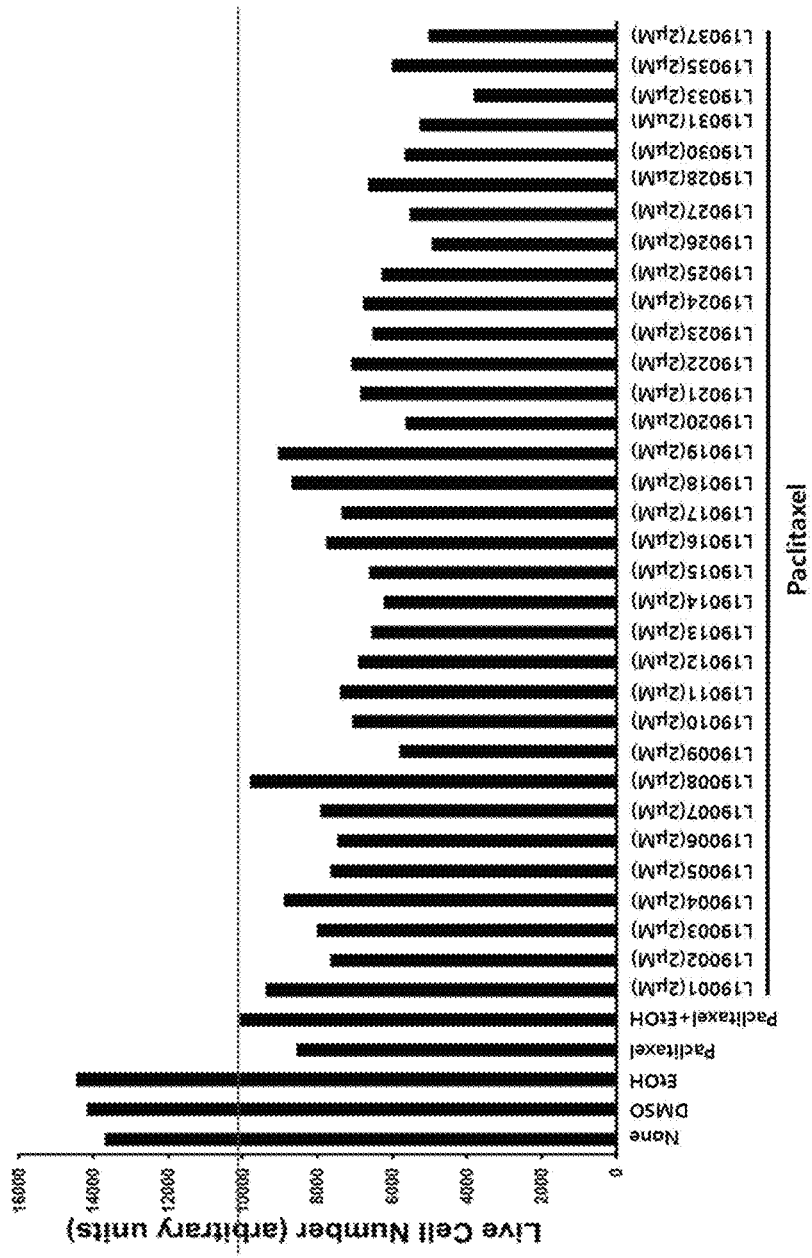
FIG. 17 shows the number of cells 72 hours after treatment of a SKOV3-TR cell line with none; ethanol; DMSO (paclitaxel solvent); paclitaxel only; and the combination of paclitaxel and each (2 µM) of compounds of Preparation Examples.
Figure 18:
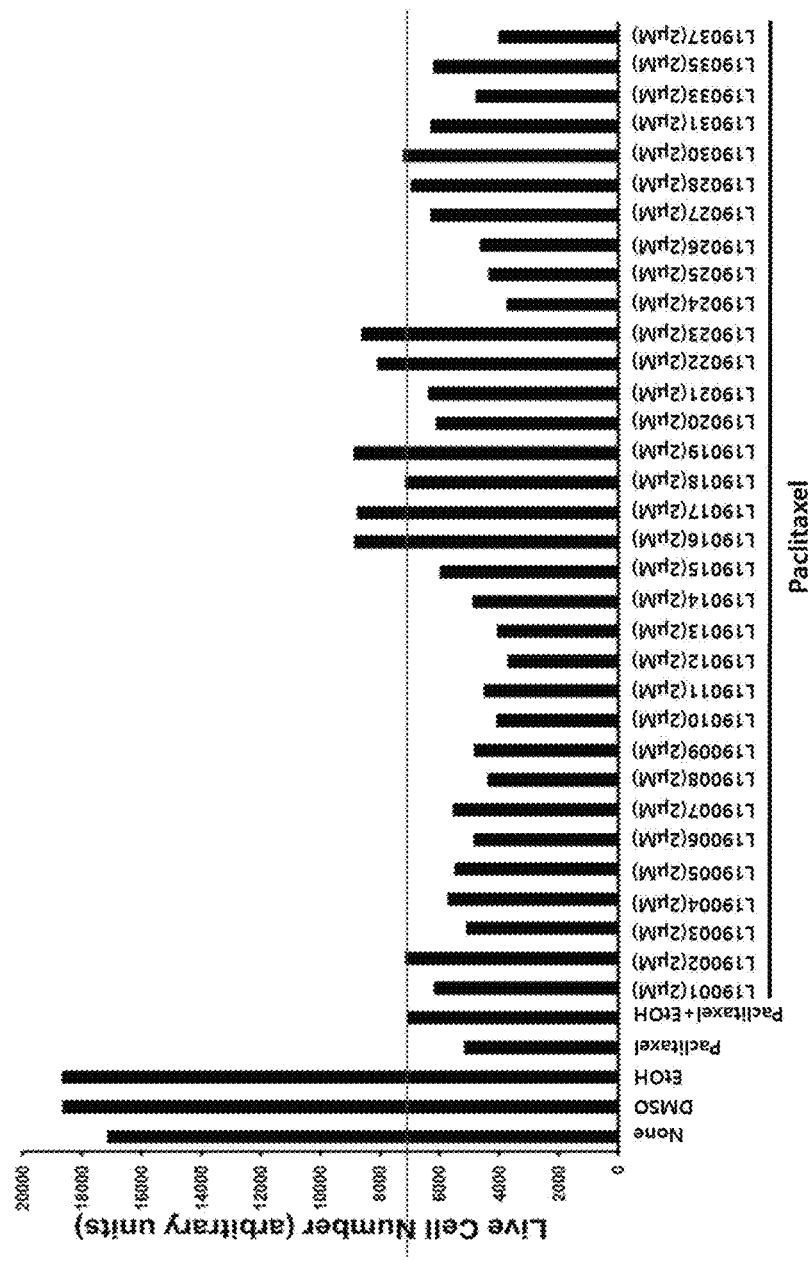
FIG. 18 shows the number of cells 72 hours after treatment of a SKOV3 cell line with none; ethanol; DMSO (paclitaxel solvent); paclitaxel only; and the combination of paclitaxel and each (2 µM) of compounds of Preparation Examples.

In addition, to investigate whether the compounds of Preparation Examples can enhance the anticancer efficacy of paclitaxel, four hours before paclitaxel treatment, 2 µM each of the compounds of Preparation Examples was pretreated, and then the effect of paclitaxel on cancer cell death was evaluated. As a result, compared with single treatment of paclitaxel, in paclitaxel treatment after the pretreatment of the compounds of Preparation Examples, the decrease in number of cells was confirmed in the SKOV3-TR and SKOV3 cell lines due to the induction of cell death and inhibition of cell growth. Particularly, compared with the general cancer cell line SKOV3, these phenomena become more pronounced by the treatment with the compounds of Preparation Examples without exception. FIGS. 17 and 18 show the numbers of cells measured 72 hours after treatment of the SKOV3-TR and SKOV3 cell lines with None, DMSO, ethanol and paclitaxel only, and the pretreatment of each of the compounds of Preparation Examples and then paclitaxel treatment.

What is claimed is:

1. A compound represented by Formula 1 or a pharmaceutically acceptable salt thereof:

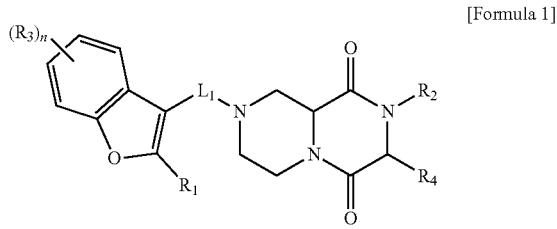

[Formula 1]

wherein n is an integer of 0 to 4;
$R_1$ is hydrogen, $C_1$ to $C_{10}$ alkyl or C1 to C4 alkyl substituted with aryl;
each $R_3$ is independently C1 to C6 alkyl;
$L_1$ is a direct bond, or C1 to C6 alkylene;
$R_2$ is hydrogen, C1 to C10 alkyl or C1 to C4 alkyl substituted with aryl, and $R_4$ is hydrogen, C1 to C4 alkyl, C3 to C8 cycloalkyl or C1 to C4 alkyl substituted with aryl, or
$R_2$ and $R_4$ are connected to form a 4 to 7-membered ring;

the alkyl of $R_1$ to $R_4$, the arylalkyl of $R_1$, $R_2$ and $R_4$, the cycloalkyl of $R_4$, the alkylene of $L_1$ are each independently optionally substituted with a substituent selected from the group consisting of a C1 to C6 alkyl group, a halo group, an aryl group, a haloalkyl group, a nitro group, a cyano group, an alkylthio group or an arylalkylthio group, and when the compound is substituted with a plurality of substituents, the substituents are the same or different; and R2 and R4 are not hydrogen at the same time.

2. The compound of claim 1, wherein n is an integer of 0 to 2;
$R_1$ is C1 to C6 alkyl or C1 to C4 alkyl substituted with aryl;
$L_1$ is C1 to C4 alkylene; and
$R_2$ is hydrogen, C1 to C6 alkyl or C1 to C4 alkyl substituted with aryl, and $R_4$ is hydrogen, C1 to C4 alkyl, C3 to C6 cycloalkyl or C1 to C4 alkyl substituted with aryl, or
$R_2$ and $R_4$ are connected to form a 4 to 6-membered ring.

3. The compound of claim 1, wherein n is an integer of 0 to 1;
$R_1$ is C1 to C6 alkyl, phenylmethyl or phenylethyl;
$L_1$ is C1 to C2 alkylene;
$R_2$ is hydrogen, C1 to C6 alkyl, phenylmethyl or phenylethyl,
$R_4$ is hydrogen, C1 to C2 alkyl, C5 to C6 cycloalkyl, phenylmethyl or naphthylmethyl, or
$R_2$ and $R_4$ are connected to form a 5 to 6-membered ring.

4. The compound of claim 1, which is selected from the group consisting of:

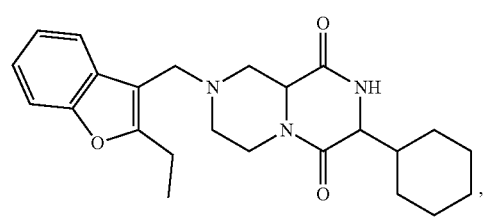

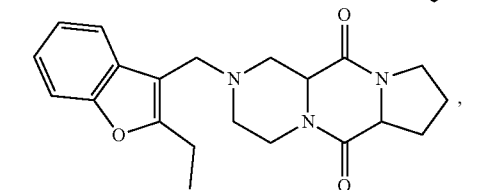

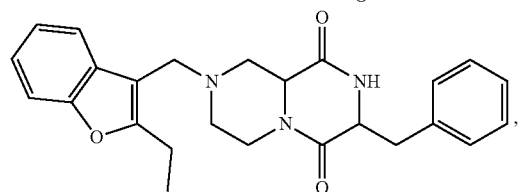

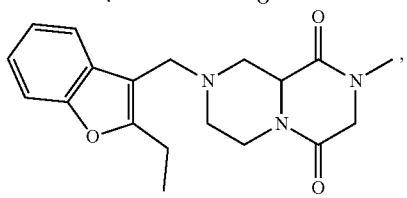

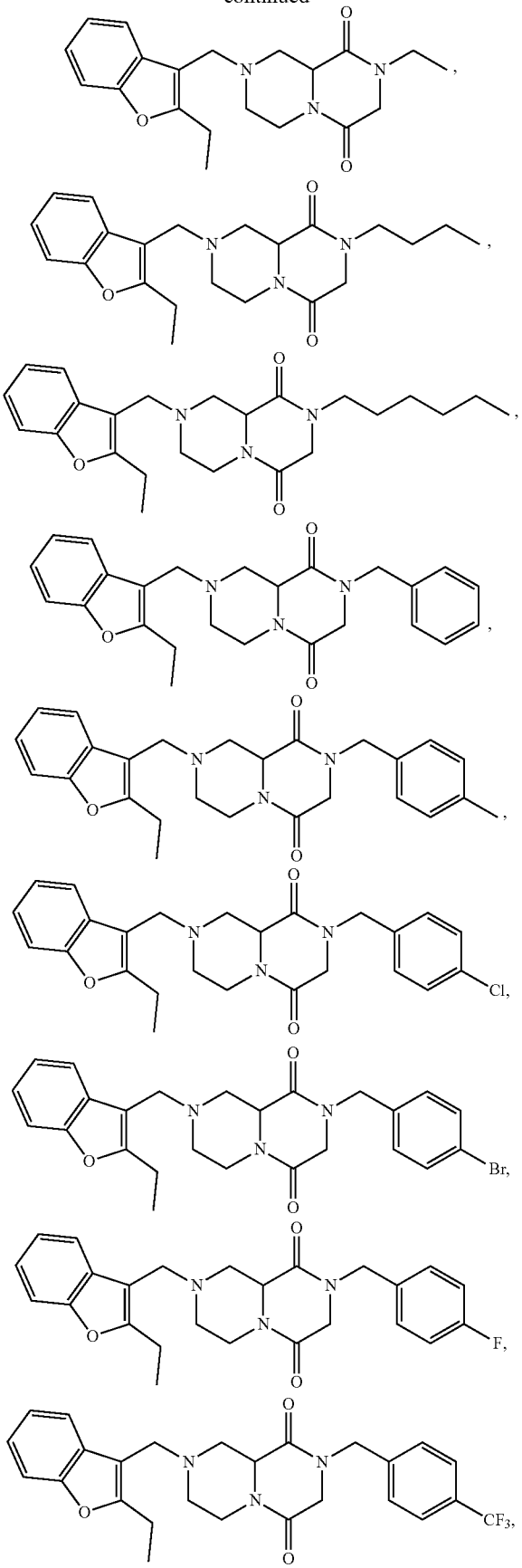

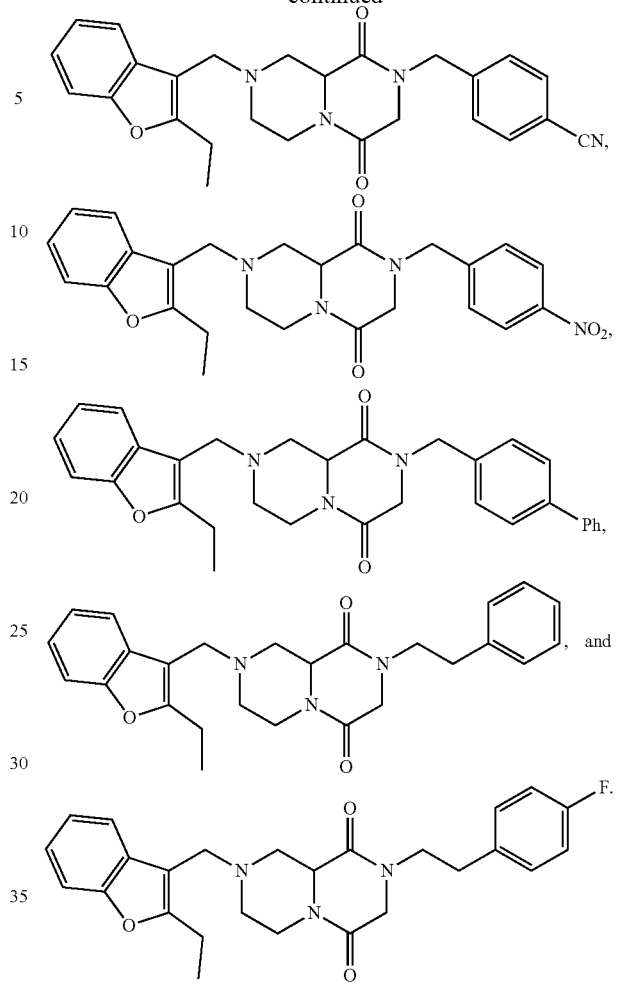

5. A pharmaceutical composition, comprising the compound of claim 1 or a pharmaceutically acceptable salt thereof, and a pharmaceutically acceptable carrier.

6. The pharmaceutical composition of claim 5, wherein n is an integer of 0 to 2;
$R_1$ is C1 to C6 alkyl or C1 to C4 alkyl substituted with aryl;
$L_1$ is C1 to C4 alkylene; and
$R_2$ is hydrogen, C1 to C6 alkyl or C1 to C4 alkyl substituted with aryl, and $R_4$ is hydrogen, C1 to C4 alkyl, C3 to C6 cycloalkyl or C1 to C4 alkyl substituted with aryl, or
$R_2$ and $R_4$ are connected to form a 4 to 6-membered ring.

7. The pharmaceutical composition of claim 5, wherein n is an integer of 0 to 1;
$R_1$ is C1 to C6 alkyl, phenylmethyl or phenylethyl;
$L_1$ is C1 to C2 alkylene;
$R_2$ is hydrogen, C1 to C6 alkyl, phenylmethyl or phenylethyl, $R_4$ is hydrogen, C1 to C2 alkyl, C5 to C6 cycloalkyl, phenylmethyl or naphthylmethyl, or
$R_2$ and $R_4$ are connected to form a 5 to 6-membered ring.

8. The pharmaceutical composition of claim 6, further comprising an anticancer agent which is at least one of a taxene-based anticancer agent and a camptothecin-based anticancer agent.

9. The pharmaceutical composition of claim 8, wherein the taxene-based anticancer agent is at least one selected from the group consisting of paclitaxel, docetaxel and cabazitaxel.

10. The pharmaceutical composition of claim 8, wherein the camptothecin-based anticancer agent is at least one selected from the group consisting of irinotecan, topotecan and belotecan.

11. The pharmaceutical composition of claim 8, wherein the anticancer agent is at least one selected from the group consisting of nitrogen mustard, imatinib, oxaliplatin, rituximab, erlotinib, neratinib, lapatinib, gefitinib, vandetanib, nilotinib, semasanib, bosutinib, axitinib, macitinib, cediranib, restaurtinib, trastuzumab, gefitinib, bortezomib, sunitinib, pazopanib, toceranib, nintedanib, regorafenib, semaksanib, tibozanib, ponatinib, cabozantinib, carboplatin, sorafenib, renbatinib, bevacizumab, cisplatin, cetuximab, viscumalbum, asparaginase, tretinoin, hydroxycarbamide, dasatinib, estramustine, gemtuzumab ozogamycin, ibritumomab tucetan, heptaplastin, methylaminolevulinic acid, amsacriine, alemtuzumab, procarbazine, alprostadil, holmium nitrate, chitosa, gemcitabine, doxyfluridine, pemetrexed, tegapur, capecitabine, gimeracil, oteracil, azacitidine, methotrexate, uracil, cytarabine, 5-fluorouracil, fludagabine, enocitabine, flutamide, kefecitabine, decitabine, mercaptopurine, thioguanine, cladribine, carmofur, raltitrexed, docetaxel, paclitaxel, irinotecan, belotecan, topotecan, binorelbine, etoposide, vincristine, vinblastine, teniposide, doxorubicin, idarubicin, epirubicin, mitoxantrone, mitomycin, bleromycin, daunorubicin, dactinomycin, pararubicin, aclarubicin, pepromycin, temsirolimus, temozolomide, busulfan, ifosfamide, cyclophosphmide, melparan, altretmin, dacarbazine, thiotepa, bimustine, chlorambucil, mitoractol, leucovorin, tretonin, exnestane, aminoglutesimide, anagrelide, olaparib, navelbine, padrazol, tamoxifen, toremifen, testolactone, anastrozole, letrozole, borozole, bicalutamide, lomustine, vorinostat, entinostat and carmustine.

12. The pharmaceutical composition of claim 8, wherein the compound represented by Formula 1 or a pharmaceutically acceptable salt thereof and the anticancer agent are contained at a molar concentration ratio of 1:0.001 to 1:1000.

13. A method of treating cancer, comprising:
administering to a subject with resistant cancer a therapeutically effective amount of a compound of claim 1 or a pharmaceutically acceptable salt thereof,
wherein the resistant cancer is at least one selected from the group consisting of thyroid cancer, stomach cancer, colorectal cancer, ovarian cancer, breast cancer, lung cancer, Kaposi's sarcoma, cervical cancer, pancreatic cancer, head and neck cancer, rectal cancer, colon cancer, esophageal cancer and prostate cancer.

14. The method of claim 13, wherein the resistant cancer is resistant cancer against at least one of a taxene-based anticancer agent and a camptothecin-based anticancer agent.

15. The method of claim 13, wherein the resistant cancer is resistant cancer against radiation.

16. The method of claim 13, which produces enhancement in anticancer activity of an anticancer agent or radiation.

17. The method of claim 16, wherein the anticancer agent is at least one of a taxene-based anticancer agent and a camptothecin-based anticancer agent.

18. The method of claim 17, wherein the taxene-based anticancer agent is at least one selected from the group consisting of paclitaxel, docetaxel and cabazitaxel.

19. The method of claim 17, wherein the camptothecin-based anticancer agent is at least one selected from the group consisting of irinotecan, topotecan and belotecan.

* * * * *